(12) United States Patent
Paul et al.

(10) Patent No.: US 9,358,110 B2
(45) Date of Patent: *Jun. 7, 2016

(54) MEDICAL DEVICES AND DELIVERY SYSTEMS FOR DELIVERING MEDICAL DEVICES

(71) Applicant: BOSTON SCIENTIFIC SCIMED, INC., Maple Grove, MN (US)

(72) Inventors: David J. Paul, Scotts Valley, CA (US); Benjamin T. Sutton, Scotts Valley, CA (US); Brian K. McCollum, Redwood City, CA (US); Brian D. Brandt, San Jose, CA (US); Emma Leung, Santa Cruz, CA (US); Kenneth M. Martin, Woodside, CA (US); Amr Salahieh, Saratoga, CA (US); Daniel K. Hildebrand, San Francisco, CA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/144,899

(22) Filed: Dec. 31, 2013

(65) Prior Publication Data
US 2014/0114405 A1    Apr. 24, 2014

Related U.S. Application Data

(60) Division of application No. 13/287,420, filed on Nov. 2, 2011, now Pat. No. 8,617,236, which is a division of application No. 12/578,463, filed on Oct. 13, 2009, now Pat. No. 8,328,868, which is a (Continued)

(51) Int. Cl.
*A61F 2/24* (2006.01)
*A61F 2/90* (2013.01)
*A61F 2/95* (2013.01)

(52) U.S. Cl.
CPC ............ *A61F 2/2427* (2013.01); *A61F 2/2418* (2013.01); *A61F 2/2436* (2013.01);
(Continued)

(58) Field of Classification Search
USPC .................... 623/2.11, 2.14, 2.18, 1.11, 1.23; 606/191–201
See application file for complete search history.

(56) References Cited

U.S. PATENT DOCUMENTS

| 15,192 A | 6/1856 | Peale |
| 2,682,057 A | 6/1954 | Lord |

(Continued)

FOREIGN PATENT DOCUMENTS

| CN | 1338951 | 3/2002 |
| DE | 19532846 | 3/1997 |

(Continued)

OTHER PUBLICATIONS

A Matter of Size, Treiennial Review of the National Nanotechnology Initiative, 2006, v-13, The National Academies Press, Washington, DC http://www.nap.edu/catalog/11752.html.

(Continued)

*Primary Examiner* — Alvin Stewart
(74) *Attorney, Agent, or Firm* — Seager, Tufte & Wickhem LLP

(57) ABSTRACT

Medical devices and delivery systems for delivering medical devices to a target location within a subject. In some embodiments the medical devices can be locked in a fully deployed and locked configuration. In some embodiments the delivery systems are configured with a single actuator to control the movement of multiple components of the delivery system. In some embodiments the actuator controls the independent and dependent movement of multiple components of the delivery system.

11 Claims, 45 Drawing Sheets

Related U.S. Application Data continuation-in-part of application No. 10/982,388, filed on Nov. 5, 2004, now Pat. No. 7,959,666, and a continuation-in-part of application No. 11/275,912, filed on Feb. 2, 2006, now Pat. No. 7,824,443.

(60) Provisional application No. 61/104,509, filed on Oct. 10, 2008, provisional application No. 61/151,814, filed on Feb. 11, 2009.

(52) U.S. Cl.
CPC ............... *A61F2/2439* (2013.01); *A61F 2/90* (2013.01); *A61F 2/2412* (2013.01); *A61F 2/2433* (2013.01); *A61F 2002/9517* (2013.01); *A61F 2002/9528* (2013.01); *A61F 2220/0041* (2013.01); *A61F 2220/0075* (2013.01); *A61F 2230/0067* (2013.01); *A61F 2250/006* (2013.01)

(56) References Cited

U.S. PATENT DOCUMENTS

| | | |
|---|---|---|
| 2,701,559 A | 2/1955 | Cooper |
| 2,832,078 A | 4/1958 | Williams |
| 3,099,016 A | 7/1963 | Edwards |
| 3,113,586 A | 12/1963 | Edmark, Jr. |
| 3,130,418 A | 4/1964 | Head et al. |
| 3,143,742 A | 8/1964 | Cromie |
| 3,334,629 A | 8/1967 | Cohn |
| 3,367,364 A | 2/1968 | Cruz, Jr. et al. |
| 3,409,013 A | 11/1968 | Berry |
| 3,445,916 A | 5/1969 | Schulte |
| 3,540,431 A | 11/1970 | Mobin-Uddin |
| 3,548,417 A | 12/1970 | Kischer |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Van Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,483 A | 6/1993 | Tower |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |

(56) References Cited

U.S. PATENT DOCUMENTS

| | | |
|---|---|---|
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,500,014 A | 3/1996 | Quijano et al. |
| 5,507,767 A | 4/1996 | Maeda et al. |
| 5,534,007 A | 7/1996 | St. Germain et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,645,559 A | 7/1997 | Hachtman et al. |
| 5,662,671 A | 9/1997 | Barbut et al. |
| 5,667,523 A | 9/1997 | Bynon |
| 5,674,277 A | 10/1997 | Freitag |
| 5,693,083 A | 12/1997 | Baker et al. |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,059,827 A | 5/2000 | Fenton, Jr. |
| 6,074,418 A | 6/2000 | Buchanan et al. |
| 6,093,203 A | 7/2000 | Uflacker |
| 6,096,074 A | 8/2000 | Pedros |
| 6,123,723 A | 9/2000 | Konya |
| 6,132,473 A | 10/2000 | Williams et al. |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | DePaulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |

(56) References Cited

U.S. PATENT DOCUMENTS

| | | |
|---|---|---|
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Don Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B1 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,719,789 B2 | 4/2004 | Cox |
| 6,723,116 B2 | 4/2004 | Taheri |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat et al. |
| 6,773,454 B2 | 8/2004 | Wholey et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,821,297 B2 | 11/2004 | Snyders |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,097,658 B2 | 8/2006 | Oktay |
| 7,122,020 B2 | 10/2006 | Mogul |
| 7,125,418 B2 | 10/2006 | Duran et al. |
| 7,141,063 B2 | 11/2006 | White |
| 7,166,097 B2 | 1/2007 | Barbut |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 * | 11/2008 | Salahieh et al. ............ 623/2.18 |
| 7,470,285 B2 | 12/2008 | Nugent et al. |
| 7,473,417 B2 | 1/2009 | Zeltinger et al. |
| 7,491,232 B2 | 2/2009 | Bolduc et al. |
| 7,510,574 B2 | 3/2009 | Le et al. |
| 7,524,330 B2 | 4/2009 | Berreklouw |
| 7,530,995 B2 | 5/2009 | Quijano et al. |
| 7,544,206 B2 | 6/2009 | Cohn |
| 7,601,159 B2 | 10/2009 | Ewers et al. |
| 7,622,276 B2 | 11/2009 | Cunanan et al. |
| 7,628,802 B2 | 12/2009 | White et al. |
| 7,628,803 B2 | 12/2009 | Pavcnik et al. |
| 7,632,298 B2 | 12/2009 | Hijlkema et al. |
| 7,641,687 B2 | 1/2010 | Chinn et al. |
| 7,674,282 B2 | 3/2010 | Wu et al. |

(56) References Cited

U.S. PATENT DOCUMENTS

| | | |
|---|---|---|
| 7,712,606 B2 | 5/2010 | Salahieh et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,763,065 B2 | 7/2010 | Schmid et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 * | 11/2010 | Salahieh et al. ............. 623/2.11 |
| 7,824,443 B2 * | 11/2010 | Salahieh et al. ............. 623/2.11 |
| 7,833,262 B2 | 11/2010 | McGuckin, Jr. et al. |
| 7,846,204 B2 | 12/2010 | Letac et al. |
| 7,857,845 B2 | 12/2010 | Stacchino et al. |
| 7,892,292 B2 | 2/2011 | Stack et al. |
| 7,914,574 B2 | 3/2011 | Schmid et al. |
| 7,918,880 B2 | 4/2011 | Austin |
| 7,927,363 B2 | 4/2011 | Perouse |
| 7,938,851 B2 | 5/2011 | Olson et al. |
| 7,947,071 B2 | 5/2011 | Schmid et al. |
| 7,959,666 B2 * | 6/2011 | Salahieh et al. ............. 623/1.26 |
| 7,959,672 B2 | 6/2011 | Salahieh et al. |
| 7,967,853 B2 | 6/2011 | Eidenschink et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,167,894 B2 | 5/2012 | Miles et al. |
| 8,172,896 B2 | 5/2012 | McNamara et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,277,500 B2 | 10/2012 | Schmid et al. |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 * | 12/2012 | Paul et al. .................... 623/2.11 |
| 8,343,213 B2 | 1/2013 | Salahieh et al. |
| 8,348,999 B2 | 1/2013 | Kheradvar et al. |
| 8,366,767 B2 | 2/2013 | Zhang |
| 8,376,865 B2 | 2/2013 | Forster et al. |
| 8,377,117 B2 | 2/2013 | Keidar et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,512,394 B2 | 8/2013 | Schmid et al. |
| 8,523,936 B2 | 9/2013 | Schmid et al. |
| 8,540,762 B2 | 9/2013 | Schmid et al. |
| 8,545,547 B2 | 10/2013 | Schmid et al. |
| 8,579,962 B2 | 11/2013 | Salahieh et al. |
| 8,603,160 B2 | 12/2013 | Salahieh et al. |
| 8,617,235 B2 | 12/2013 | Schmid et al. |
| 8,617,236 B2 * | 12/2013 | Paul et al. .................... 623/2.11 |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,685,077 B2 * | 4/2014 | Laske et al. .................. 623/1.11 |
| 8,828,078 B2 | 9/2014 | Salahieh et al. |
| 8,840,662 B2 * | 9/2014 | Salahieh et al. ............. 623/2.11 |
| 8,840,663 B2 | 9/2014 | Salahieh et al. |
| 8,851,286 B2 * | 10/2014 | Chang et al. .................. 206/464 |
| 8,852,272 B2 * | 10/2014 | Gross et al. .................. 623/2.18 |
| 8,858,620 B2 * | 10/2014 | Salahieh et al. ............. 623/2.11 |
| 8,894,703 B2 * | 11/2014 | Salahieh et al. ............. 623/2.11 |
| 8,940,014 B2 * | 1/2015 | Gamarra et al. ............. 606/207 |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 * | 10/2003 | Weldon et al. ............... 623/1.12 |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |

(56) References Cited

U.S. PATENT DOCUMENTS

| | | |
|---|---|---|
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0019374 A1 | 1/2004 | Hojeibane et al. |
| 2004/0034411 A1* | 2/2004 | Quijano et al. ............... 623/2.11 |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1* | 6/2005 | Haug et al. ................... 623/2.11 |
| 2005/0137693 A1* | 6/2005 | Haug et al. ................... 623/2.11 |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1* | 6/2005 | Salahieh et al. ............. 623/2.11 |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |

(56) References Cited

U.S. PATENT DOCUMENTS

| | | | |
|---|---|---|---|
| 2006/0173524 A1* | 8/2006 | Salahieh et al. | 623/1.11 |
| 2006/0195183 A1 | 8/2006 | Navia et al. | |
| 2006/0253191 A1 | 11/2006 | Salahieh et al. | |
| 2006/0259134 A1 | 11/2006 | Schwammenthal et al. | |
| 2006/0271166 A1 | 11/2006 | Thill et al. | |
| 2006/0287668 A1 | 12/2006 | Fawzi et al. | |
| 2006/0287717 A1 | 12/2006 | Rowe et al. | |
| 2007/0010876 A1 | 1/2007 | Salahieh et al. | |
| 2007/0010877 A1 | 1/2007 | Salahieh et al. | |
| 2007/0016286 A1 | 1/2007 | Herrmann et al. | |
| 2007/0055340 A1 | 3/2007 | Pryor | |
| 2007/0061008 A1 | 3/2007 | Salahieh et al. | |
| 2007/0088431 A1 | 4/2007 | Bourang et al. | |
| 2007/0100427 A1 | 5/2007 | Perouse | |
| 2007/0112355 A1* | 5/2007 | Salahieh et al. | 606/108 |
| 2007/0118214 A1* | 5/2007 | Salahieh et al. | 623/2.22 |
| 2007/0162107 A1 | 7/2007 | Haug et al. | |
| 2007/0173918 A1 | 7/2007 | Dreher et al. | |
| 2007/0203503 A1* | 8/2007 | Salahieh et al. | 606/108 |
| 2007/0244552 A1 | 10/2007 | Salahieh et al. | |
| 2007/0288089 A1 | 12/2007 | Gurskis et al. | |
| 2008/0009940 A1 | 1/2008 | Cribier | |
| 2008/0033541 A1 | 2/2008 | Gelbart et al. | |
| 2008/0071363 A1 | 3/2008 | Tuval et al. | |
| 2008/0082165 A1 | 4/2008 | Wilson et al. | |
| 2008/0125859 A1 | 5/2008 | Salahieh et al. | |
| 2008/0188928 A1* | 8/2008 | Salahieh et al. | 623/2.11 |
| 2008/0208328 A1 | 8/2008 | Antocci et al. | |
| 2008/0208332 A1 | 8/2008 | Lamphere et al. | |
| 2008/0221672 A1 | 9/2008 | Lamphere et al. | |
| 2008/0234814 A1 | 9/2008 | Salahieh et al. | |
| 2008/0255661 A1 | 10/2008 | Straubinger et al. | |
| 2008/0269878 A1 | 10/2008 | Iobbi | |
| 2008/0288054 A1 | 11/2008 | Pulnev et al. | |
| 2009/0005863 A1 | 1/2009 | Goetz et al. | |
| 2009/0030512 A1 | 1/2009 | Thielen et al. | |
| 2009/0054969 A1 | 2/2009 | Salahieh et al. | |
| 2009/0076598 A1 | 3/2009 | Salahieh et al. | |
| 2009/0093877 A1 | 4/2009 | Keidar et al. | |
| 2009/0171456 A1 | 7/2009 | Kveen et al. | |
| 2009/0216312 A1 | 8/2009 | Straubinger et al. | |
| 2009/0222076 A1 | 9/2009 | Figulla et al. | |
| 2009/0264759 A1 | 10/2009 | Byrd | |
| 2009/0264997 A1 | 10/2009 | Salahieh et al. | |
| 2009/0299462 A1 | 12/2009 | Fawzi et al. | |
| 2010/0036479 A1 | 2/2010 | Hill et al. | |
| 2010/0049313 A1 | 2/2010 | Alon et al. | |
| 2010/0082089 A1 | 4/2010 | Quadri et al. | |
| 2010/0094399 A1 | 4/2010 | Dorn et al. | |
| 2010/0121434 A1 | 5/2010 | Paul et al. | |
| 2010/0161045 A1 | 6/2010 | Righini | |
| 2010/0185275 A1 | 7/2010 | Richter et al. | |
| 2010/0191320 A1 | 7/2010 | Straubinger et al. | |
| 2010/0191326 A1 | 7/2010 | Alkhatib | |
| 2010/0219092 A1 | 9/2010 | Salahieh et al. | |
| 2010/0249908 A1 | 9/2010 | Chau et al. | |
| 2010/0268332 A1 | 10/2010 | Tuval et al. | |
| 2010/0280495 A1 | 11/2010 | Paul et al. | |
| 2010/0298931 A1 | 11/2010 | Quadri et al. | |
| 2011/0040366 A1 | 2/2011 | Goetz et al. | |
| 2011/0098805 A1 | 4/2011 | Dwork et al. | |
| 2011/0257735 A1 | 10/2011 | Salahieh et al. | |
| 2011/0264191 A1 | 10/2011 | Rothstein | |
| 2011/0264196 A1 | 10/2011 | Savage et al. | |
| 2011/0264203 A1 | 10/2011 | Dwork et al. | |
| 2011/0288634 A1 | 11/2011 | Tuval et al. | |
| 2011/0295363 A1 | 12/2011 | Girard et al. | |
| 2011/0319989 A1 | 12/2011 | Lane et al. | |
| 2012/0022633 A1 | 1/2012 | Olson et al. | |
| 2012/0022642 A1 | 1/2012 | Haug et al. | |
| 2012/0029627 A1 | 2/2012 | Salahieh et al. | |
| 2012/0041550 A1* | 2/2012 | Salahieh et al. | 623/2.36 |
| 2012/0053683 A1* | 3/2012 | Salahieh et al. | 623/2.11 |
| 2012/0089224 A1 | 4/2012 | Haug et al. | |
| 2012/0179244 A1 | 7/2012 | Schankereli et al. | |
| 2012/0303113 A1 | 11/2012 | Benichou et al. | |
| 2012/0303116 A1 | 11/2012 | Gorman et al. | |
| 2012/0305441 A1* | 12/2012 | Murray et al. | 206/570 |
| 2012/0310332 A1* | 12/2012 | Murray et al. | 623/2.11 |
| 2012/0330409 A1 | 12/2012 | Haug et al. | |
| 2013/0018457 A1 | 1/2013 | Gregg et al. | |
| 2013/0030520 A1 | 1/2013 | Lee et al. | |
| 2013/0079867 A1 | 3/2013 | Hoffman et al. | |
| 2013/0079869 A1 | 3/2013 | Straubinger et al. | |
| 2013/0096664 A1 | 4/2013 | Goetz et al. | |
| 2013/0123757 A1* | 5/2013 | Crisostomo et al. | 606/1 |
| 2013/0123898 A1* | 5/2013 | Tung et al. | 623/1.11 |
| 2013/0138207 A1 | 5/2013 | Quadri et al. | |
| 2013/0158656 A1 | 6/2013 | Sutton | |
| 2013/0166017 A1 | 6/2013 | Cartledge et al. | |
| 2013/0184813 A1 | 7/2013 | Quadri et al. | |
| 2013/0190865 A1 | 7/2013 | Anderson | |
| 2013/0253640 A1 | 9/2013 | Meiri et al. | |
| 2013/0289698 A1 | 10/2013 | Wang et al. | |
| 2013/0296999 A1 | 11/2013 | Burriesci et al. | |
| 2013/0304199 A1 | 11/2013 | Sutton et al. | |
| 2013/0310917 A1 | 11/2013 | Richter et al. | |
| 2013/0310923 A1 | 11/2013 | Kheradvar et al. | |
| 2014/0018911 A1 | 1/2014 | Zhou et al. | |
| 2014/0094904 A1 | 4/2014 | Salahieh et al. | |
| 2014/0114405 A1* | 4/2014 | Paul et al. | 623/2.11 |
| 2014/0114406 A1 | 4/2014 | Salahieh et al. | |
| 2014/0121766 A1 | 5/2014 | Salahieh et al. | |
| 2014/0135912 A1* | 5/2014 | Salahieh et al. | 623/2.18 |
| 2014/0243967 A1 | 8/2014 | Salahieh et al. | |
| 2015/0012085 A1 | 1/2015 | Salahieh et al. | |
| 2015/0073540 A1* | 3/2015 | Salahieh et al. | 623/2.11 |
| 2015/0073541 A1 | 3/2015 | Salahieh et al. | |

FOREIGN PATENT DOCUMENTS

| | | |
|---|---|---|
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049814 | 4/2002 |
| DE | 10049815 | 4/2002 |
| EP | 0103546 | 5/1988 |
| EP | 0144167 | 11/1989 |
| EP | 0409929 | 4/1997 |
| EP | 0850607 | 7/1998 |
| EP | 0597967 | 12/1999 |
| EP | 1000590 | 5/2000 |
| EP | 1057459 | 12/2000 |
| EP | 1057460 | 12/2000 |
| EP | 1078610 | 2/2001 |
| EP | 1088529 | 4/2001 |
| EP | 0937439 | 9/2003 |
| EP | 1340473 | 2/2004 |
| EP | 1356793 | 3/2004 |
| EP | 1042045 | 5/2004 |
| EP | 0819013 | 6/2004 |
| EP | 1435879 | 7/2004 |
| EP | 1439800 | 7/2004 |
| EP | 1469797 | 10/2004 |
| EP | 1472996 | 11/2004 |
| EP | 1229864 | 4/2005 |
| EP | 1430853 | 6/2005 |
| EP | 1059894 | 7/2005 |
| EP | 1551274 | 7/2005 |
| EP | 1551336 | 7/2005 |
| EP | 1562515 | 8/2005 |
| EP | 1570809 | 9/2005 |
| EP | 1576937 | 9/2005 |
| EP | 1582178 | 10/2005 |
| EP | 1582179 | 10/2005 |
| EP | 1589902 | 11/2005 |
| EP | 1600121 | 11/2005 |
| EP | 1156757 | 12/2005 |
| EP | 1616531 | 1/2006 |
| EP | 1690515 | 8/2006 |
| EP | 1605871 | 7/2008 |
| EP | 2047824 | 5/2012 |

(56) References Cited

FOREIGN PATENT DOCUMENTS

| | | |
|---|---|---|
| FR | 2788217 | 7/2000 |
| GB | 2056023 | 3/1981 |
| GB | 2398245 | 8/2004 |
| SU | 1271508 | 11/1986 |
| SU | 1371700 | 2/1988 |
| WO | 9117720 | 11/1991 |
| WO | 9217118 | 10/1992 |
| WO | 9301768 | 2/1993 |
| WO | 9315693 | 8/1993 |
| WO | 9504556 | 2/1995 |
| WO | 9529640 | 11/1995 |
| WO | 9614032 | 5/1996 |
| WO | 9624306 | 8/1996 |
| WO | 9640012 | 12/1996 |
| WO | 9829057 | 7/1998 |
| WO | 9836790 | 8/1998 |
| WO | 9850103 | 11/1998 |
| WO | 9857599 | 12/1998 |
| WO | 9933414 | 7/1999 |
| WO | 9940964 | 8/1999 |
| WO | 9944542 | 9/1999 |
| WO | 9947075 | 9/1999 |
| WO | 0009059 | 2/2000 |
| WO | 0041652 | 7/2000 |
| WO | 0044308 | 8/2000 |
| WO | 0044311 | 8/2000 |
| WO | 0044313 | 8/2000 |
| WO | 0045874 | 8/2000 |
| WO | 0047139 | 8/2000 |
| WO | 0049970 | 8/2000 |
| WO | 0067661 | 11/2000 |
| WO | 0105331 | 1/2001 |
| WO | 0108596 | 2/2001 |
| WO | 0110320 | 2/2001 |
| WO | 0110343 | 2/2001 |
| WO | 0135870 | 5/2001 |
| WO | 0149213 | 7/2001 |
| WO | 0154625 | 8/2001 |
| WO | 0162189 | 8/2001 |
| WO | 0164137 | 9/2001 |
| WO | 0176510 | 10/2001 |
| WO | 0197715 | 12/2001 |
| WO | 0236048 | 5/2002 |
| WO | 0241789 | 5/2002 |
| WO | 0243620 | 6/2002 |
| WO | 0247575 | 6/2002 |
| WO | 02056955 | 7/2002 |
| WO | 02100297 | 12/2002 |
| WO | 03003943 | 1/2003 |
| WO | 03003949 | 1/2003 |
| WO | 03011195 | 2/2003 |
| WO | 03015851 | 2/2003 |
| WO | 03030776 | 4/2003 |
| WO | 03047648 | 6/2003 |
| WO | 03094793 | 11/2003 |
| WO | 03094797 | 11/2003 |
| WO | 2004006803 | 1/2004 |
| WO | 2004006804 | 1/2004 |
| WO | 2004014256 | 2/2004 |
| WO | 2004019811 | 3/2004 |
| WO | 2004019817 | 3/2004 |
| WO | 2004021922 | 3/2004 |
| WO | 2004023980 | 3/2004 |
| WO | 2004026117 | 4/2004 |
| WO | 2004041126 | 5/2004 |
| WO | 2004043293 | 5/2004 |
| WO | 2004047681 | 6/2004 |
| WO | 2004058106 | 7/2004 |
| WO | 2004066876 | 8/2004 |
| WO | 2004082536 | 9/2004 |
| WO | 2004089250 | 10/2004 |
| WO | 2004089253 | 10/2004 |
| WO | 2004093728 | 11/2004 |
| WO | 2004105651 | 12/2004 |
| WO | 2005002466 | 1/2005 |
| WO | 2005004753 | 1/2005 |
| WO | 2005009285 | 2/2005 |
| WO | 2005011534 | 2/2005 |
| WO | 2005011535 | 2/2005 |
| WO | 2005023155 | 3/2005 |
| WO | 2005027790 | 3/2005 |
| WO | 2005046528 | 5/2005 |
| WO | 2005046529 | 5/2005 |
| WO | 2005048883 | 6/2005 |
| WO | 2005062980 | 7/2005 |
| WO | 2005065585 | 7/2005 |
| WO | 2005084595 | 9/2005 |
| WO | 2005087140 | 9/2005 |
| WO | 2005096993 | 10/2005 |
| WO | 2006005015 | 1/2006 |
| WO | 2006009690 | 1/2006 |
| WO | 2006027499 | 3/2006 |
| WO | 2006093795 | 9/2006 |
| WO | 2006138391 | 12/2006 |
| WO | 2007009117 | 1/2007 |
| WO | 2007033093 | 3/2007 |
| WO | 2007035471 | 3/2007 |
| WO | 2007044285 | 4/2007 |
| WO | 2007053243 | 5/2007 |
| WO | 2007058847 | 5/2007 |
| WO | 2007092354 | 8/2007 |
| WO | 2007097983 | 8/2007 |
| WO | 2008028569 | 3/2008 |
| WO | 2008035337 | 3/2008 |
| WO | 2010042950 | 4/2010 |
| WO | 2010098857 | 9/2010 |

OTHER PUBLICATIONS

Andersen, H.R. et al., "Transluminal implantation of artificial heart valves. Description of a new expandable aortic valve and initial results with implantation by catheter technique in closed chest pigs". European Heart Journal (1992) 13, 704-708.

Atwood, A. et al., "Insertion of Heart Valves by Catheterization". Project supervised by Professor Sinan Muftu of Northeastern University (2001-2002) 36-40.

Atwood, A. et al., "Insertion of Heart Valves by Catheterization". The Capstone Design Course Report. MIME 1501-1502. Technical Design Report. Northeastern University. Nov. 5, 2007, pp. 1-93.

Bodnar, E. et al., Replacement Cardiac Valves, Chapter 13, Pergamon Publishing Corporation, New York (1991) 307-332.

Boudjemline, Y. et al., "Percutaneous implantation of a valve in the descending aorta in lambs". Euro. Heart J. (Jul. 2002),23:13,1045-1049.

Boudjemline, Y. et al., "Percutaneous pulmonary valve replacement in a large right ventricular outflow tract: an experimental study". Journal of the American College of Cardiology, (Mar. 17, 2004),Vo. 43, No. 6, pp. 1082-1087.

Boudjemline, Y. et al., "Percutaneous valve insertion: A new approach?" J. of Thoracic and Cardio. Surg. (2003) 125:3, 741-743.

Boudjemline, Y. et al., "Steps Toward Percutaneous Aortic Valve Replacement" Circulation, Feb. 12, 2002; 105:775-778.

Boudjemline,Y. et al., "Percutaneous Implantation of a Biological Valve in the Aorta to Treat aortic Valve Insufficiency—A Sheep Study," Med. Sci. Monit (2002) vol. 8, No. 4, pp. BR113-BR116.

Aug. 19, 2011, Supplemental Search Report from EP Patent office, EP Application No. 04813777.2.

Cribier, A., et al., "Early Experience with Percutaneous Transcatherter Implantation of Heart Vavle Prosthesis for the Treatment of End-Stage Inoperable Patients with Calcific Aortic Stenonis". J. or Am. Coll. of Cardio (Feb. 18, 2004) 43,698-703.

Cribier, A., et al., "Percutaneous Transcatheter Implantation of an Aortic Valve Prosthesis for Calcific Aortic Stenosis: First Human Case" Percutaneous Valve Technologies, Inc. (2002) 16 pages.

Cribier, A., et al., "Percutaneous Transcatheter Implantation of an Aortic Valve Prosthesis for Calcific Aortic Stenosis: First Human Case Description" Circulation (Dec. 10, 2002) 3006-3008.

Cunanan, Crystal, M., et al., "Tissue Characterization and Calcification Potential of Commerical Bioprosthetic Heart Valves", Ann Thorac Surg, 2001, 71:S417-21.

(56) References Cited

OTHER PUBLICATIONS

Cunliffe, H.R. et al., "Glutaraldehyde Inactivation of Exotic Animal Viruses in Swine Heart Tissue", May 1979, 1044-1046, vol. 37, No. 5., Applied and Environmental Microbiology, Greenport, New York.
EP Search Report mailed Aug. 10, 2011 for EP Application No. 06824992.9.
Examiner's First Report on AU Patent Application No. 2011202667, issued on May 17, 2012.
Ferrari,M.et al., "Percutaneous transvascular aortic valve replacement with self expanding stent-valve device." Poster from the perdetation given at SMIT 2000, 12th International Conference (Sep. 5, 2000).
Heart Valve Materials—Bovine (cow), Equine & Porcine Pericardium, Maverick Biosciences PTY. LTD, 2009, http://www.maverickbio.com/biological-medical-device-materials.php?htm.
Helmus, M.N., "Mechanical and bioprosthetic heart valves in biomaterials for artificial organs", 113-162, Woodhead Publishing Limited, 2011.
Hijazi, Z.M., "Transcatheter Valve Replacement: A New Era of Percutaneous Cardiac Intervention Begins." J. of Am. College of Cardio (Nov. 6, 2004) 43:6, 1088-1089.
Hourihan, Maribeth, et al., "Transcatheter Umbrella Closure of Valvular and Paravalvular Leaks", Nov. 15, 1992, 1371-7, vol. 20, No. 6, JACC, Boston Massachusetts.
Huber C.H. et al., "Do valved stents compromise coronary flow?" European Journal of Cardio-thoracic Surgery, (2004), vol. 25, pp. 754-759.
Knudsen, L.L.et al., "Catheter-implanted prosthetic heart valves". International J. of Art. Organs. 1993; 16(5): 253-262.
Kort, S. et al., "Minimally invasive aortic valve replacement: Echocardiographic and clinical results" Am. Heart J. Sep. 2001;142(3): 476-481.
Laborde, J.C. et al., Percutaneous implantation of the corevalve aortic valve prosthesis for patients presenting high risk for surgical valve replacement, 2006, 1:472-474, EuroIntervention.
Levy, Charles, M.D., et al., Mycobacterium Chelonei Infection of Porcine Heart Valves, Sep. 22, 1977, vol. 297, No. 12, The New England Journal of Medicine. pp. 667-668.
Lutter, G. et al., "Percutaneous aortic valve replacement: An experimental study. I. Studies of implantation," J. Thoracic and Cardio. Surg. (Apr. 2002)123:4, 768-776.
Moulopoulos, S. et al., "Catheter-Mounted Aortic Valves" Annals of Thoracic Surg. (May 1971)11:5, 423-430.
Aug. 19, 2011, Supplemental Search Report from EP Patent office, EP Application No. 04815634.3.
Oct. 24, 2011, Supplemental Search Report from EP Patent office, EP Application No. 05758878.2.
Paniagua, D. et al., "Percutaneous heart valve in the chronic in vitro testing model" Circulation (Sep. 17, 2002) 106:e51-e52, American Heart Association, Inc.
Paniagua, D. et al., Heart Watch (2004), Spring, 2004 Edition: 8 pages, Texas Heart Institute.
Pavcnik, D. et al., "Percutaneous bioprosthetic venous valve: A long term study in sheep". J. of Vascular Surg. (Mar. 2002) 35:3, 598-603.
Pericardial Heart Valves, Edwards Lifesciences, Cardiovascular Surgery FAQ, visited on Nov. 14, 2010, http://www.edwards.com/products/cardiovascularsurgeryfaq.htm.
Phillips, S. J. et al., "A temporary Catheter-Tip Aortic Valve: Hemodynamic Effects on Experimental Acute Aortic Insufficiency". Annals of Thoracic Surg. (Feb. 1976) 21:2, 134-137.
Love, C. et al., The Autogenous Tissue Heart Valve: Current Status, Journal of Cardiac Surgery.(1991)6:4, 499-507.
Sochman, J. et al., "Percutaneous Transcatheter Aortic Disc Valve Prosthesis Implantation: A Feasibility Study".Cardiovasc. Intervent. Radiol (2000) 23, 384-388.
Southern Lights Biomaterials Homepage, visited on Jan. 7, 2011, http://www.slv.co.nz/.
Stassano, Paolo, et al., Mid-term results of the valve-on-valve technique for bioprosthetic failure, 2000, 18:453-457, European Journal of Cardio-thoracic Surgery.
Stuart, M., "In Heart Valves, A Brave , New, Non-Surgical World." Start-Up (Feb. 2004) 9-17.
Topol, Eric J., M.D., Percutaneous Expandable Prosthetic Valves, Textbook of Interventional Cardiology, 1994, 1268-1276, vol. 2, W.B. Saunders Company, Philadelphia.
Vahanian, A. et al., "Percutaneous Approaches to Valvular Disease." Circulation (Apr. 6, 2004) 109:1572-1579.
Van Herwerden, L.A. et al., "Percutaneous Valve Implantation: back to the furture?"Euro Heart J. (Sep. 2002) 23:18, 1415-1416.
Zhou, J. Q. et al., "Self-Expandable valved stent of large size: off-bypass implantation in pulmonary position". European Journal of Cardio-thoracic Surgery (2003) 24, 212-216.

* cited by examiner

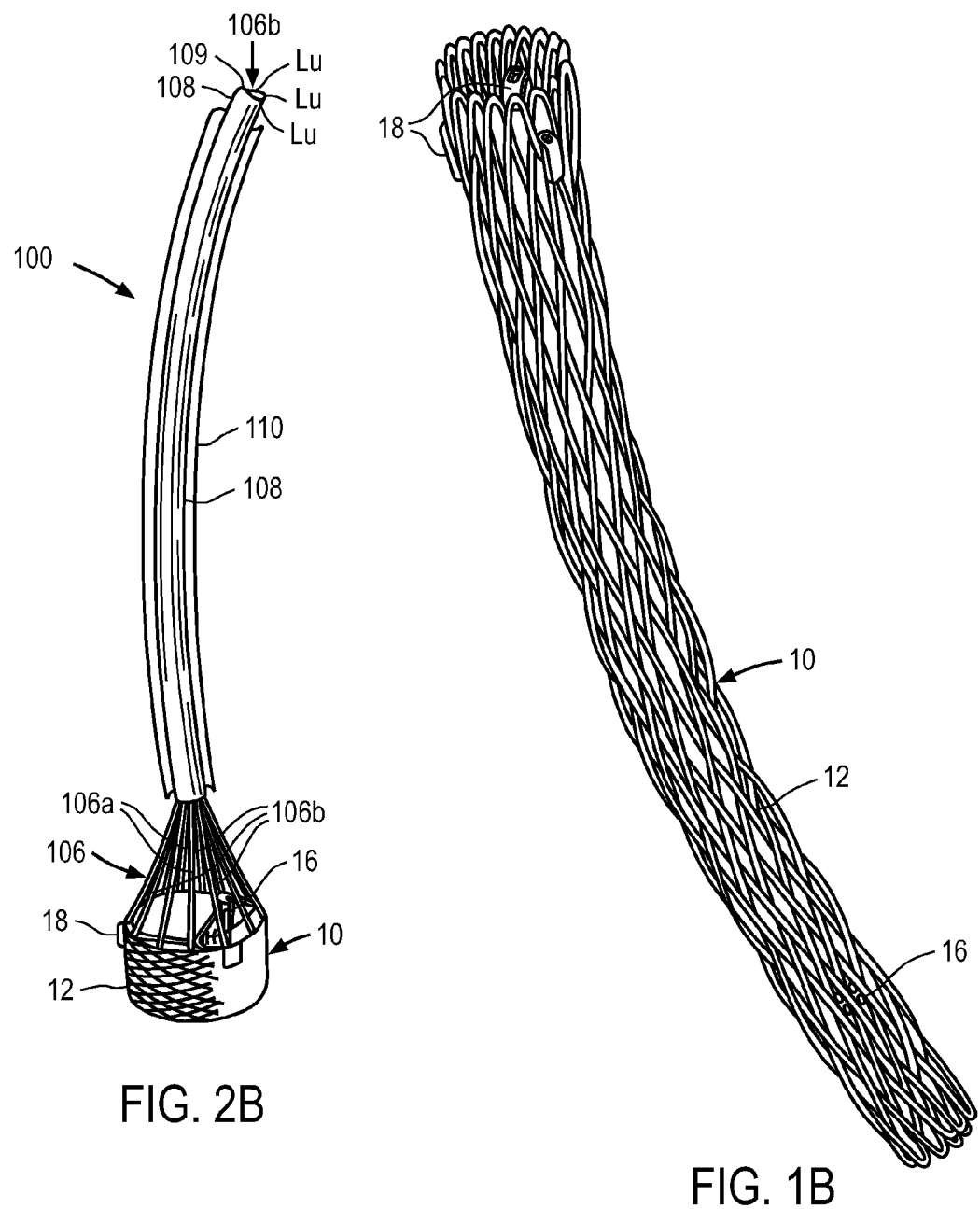

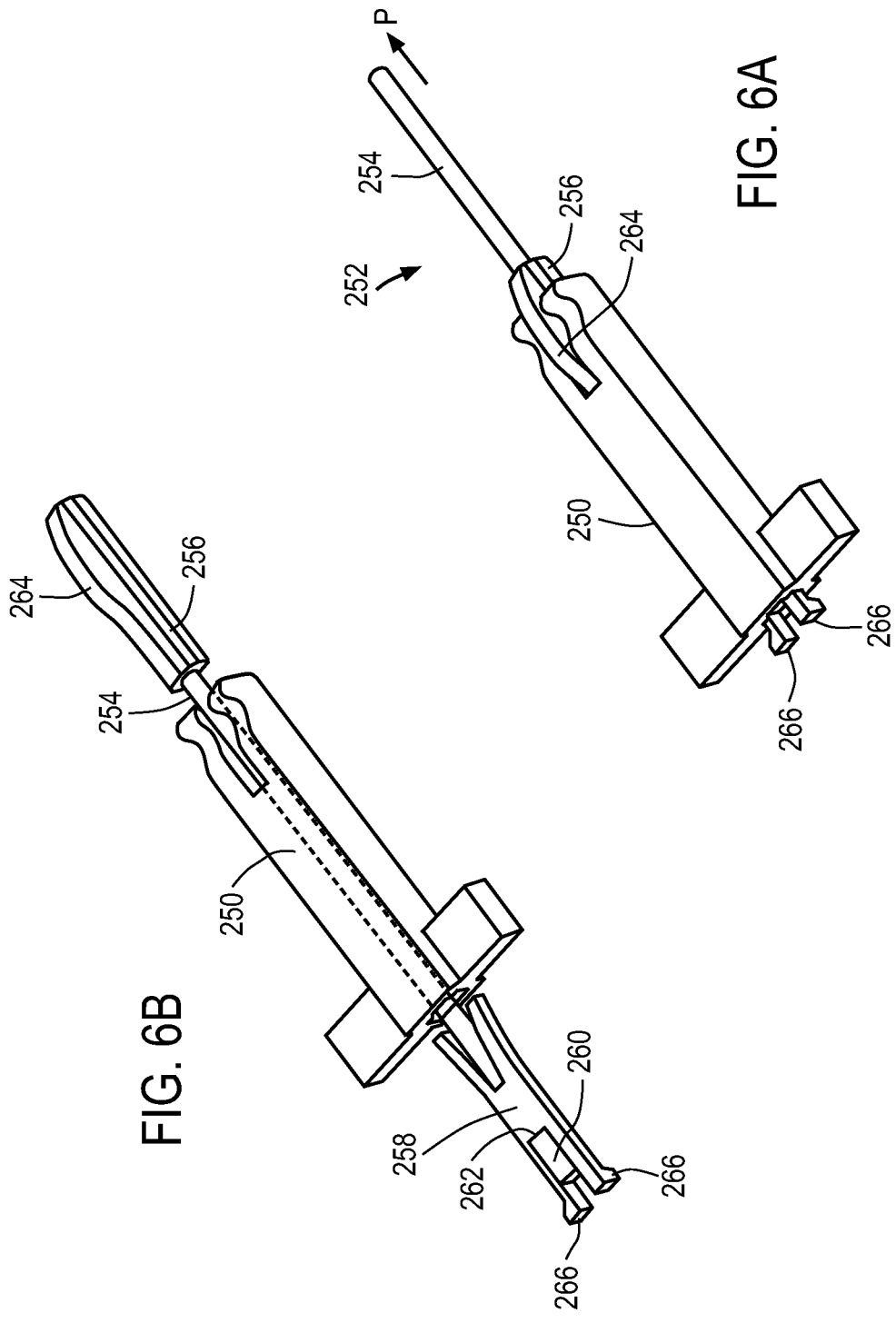

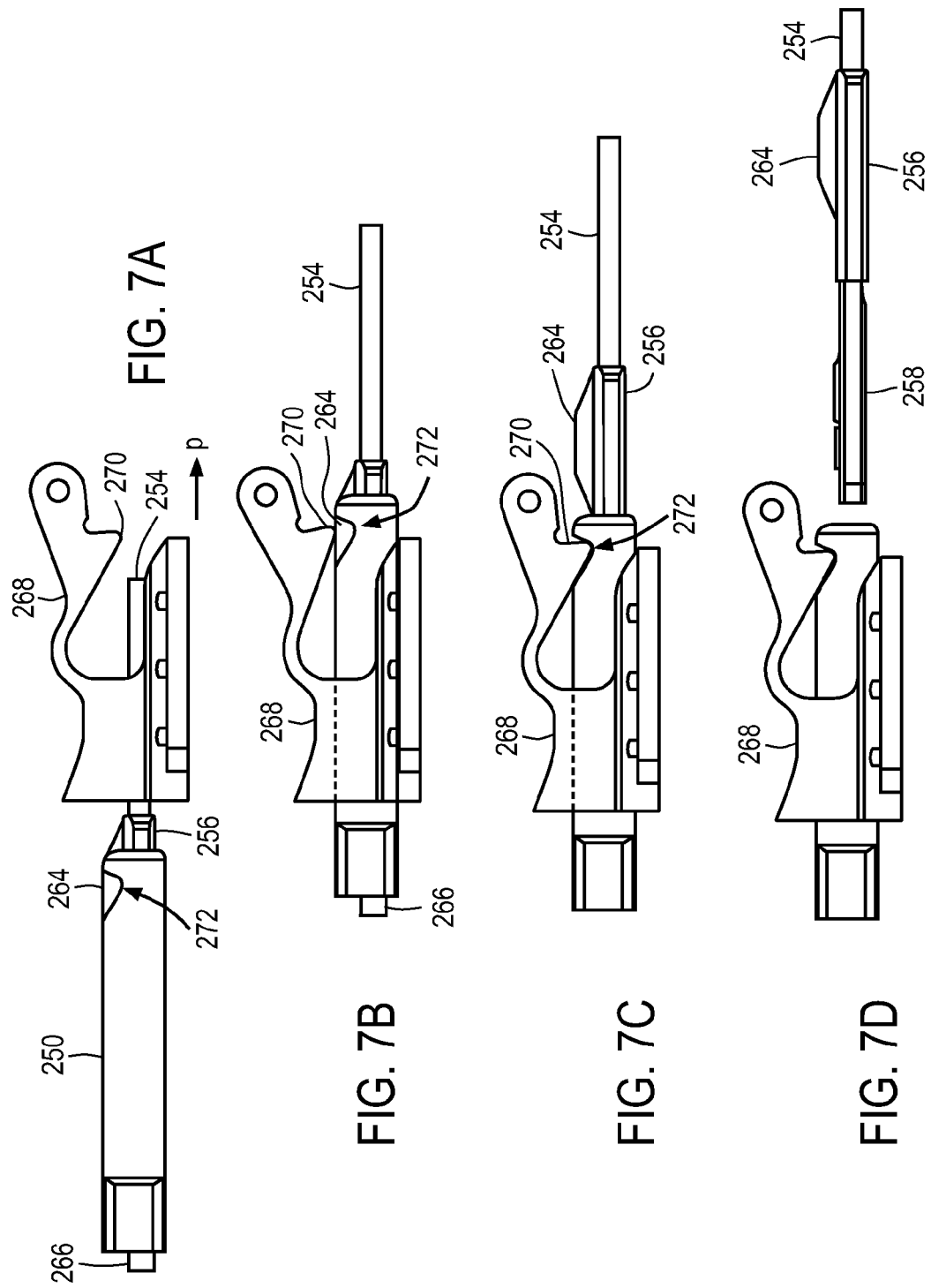

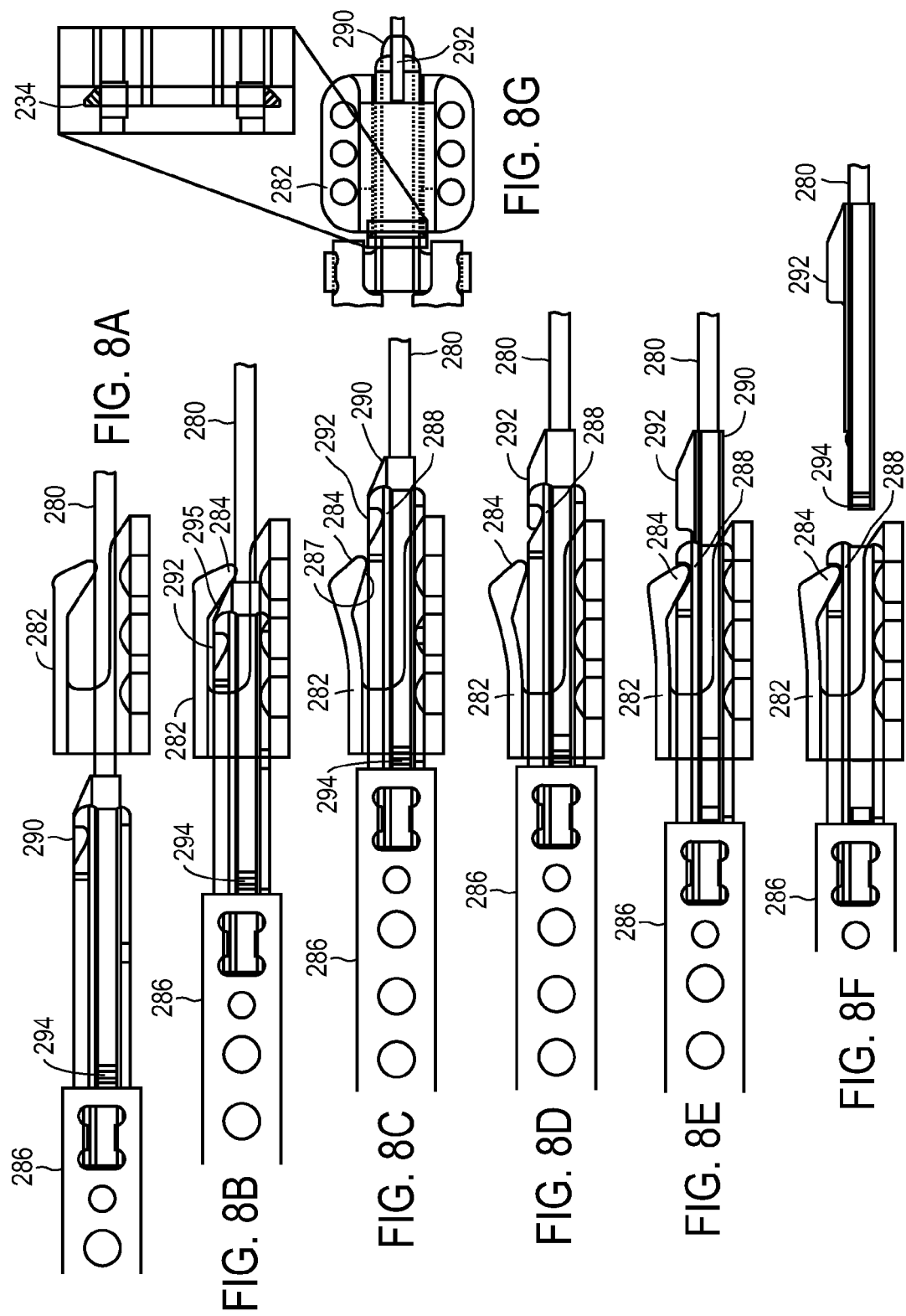

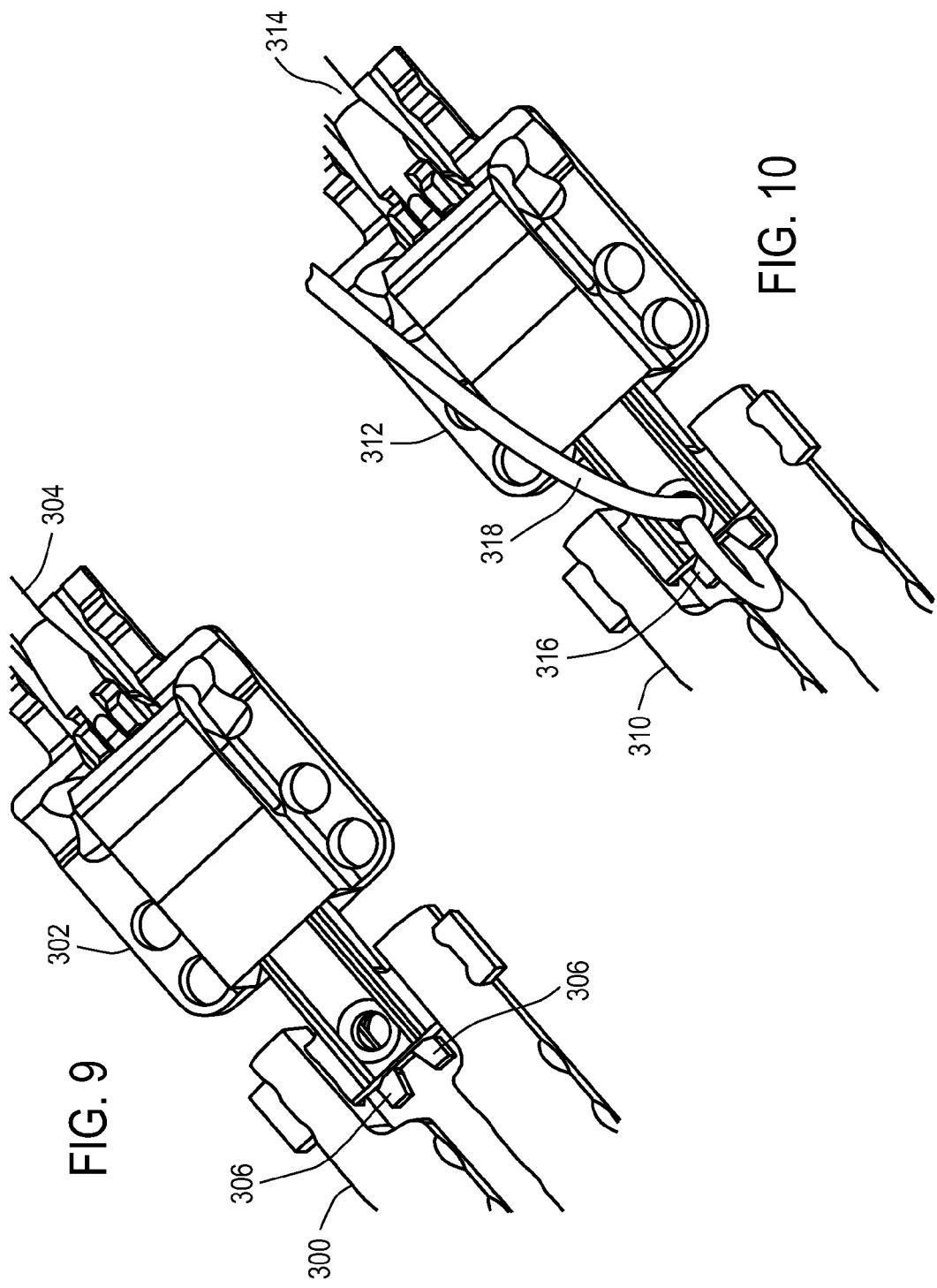

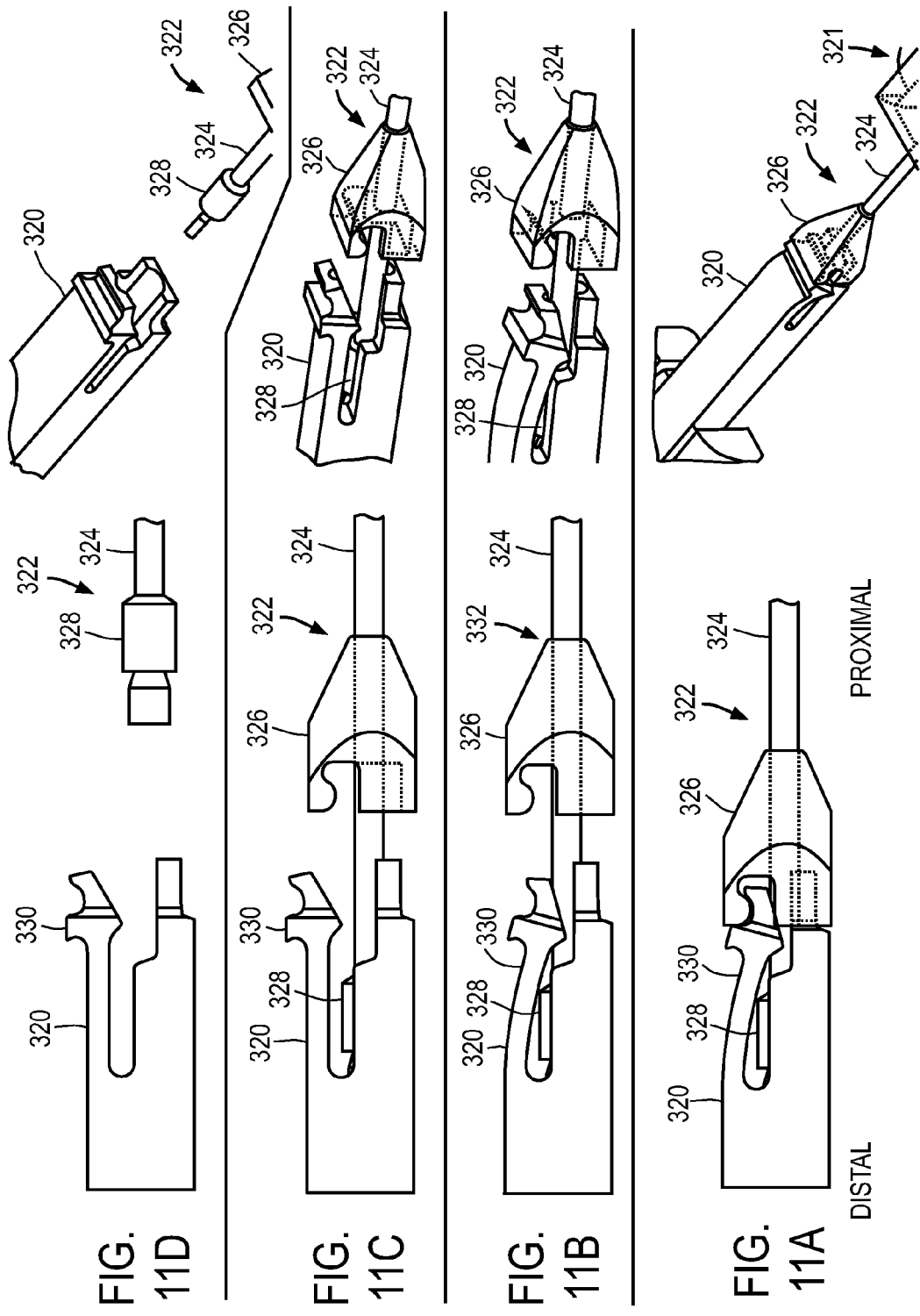

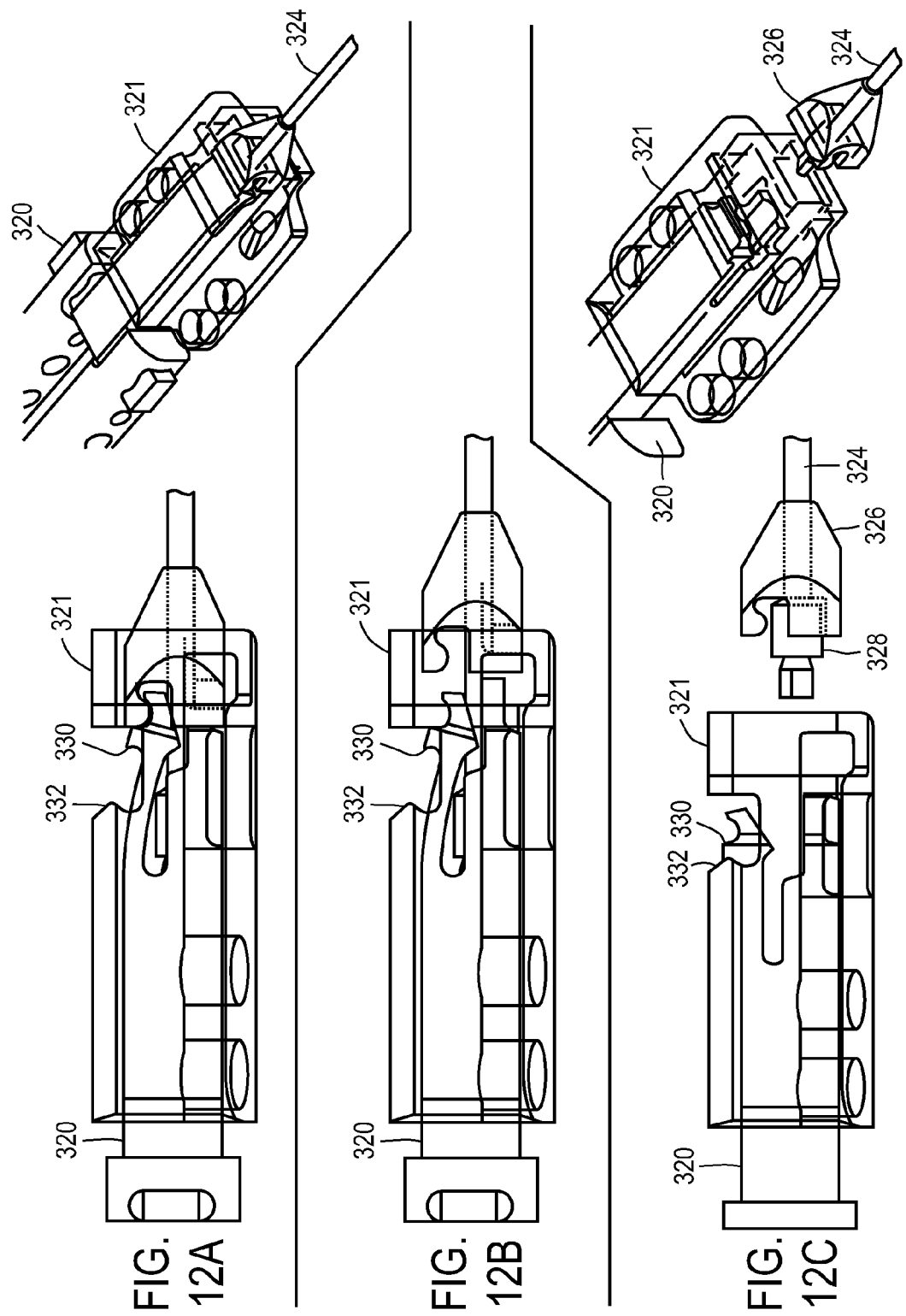

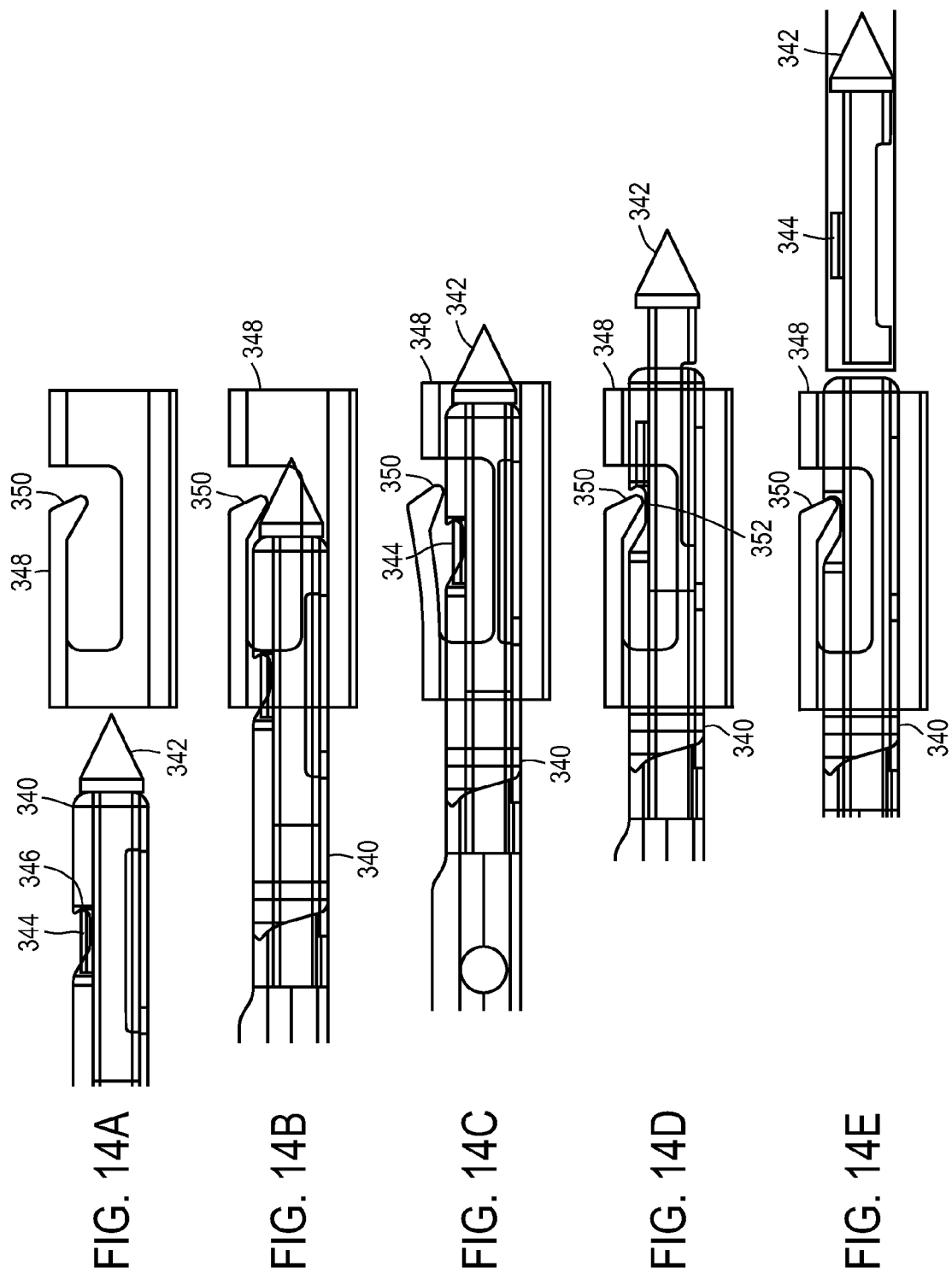

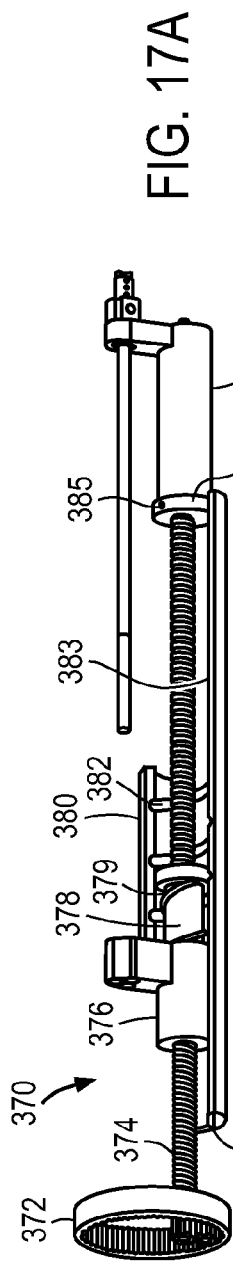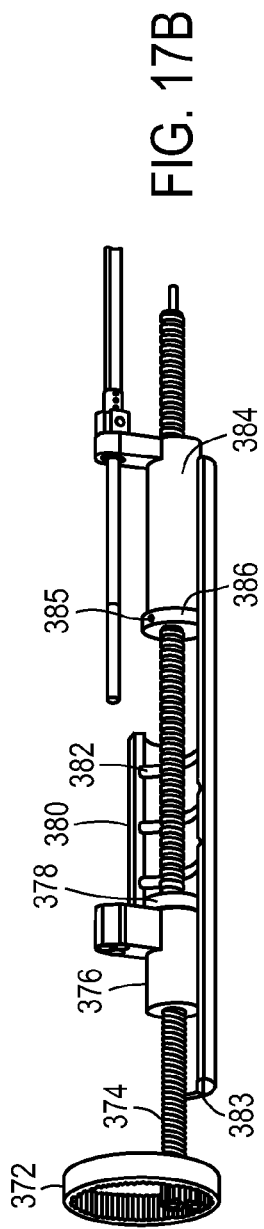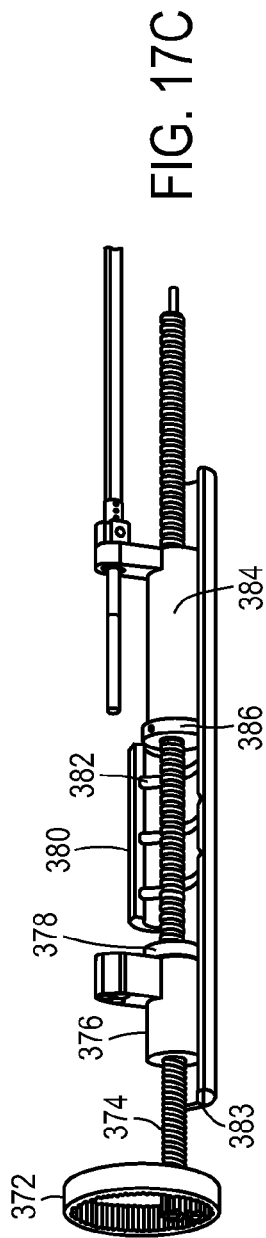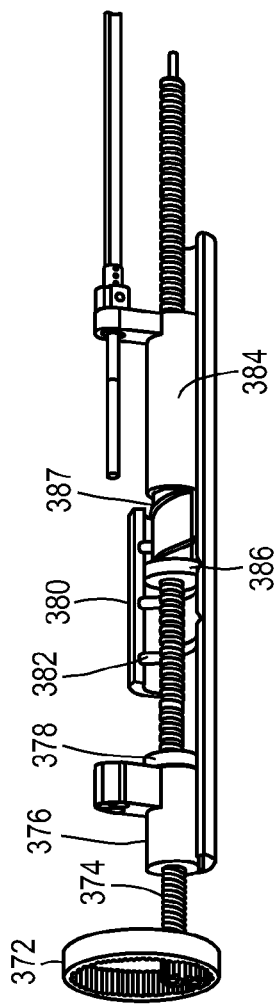

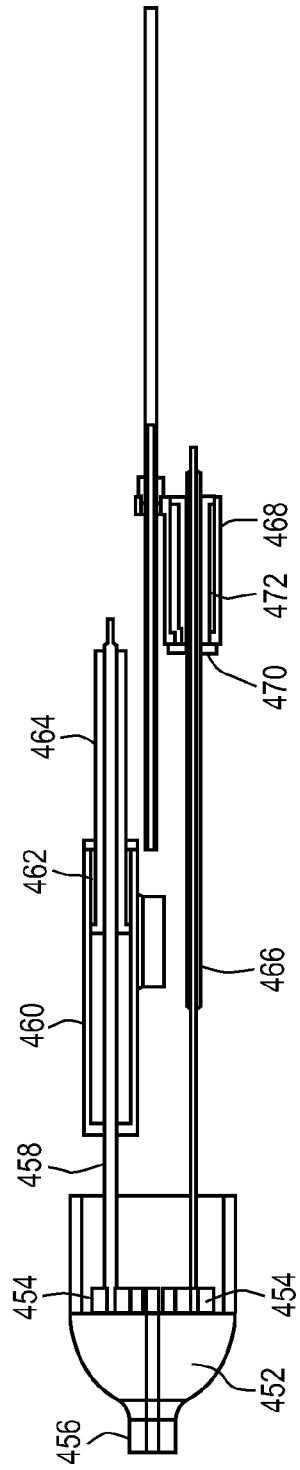
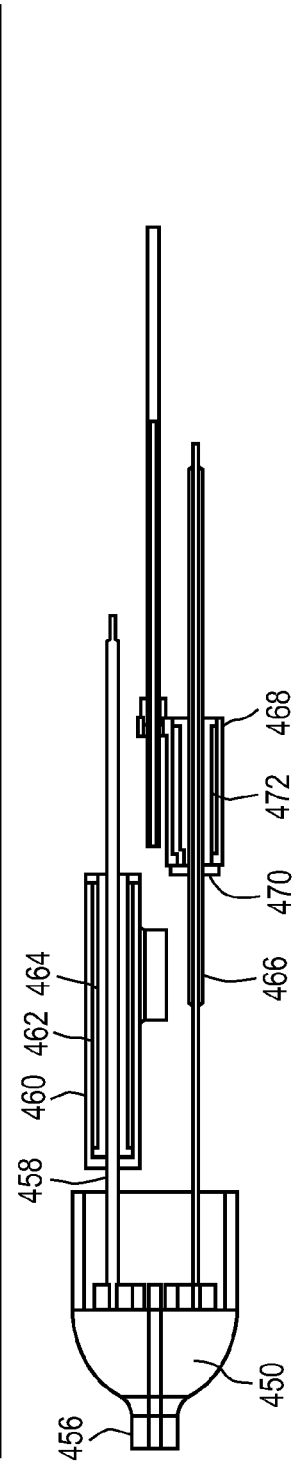
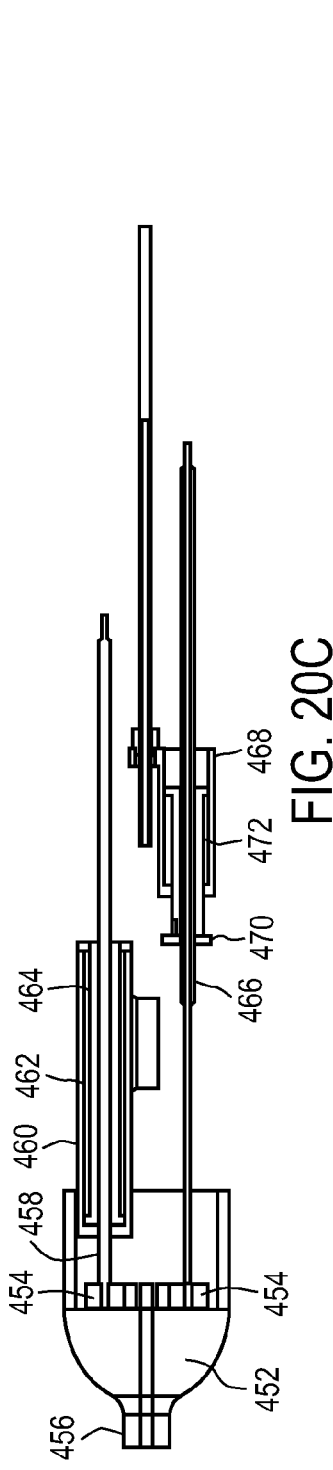

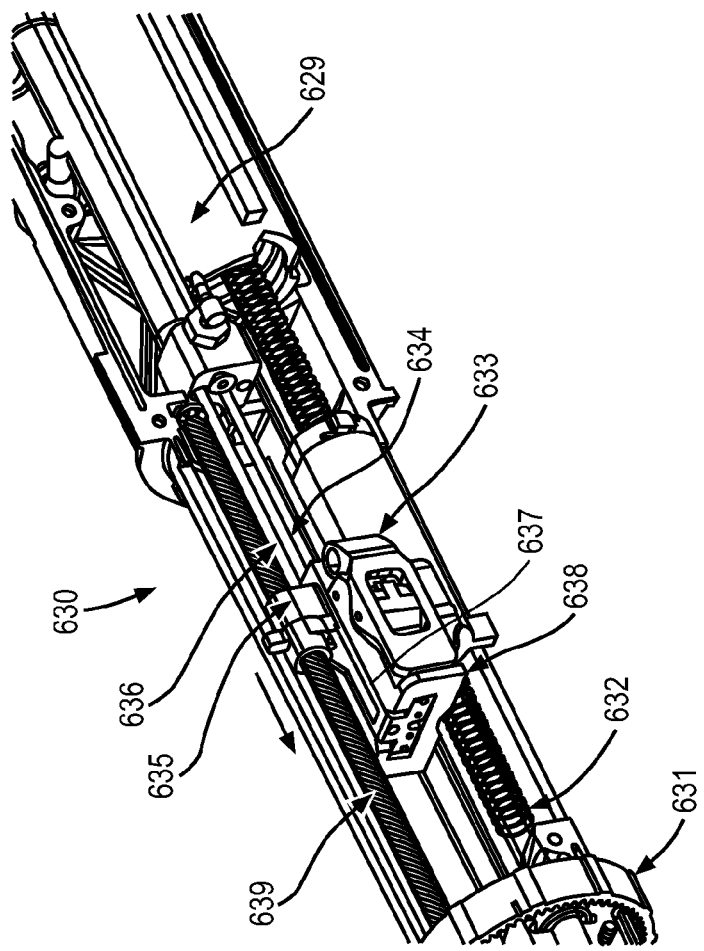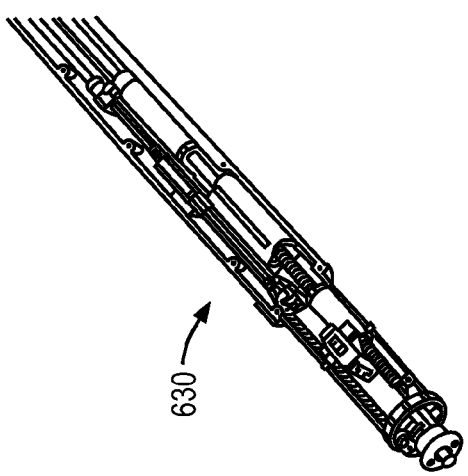
FIG. 23C

MEDICAL DEVICES AND DELIVERY SYSTEMS FOR DELIVERING MEDICAL DEVICES

CROSS-REFERENCE TO RELATED APPLICATIONS

This application is a divisional application of U.S. patent application Ser. No. 13/287,420, filed Nov. 2, 2011, which is a divisional application of application Ser. No. 12/578,463, filed Oct. 13, 2009, which is a continuation-in-part application of application Ser. No. 10/982,388, filed Nov. 5, 2004, now issued U.S. Pat. No. 7,959,666; and also a continuation-in-part application of application Ser. No. 11/275,912, filed Feb. 2, 2006, now issued U.S. Pat. No. 7,824,443; which applications are incorporated by reference herein, each in its entirety, and to which applications we claim priority under 35 U.S.C. §120.

This application claims the benefit under 35 U.S.C. §119 of U.S. Provisional Patent Application Nos. 61/104,509, filed Oct. 10, 2008; and 61/151,814, filed Feb. 11, 2009; which applications are incorporated by reference, each in its entirety.

This application is related to the following patent applications, all of which are incorporated by reference herein: U.S. patent application Ser. No. 10/746,240, filed Dec. 23, 2003 (U.S. Patent Publication No. 2005/1237687); U.S. patent application Ser. No. 10/972,287, filed Oct. 21, 2004 (U.S. Pat. No. 7,748,389); U.S. patent application Ser. No. 10/982,692, filed Nov. 5, 2004 (U.S. Pat. No. 7,824,442); U.S. patent application Ser. No. 11/706,549, filed Feb. 14, 2007 (U.S. Pat. No. 7,988,724); U.S. Provisional Patent Application No. 61/104,509, filed Oct. 10, 2008; U.S. patent application Ser. No. 11/274,889, filed Nov. 14, 2005 (U.S. Patent Publication No. 2007/0112355); U.S. patent application Ser. No. 10/870,340, filed Jun. 16, 2004 (U.S. Pat. No. 7,780,725); and U.S. patent application Ser. No. 11/314,969, filed Dec. 20, 2005 (U.S. Patent Publication No. 2007/0118214).

BACKGROUND OF THE INVENTION

Implantable medical devices can be delivered to a target location within a patient and implanted therein. For example, endoluminal delivery techniques are well known. The delivery system typically includes a sheath and/or a catheter through which the implant is delivered to the target location. The implant is generally deployed from the sheath or catheter at the target location. Some implantable devices are completely self-expanding; they self-expand when released from the sheath or catheter and do not require any further expansion after the self-expanding step. The self-expansion can occur by proximally retracting the sheath or catheter, by pushing the implantable device from the sheath or catheter, or a combination thereof. Some implantable devices, however, are configured and adapted to be actuated during or after the self-expansion step. Exemplary replacement heart valves which can be actuated after a self-expansion step can be found described in co-pending application Ser. No. 10/982,388, filed Nov. 5, 2004, and application Ser. No. 10/746,120, filed Dec. 23, 2003, the disclosures of which are hereby incorporated by reference herein. It may be advantageous to lock an expandable medical device in a fully deployed and locked configuration to secure the device in the deployed.

During the delivery process the medical device can be actuated by the delivery system using one or more actuators. For example, an actuator (e.g., in the form of a knob on a handle of the delivery system) may be actuated (e.g., turned) to cause a component of the delivery system to move relative to another component in the delivery system or relative to the implantable device, or both. It is generally desirable to make the delivery process as easy as possible for the physician, reduce the time needed to complete the procedure, and reduce the mechanical complexity of the delivery system. In some delivery procedures, multiple components of the delivery system need to be actuated to deploy the implant. It may also be necessary to ensure that multiple steps are carried out in a certain order. What are needed are delivery systems which can simplify the deployment procedure of the medical device and/or ensure that multiple steps are performed in a certain order.

SUMMARY OF THE INVENTION

One aspect of the disclosure is a medical device system. The system includes a delivery system comprising a delivery sheath, a first actuation element, and a second actuation element, an expandable medical device adapted to be percutaneously delivered to a target location in a patient through the sheath in an unlocked delivery configuration, wherein the medical device comprises an expandable portion, a first locking member and a second locking member, and the first locking member and second locking member engage in a locked configuration to maintain the medical device in a locked deployed configuration, wherein the first actuation element is reversibly coupled to the first locking member and second actuation element is reversibly coupled to the second locking member when the medical device is in the collapsed delivery configuration.

In some embodiments the first locking member is disposed distal to the second locking member when the medical device is in the unlocked delivery configuration.

In some embodiments the first and second actuation elements are adapted to apply axially directed forces on the first and second locking elements to move the first locking element closer to the second locking element to lock the first and second locking elements together.

In some embodiments the system further comprises a delivery catheter adapted to be within the sheath and movable relative to the sheath, wherein the first actuation element is coupled to a distal portion of the catheter. The first actuation element can be adapted to radially expand when deployed from the delivery sheath.

In some embodiments there are a plurality of first actuation elements and a plurality of second actuation elements, and wherein there are a plurality of first locking members and a plurality of second locking members.

In some embodiments the method further comprises a first release actuation member which maintains the reversible coupling of the first actuation element and the first locking member. In some embodiments the system further comprises a second release actuation member which maintains the coupling between the second actuation element and the second locking member.

In some embodiments the first actuation element is reversibly coupled to the first locking member and second actuation element is reversibly coupled to the second locking member when the medical device is in an expanded and unlocked configuration.

One aspect of the disclosure is a medical device system. The system includes a delivery system comprising a housing disposed external to a subject, the housing comprising an actuator, wherein the delivery system is configured and arranged such that the actuator is adapted to move a first delivery system component independently of a second delivery system component, and wherein the delivery system is further configured and arranged such that actuator is adapted to move the first delivery system component and the second delivery system component at the same time.

In some embodiments the actuator is a single actuation element and wherein the delivery system and actuator are configured such that the actuator is adapted to be moved in a singular type of motion to move the first delivery system component independently of the second delivery system component and move the second delivery system component and the second delivery system component at the same time.

In some embodiments the actuator is configured to move the first delivery system component and the second delivery system component in a particular sequence.

In some embodiments the housing further comprises a second actuator which is configured to uncouple the second delivery system component from a medical device.

In some embodiments the housing further comprises an access door, the movement of which allows access to the second actuator.

One aspect of the disclosure is a method of deploying a medical device in a patient with a delivery system. The method includes providing a delivery system comprising a housing disposed external to the patient, wherein the housing comprises an actuator, actuating the actuator to move a first delivery system component independently of a second delivery system component, and actuating the actuator to move the first delivery system component and the second delivery system component at the same time.

In some embodiments actuating the first and second delivery system components comprises actuating the actuator with a singular type of motion.

In some embodiments the actuating steps actuate the first and second delivery system components in a particular sequence.

INCORPORATION BY REFERENCE

All publications and patent applications mentioned in this specification are hereby incorporated by reference herein to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1B shows an exemplary replacement heart valve in a collapsed and delivery.

FIG. 2B shows an exemplary medical device delivery system reversibly coupled to a medical device, wherein the medical device is in a deployed and locked configuration.

FIGS. 6A and 6B show an exemplary reversible coupling mechanism between a delivery system and a medical device.

FIGS. 7A-7D shows an exemplary lock and release mechanism of a medical device.

FIGS. 8A-8G shows an exemplary lock and release mechanism of a medical device.

FIG. 9 shows an exemplary reversible coupling mechanism between a delivery system and a medical device.

FIG. 10 shows an exemplary reversible coupling mechanism between a delivery system and a medical device.

FIGS. 11A-11D show an exemplary lock and release mechanism of a medical device.

FIGS. 12A-12C show an exemplary lock and release mechanism of a medical device.

FIGS. 13-14E show an exemplary lock and release mechanism of a medical device.

FIGS. 17A-17D illustrate a portion of an exemplary delivery system in which a single handle actuation element can move two different delivery system components independently of one another.

FIGS. 20A-20C illustrate a portion of an exemplary delivery system in which a single handle actuation element can move two different delivery system components independently of one another.

FIGS. 23A-23C illustrate actuating a second actuator to control movement of different portions of the medical device delivery process.

DESCRIPTION OF THE INVENTION

The present disclosure describes medical devices and delivery systems for delivering medical devices to a target location in a subject. The medical devices can be implantable or they can be adapted to be temporarily positioned within the subject. The delivery systems can be adapted to deliver a wide variety of suitable medical devices to a target location in a subject, but in some embodiments are configured for minimally invasive delivery procedures, such as endovascular procedures. In some embodiments the medical device is a replacement heart valve (e.g., a replacement aortic heart valve), and the delivery system is configured to deliver the replacement heart valve endovascularly to replace the functionality of the subject's native heart valve.

Figure 1A:
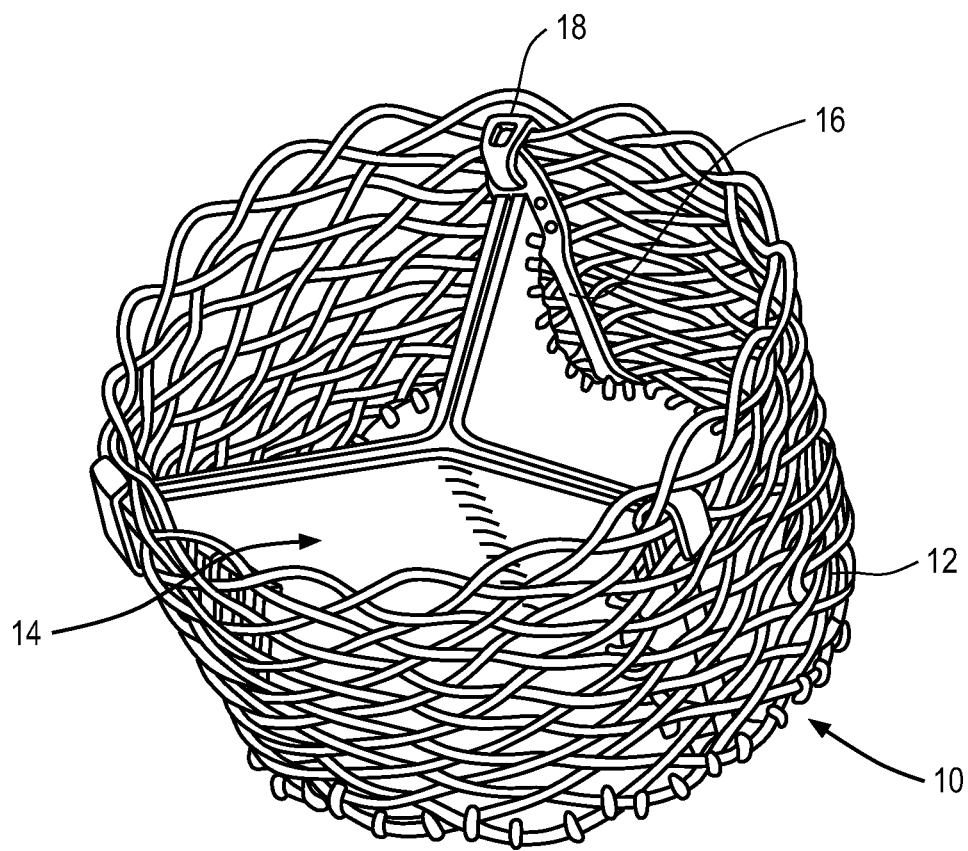
FIG. 1A shows an exemplary replacement heart valve in a deployed and locked configuration.

FIGS. 1A and 1B show replacement heart valve 10 including anchoring element 12, shown comprising a braided material, and replacement valve leaflets 14 (not shown in FIG. 1B for clarity). Replacement heart valve 10 also includes three first locking members 16, also referred to herein as posts, and three second locking members 18, also referred to herein as buckles. Three posts and three buckles are shown, each post being associated with one of the buckles. FIG. 1A shows anchoring element 12, also referred to herein as anchor, in a fully deployed configuration in which anchoring element 12 is locked and maintained in the deployed configuration by the locking interaction between first locking members 16 and second locking members 18. FIG. 1B shows replacement heart valve 10 in a collapsed delivery configuration in which the replacement heart valve is delivered within a delivery system to a target location within the subject (delivery system not shown).

In this embodiment valve leaflets 14 are attached to posts 16 at the valve's three commissures. Posts 16 therefore support the valve within the anchoring element. The posts and buckles (or other suitable first and second locking members) are both coupled to the anchor. When the anchoring element 12 is in the collapsed configuration as shown in FIG. 1B, each locking element of posts 16 which is configured to lock with a corresponding locking element of buckles 28 is located distally relative to the locking element of the buckle to which is it to adapted to be locked. Stated alternatively, the locking elements of the buckles which are configured to lock to the locking elements of the posts are located proximally to the locking elements of the posts in the delivery configuration.

Figure 2A:
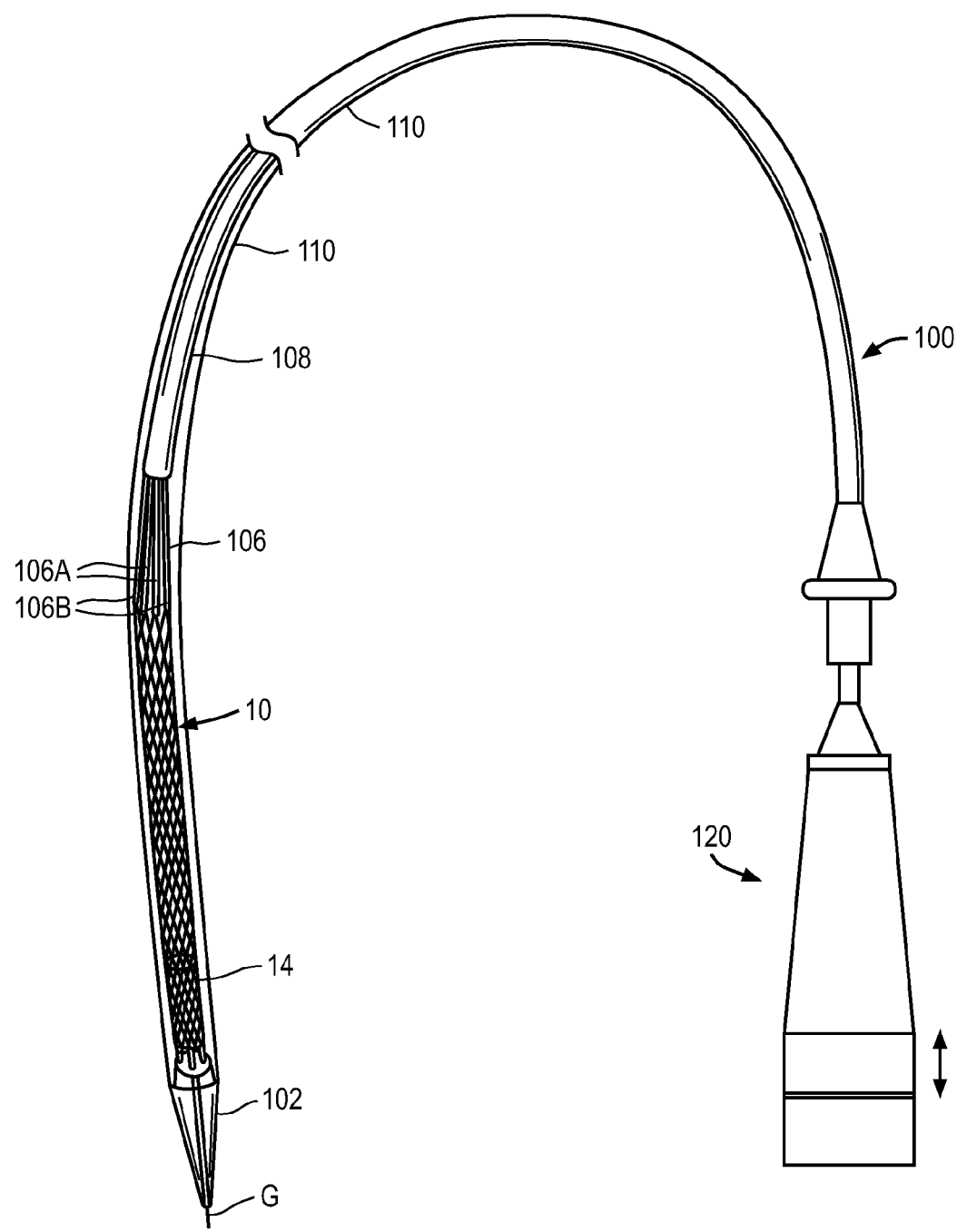
FIG. 2A illustrates an exemplary medical device delivery system reversibly coupled to a medical device, wherein the medical device is in a collapsed configuration.

FIGS. 2A and 2B illustrate an exemplary embodiment of a delivery system 100 and components thereof which can be used to deliver and deploy a medical device at a target location in a subject. Delivery system 100 includes handle 120, sheath 110, catheter 108 disposed with sheath 110, and actuation elements 106A and 106B which are reversibly coupled to replacement heart valve 10. In FIG. 2A, heart valve 10 is in a collapsed delivery configuration (also shown in FIG. 1B) within sheath 110. Delivery system 100 also includes guidewire G and nosecone 102. In some embodiments catheter 108 has central lumen 109 and a plurality of circumferentially disposed lumens Lu.

In FIGS. 2A and 2B, the plurality of actuation elements 106A are shown reversibly coupled to a proximal region of anchoring element 12. Specifically, actuation elements 106A are reversibly coupled to the proximal end of the anchoring element 12 via a reversible coupling mechanism. Actuation elements 106B are reversibly coupled to a region of the replacement heart valve distal to the proximal end of the anchoring element. Specifically, actuation elements 106B are shown reversibly coupled to posts 16 via a reversible coupling mechanism. Details of this and similar embodiments can be found in U.S. Patent Publication Nos. 2005/0137686 and 2005/0143809, the disclosures of which are incorporated by reference herein.

In the embodiments shown in FIG. 1A-2B, the anchoring element comprises a braided material, such as nitinol, and is formed of one or more strands of material. In one embodiment the anchoring element 12 is formed of a shape memory material and is heat set in a self-expanded configuration, such that when the anchoring element is deployed from the sheath of the delivery system, the braid will begin to naturally begin to shorten and expand from the collapsed delivery configuration to the memory self-expanded configuration. The self-expanded configuration can be thought of as an at-rest or partially deployed configuration, and is described in more detail in U.S. Patent Publication Nos. 2005/0137686 and 2005/0143809. Once the anchoring element has expanded to the partially deployed configuration, at least one of the actuators 106A and 106B is actuated via an actuator on a handle disposed external to the patient. As is described in more detail in U.S. Patent Publication Nos. 2005/0137686 and 2005/0143809, actuators 106B can be actuated in the proximal direction relative to the actuation elements 106A, which applies a proximally directed force to the posts, which applies a proximally directed force to a distal region of the anchoring element. Actuators 106A can, alternatively or in addition to the proximally directed force, be actuated in a distal direction to apply a distally directed force on a proximal region of the anchoring element. The axially directed forces actively foreshorten the anchoring element, moving the posts closer to the buckles until the posts and buckles lock together to lock the anchoring element in a fully deployed and locked configuration. The locked configuration is therefore shorter than the partially-deployed configuration.

Figure 3A:
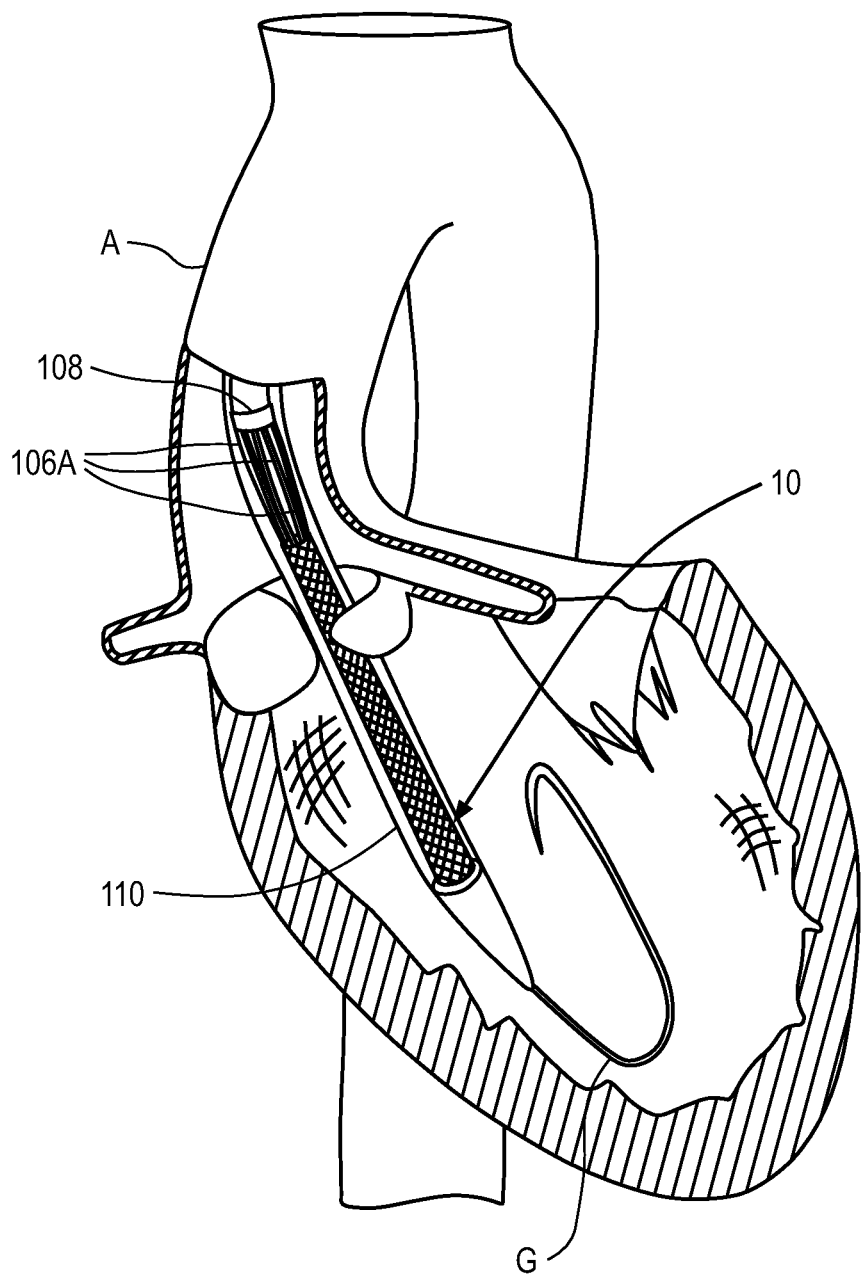
FIGS. 3A-3G illustrate an exemplary medical device deployment and locking procedure.

FIGS. 3A-3G illustrate an exemplary method of delivering a replacement aortic heart valve in a delivery configuration and deploying it from a delivery sheath to a fully deployed and locked configuration. In this embodiment actuation elements 106B are reversibly coupled to the posts of the replacement valve, but actuation elements 106A, which may also be referred to herein as "fingers," are reversibly coupled to the buckles. There are three actuation elements 106A reversibly coupled to the three buckles, and there are three actuation elements 106B reversibly coupled to the three posts. As seen in FIG. 3A, replacement valve 10 is delivered in a collapsed delivery configuration within sheath 110 in a retrograde fashion through aorta A over guidewire G and placed across a patient's aortic valve using known percutaneous techniques.

Figure 3B:
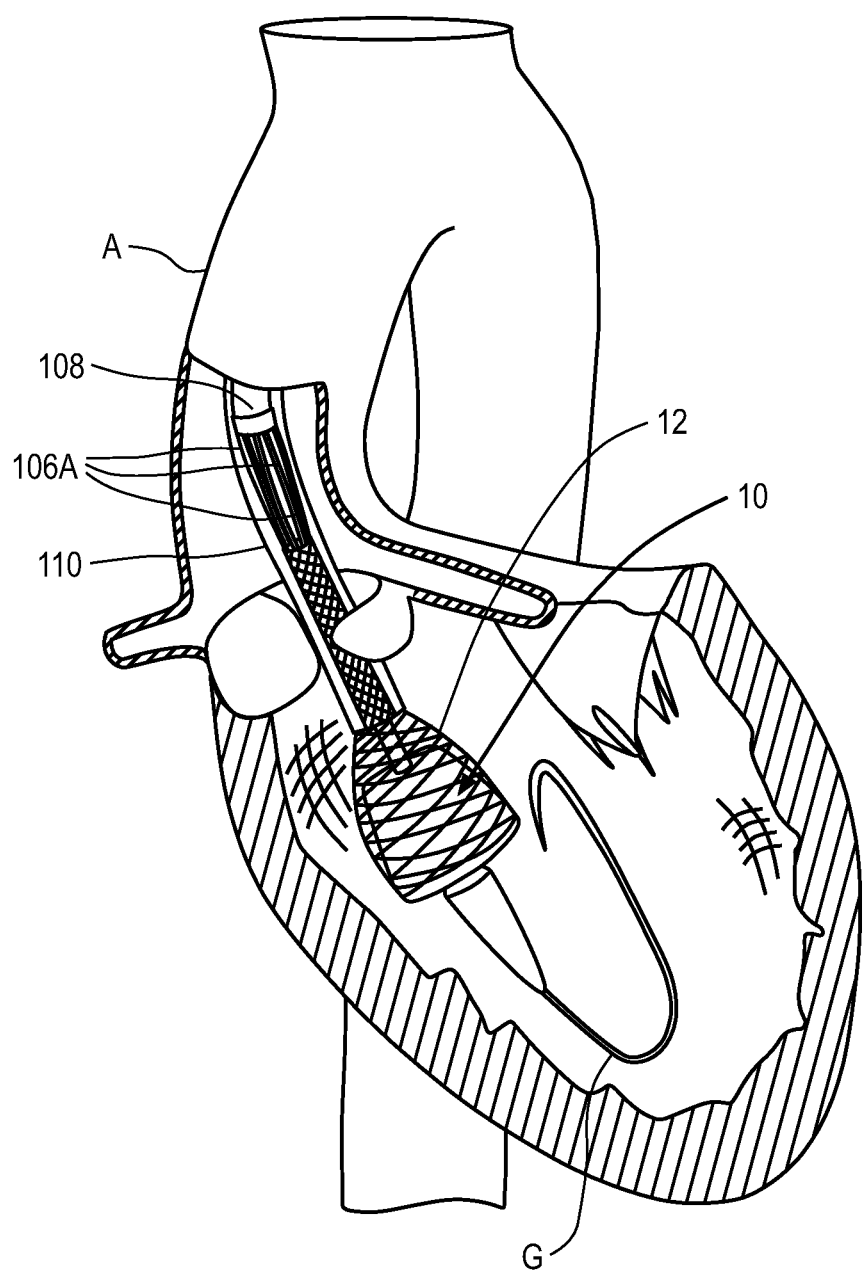
Figure 3C:
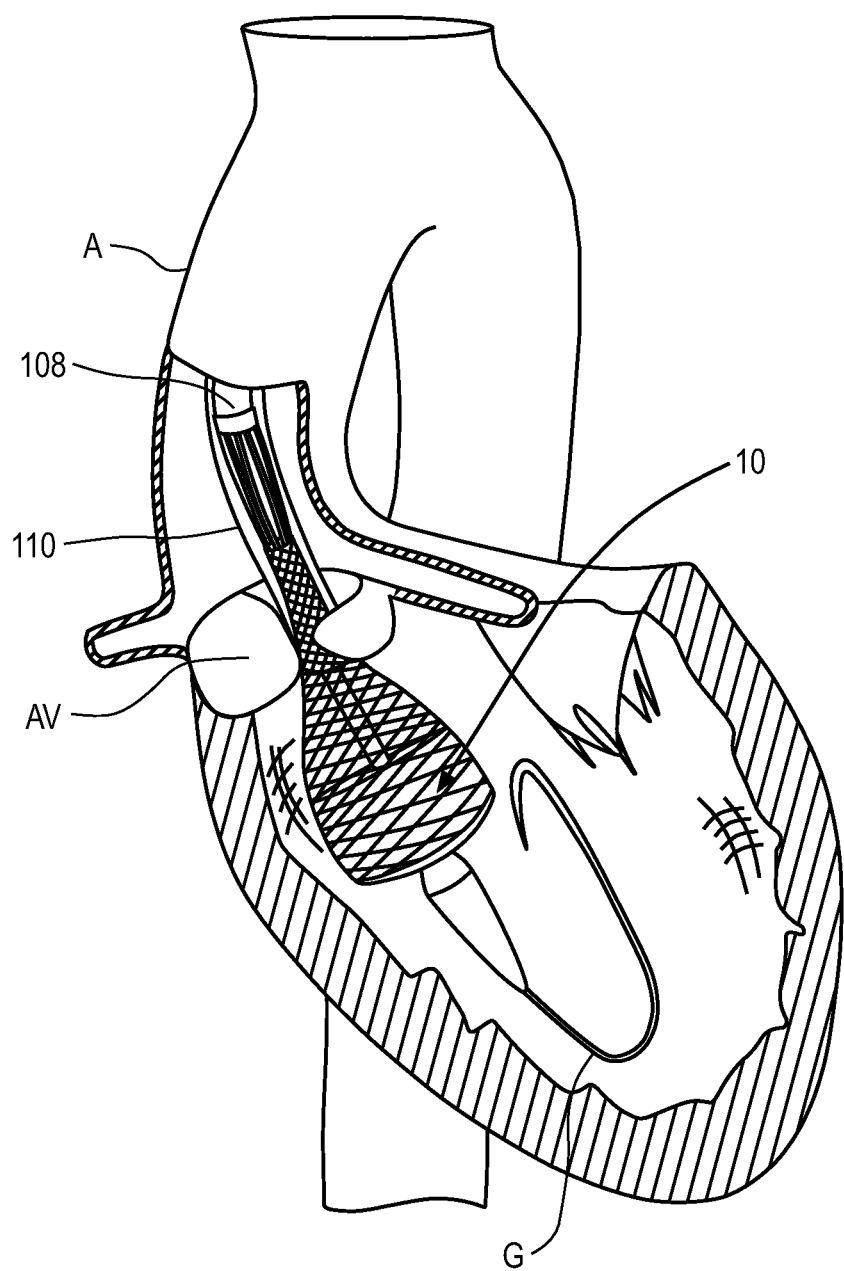
Figure 3D:
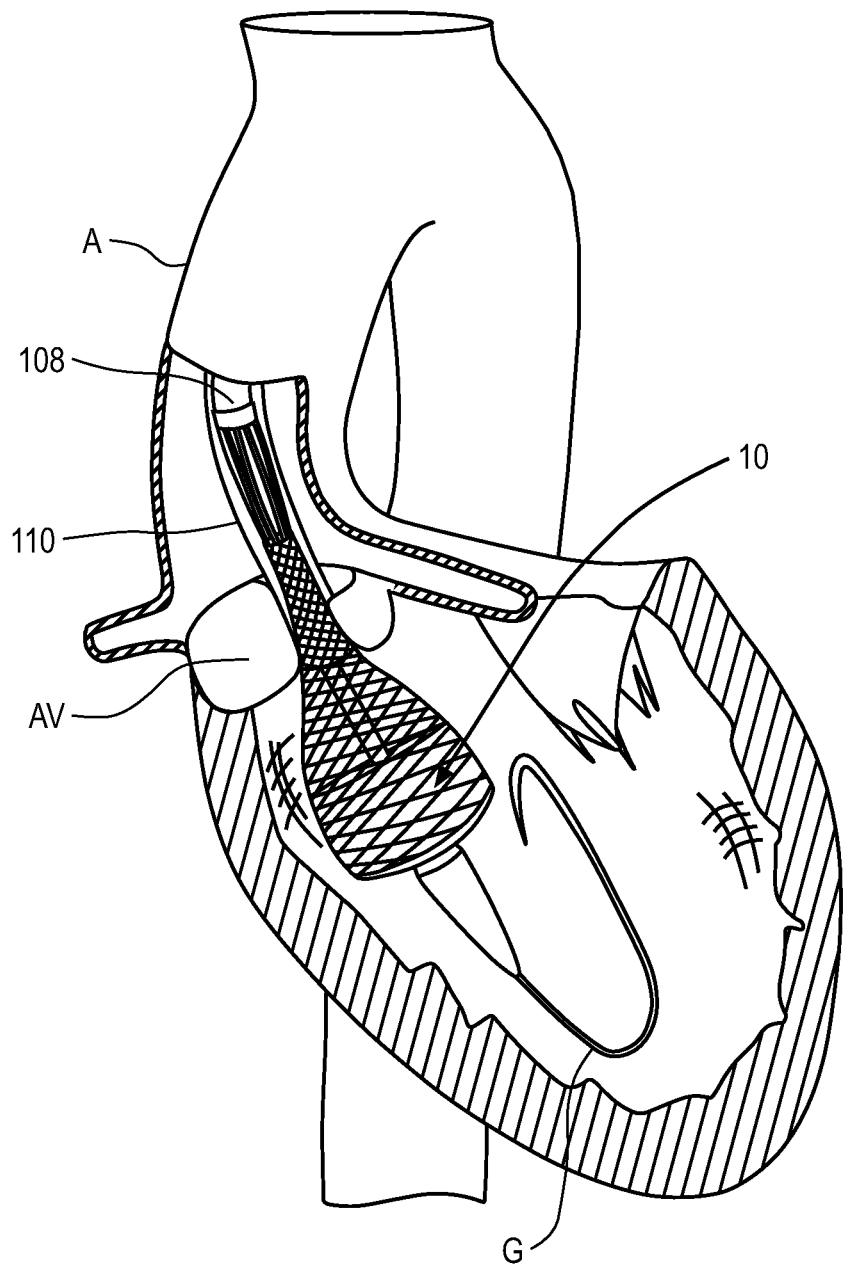
Figure 3E:
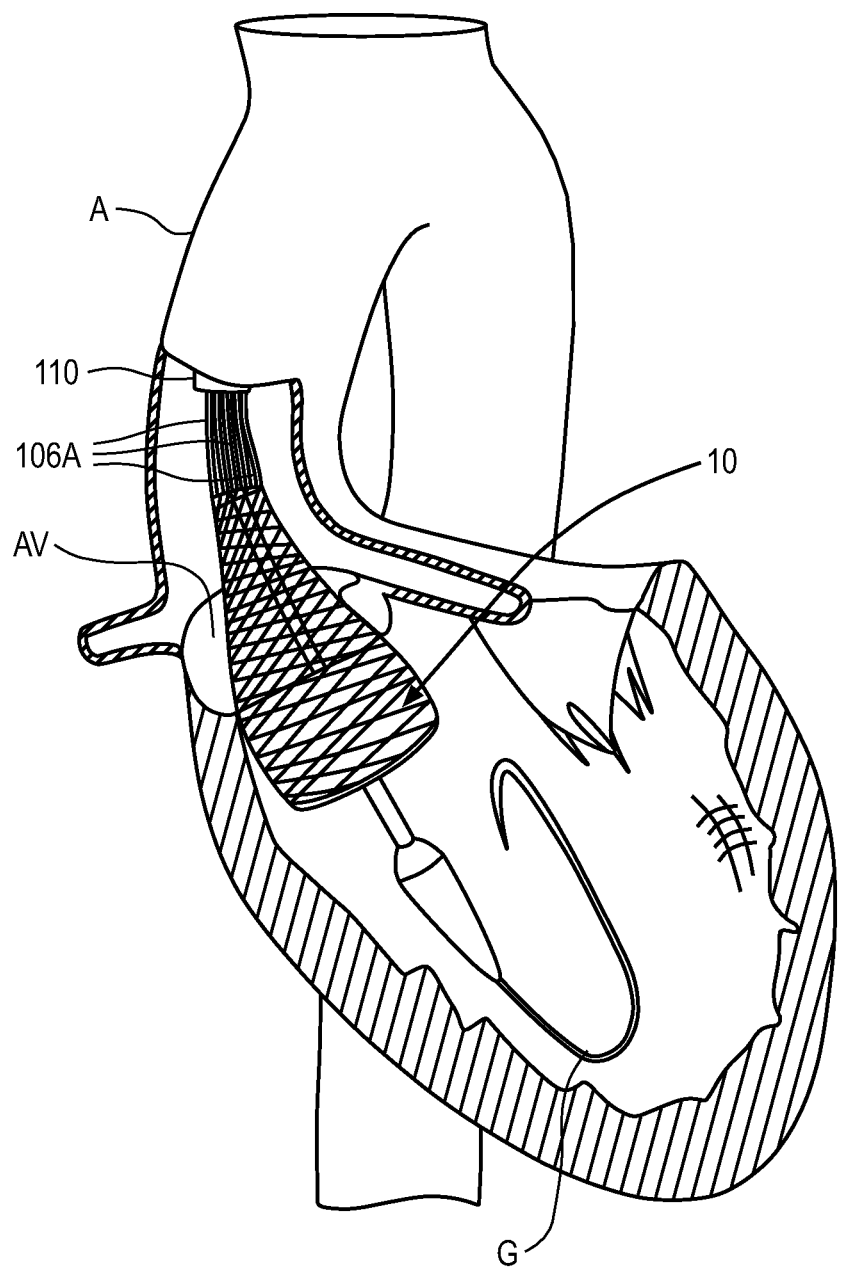
Figure 3F:
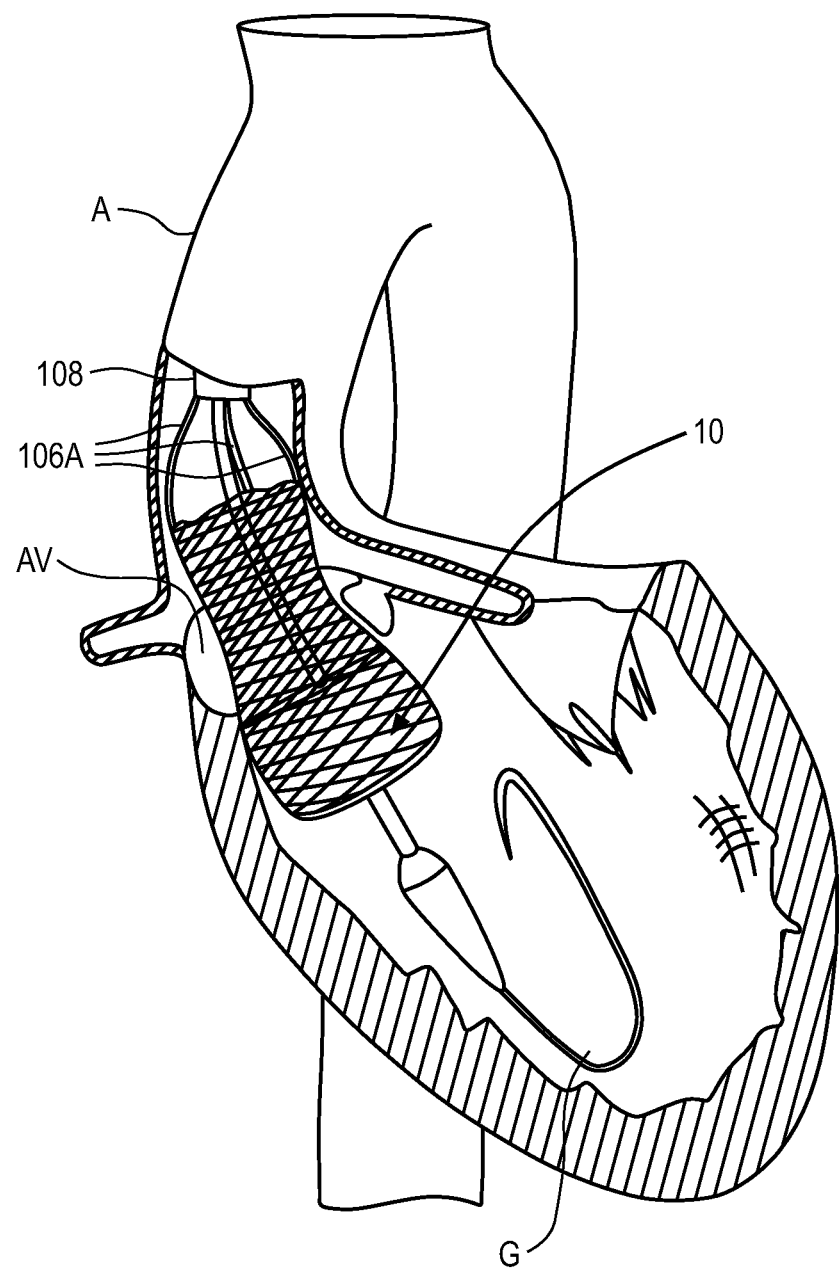

Once sheath 110 is positioned across the native valve as shown in FIG. 3A, sheath 110 is retracted proximally relative to the replacement valve using an actuator on the delivery system handle which is disposed external to the patient (examples of which are described in detail below). As the sheath is withdrawn, as seen in FIG. 3B, the distal portion of anchoring element 12 begins to self-expand due to the material properties of the anchoring element. The anchoring element can have a memory self-expanded configuration such that as the sheath is withdrawn the anchor begins to self-expand, or return to its memory configuration. As the sheath continues to be retracted proximally, the anchoring element continues to self-expand, as shown in FIGS. 3C and 3D. In FIG. 3E the sheath has been retracted proximally such that the distal end of the sheath is disposed proximal to the distal end of fingers 106A. In FIG. 3E the sheath is not retracted far enough proximally to allow the fingers to self-expand. As such, although the anchoring element is completely out of the sheath, the proximal end of the anchor does not expand towards its memory configuration. Only after the sheath has been retracted past the distal end of catheter 108 can the fingers fully self-expand, as is shown in FIG. 3F. This allows the proximal end of the anchoring element to expand.

Figure 3G:
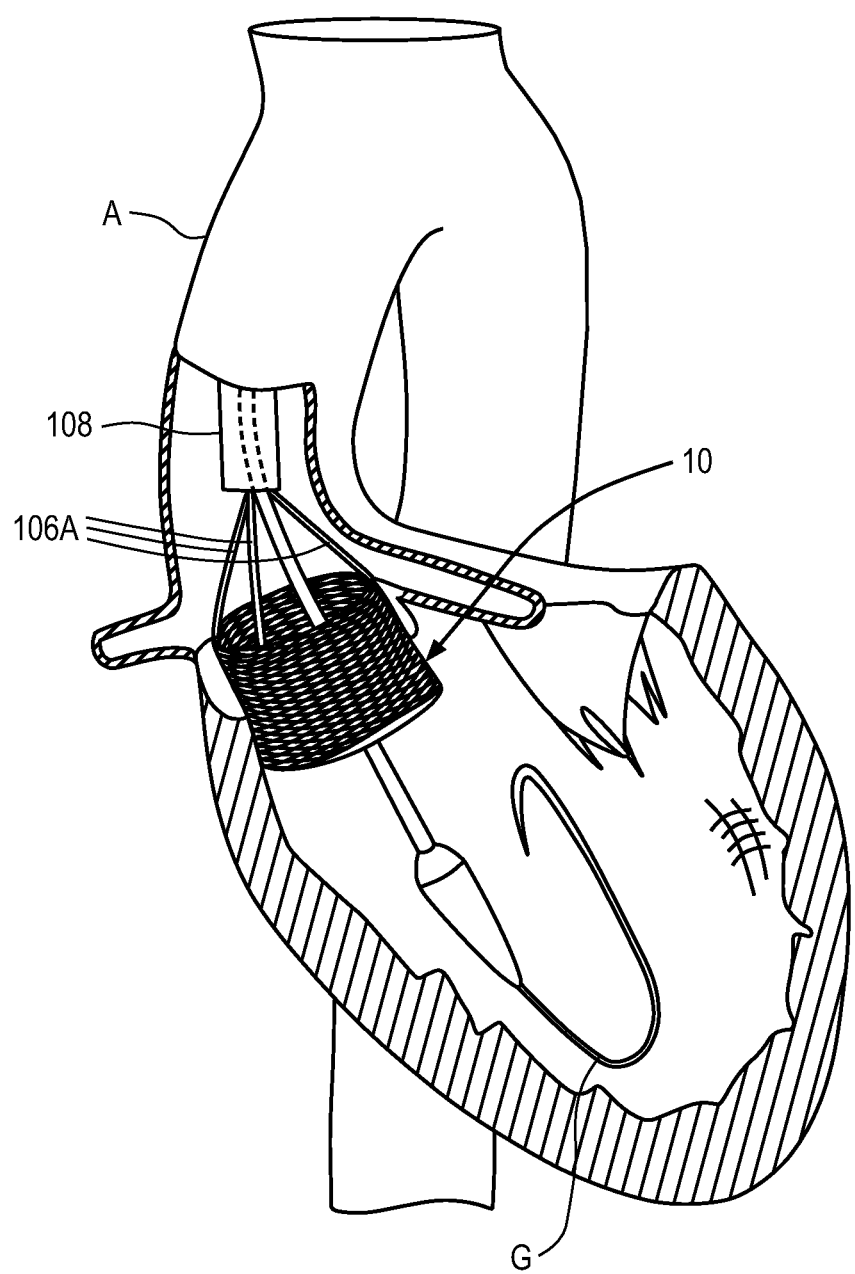

The anchoring element is then actively foreshortened (and potentially further expanded) to the fully deployed and locked configuration shown in FIG. 3G by the application of axially directed forces (proximally and distally directed). To actively foreshorten the anchoring element, a proximally directed force is applied to posts via actuation elements 106B (not shown in FIGS. 3A-3G but which are coupled to the posts), and/or a distally directed force is applied to buckles via actuation elements 106A. In one embodiment a proximally directed force is applied to posts through actuation elements 106B, and fingers 106A are held in position to apply a distally directed force to the buckles. This active foreshortening causes the posts and buckles to move axially closer to one another until they lock together, which maintains the anchoring element in a fully deployed and locked configuration in FIG. 3G. The actuation elements 106A and 106B are then uncoupled released from the buckles and posts, respectively, and the delivery system is then removed from the subject. The details of exemplary locking processes and release processes are described in detail below. Additional details of delivery, deployment, locking, and release processes that may be incorporated into this and other embodiments can be found in U.S. Patent Publication No. 2005/0137699, filed Nov. 5, 2004, U.S. Patent Publication No. 2007/0203503, filed Feb. 14, 2007, and U.S. Patent Publication No. 2005/0137697, filed Oct. 21, 2004, each of which is incorporated by reference herein.

Figure 4:
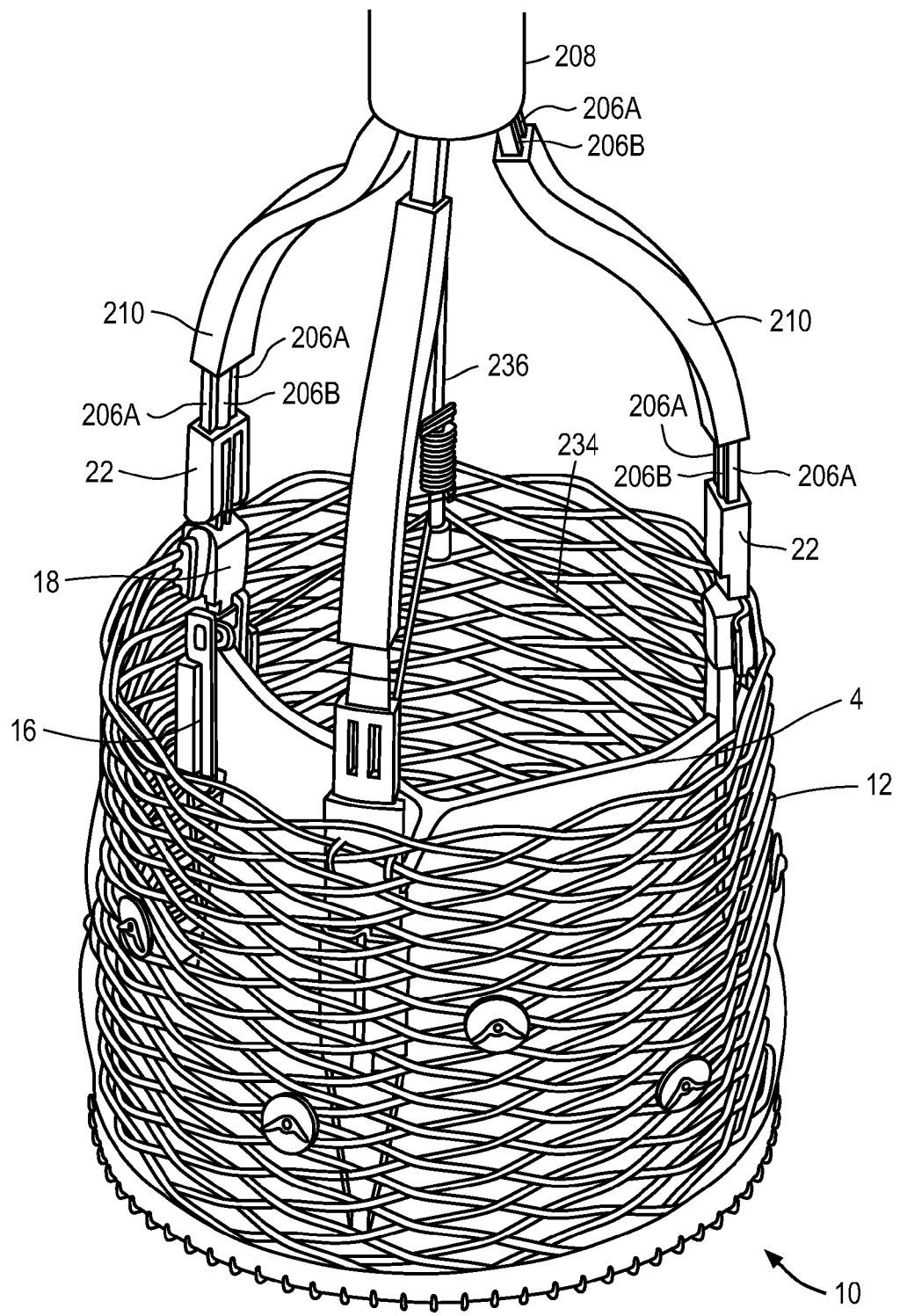
FIG. 4 shows an exemplary replacement heart valve reversibly coupled to a portion of a delivery system.

FIG. 4 shows replacement heart valve 10 and a distal portion of the delivery system, including catheter 208, which were described in reference to FIGS. 3A-3G. Heart valve 10 is in a fully deployed and locked configuration, with actuation elements 206A ("fingers") and 206B still reversibly coupled to buckles 18 and posts 16, respectively. The configuration and arrangement in FIG. 4 is therefore similar to that shown in FIG. 3G. The commissure portions of leaflets 14 are affixed to the three posts 16, while posts 16 are moveably coupled to anchoring element 12 (e.g., via sutures or wires) at a location distal to the proximal end of anchoring element 12. Replacement heart valve 10 also includes buckles 18 (three are shown) which are affixed (but may be moveably coupled to the anchor similar to the posts) to anchor 12 (e.g., via wires or sutures) at a proximal region of anchor 12. In FIG. 4, the actuation elements 206B are reversibly coupled to posts 16, while actuation elements 206A are reversibly coupled to buckles 18. The delivery system also includes three actuator retaining elements 210, each of which are adapted to receive therein an actuation element 206B and an actuation element 206A. Actuation elements 206A are shown attached at their proximal end to the distal end of catheter 208, while actuation elements 206B are configured and arranged to move axially within catheter 208. Actuation elements 206B therefore are configured and arranged to move axially with respect to actuation elements 206A as well. Fingers 206A and actuation elements 206B are maintained closely spaced to one another (at least while the delivery system is coupled to the replacement valve) with actuator retaining elements 210. Retaining elements 210 have a lumen therein in which fingers 206A are disposed and through which the actuation elements 206B can be actuated axially. Fingers 206A are shown disposed radially outward relative to the actuation elements 206B, which are shown as generally cylindrical rods. The replacement heart valve in FIG. 4 has not been released from the delivery system.

Figure 5A:
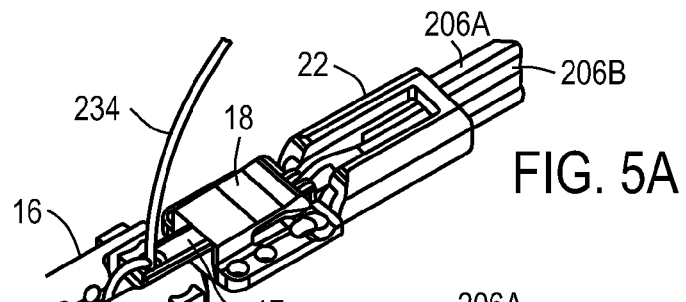
FIGS. 5A-5E show an exemplary lock and release mechanism for a medical device.

FIGS. 5A-5E illustrate the process of uncoupling the delivery system from the heart valve shown in FIG. 4 (anchoring element is not shown). In FIG. 5A post 16 has an elongated locking portion 17 which is adapted to be pulled into an internal channel within buckle 18. Locking portion 17 of post 16 has a locking element in the shape of a groove which is adapted to receive a tooth on the buckle 18. As the post is pulled into the buckle, the tooth on the buckle will engage the groove on the post and lock the post and buckle together, maintaining the anchoring element in a locked configuration. This configuration is shown in FIG. 5A. In this configuration, actuation element 206B (or "rod") is reversibly coupled to post 16. Rod 206B includes a portion that is disposed within a channel in post 16 such that bore 230 (see FIG. 5E) in the distal portion of rod 206B is aligned with bore 232 in post 16. Pin 234, which is part of pin assembly 236 as can be seen in FIG. 4, extends through both rod bore 230 and post bore 232 to couple the rod to the post. The distal portion of pin assumes a curled or looped configuration, which prevents rod 206B from disengaging from post 16. In FIG. 5A finger 206A is reversibly coupled to buckle 18 via the interaction between tooth 239 on buckle 18 and groove 238 on finger 206A (see FIG. 5E). In FIG. 5A, collar 22 is positioned over the engagement between tooth 239 and groove 238 to retain the 206A and buckle 18 in a reversibly coupled configuration.

Figure 5B:
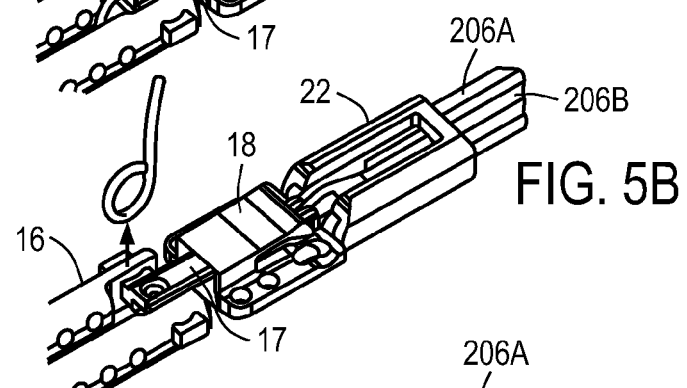
Figure 5C:
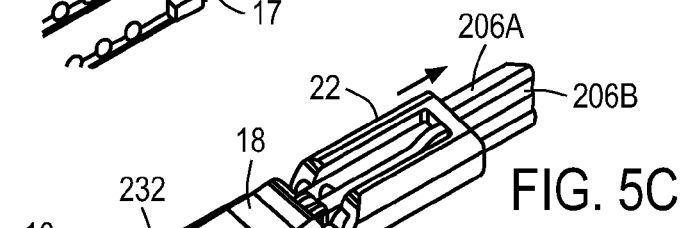
Figure 5D:
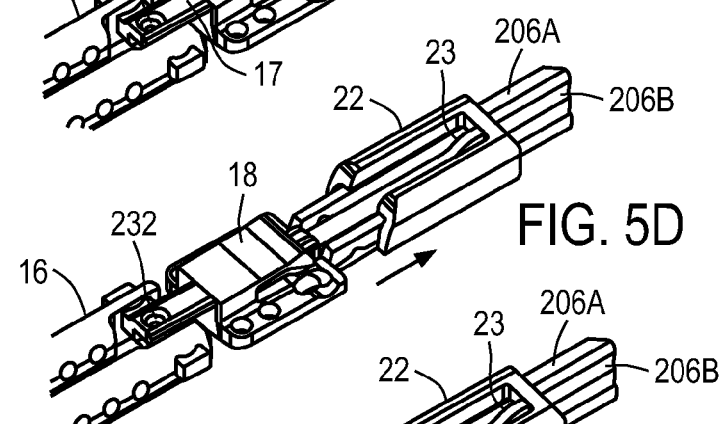
Figure 5E:
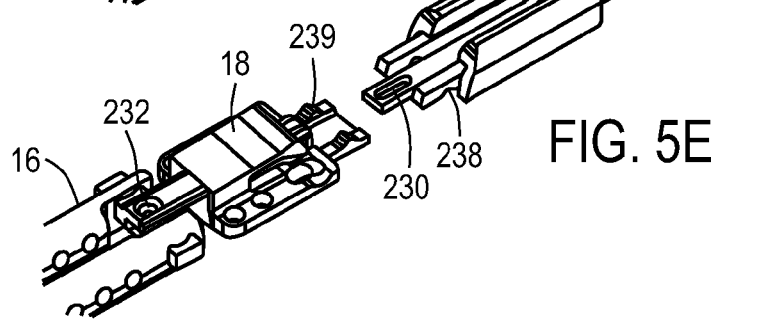

Once it has been determined to release the heart valve in place within the subject, pin 234 is first removed by retraction of pin assembly 236 (see FIG. 4) in the proximal direction, which pulls the pin through bores 230 and 232 and uncouples rod 206B from post 16, which is shown in FIG. 5B. Next, rod 206B is pulled back in the proximal direction via actuation of an actuator on the delivery system handle. Once rod 206B has been pulled to the position in FIG. 5C, collar engagement 23 engages collar 22 and pulls it in the proximal direction along with rod 206B. This causes the collar to be pulled proximally from the position in FIG. 5C to the position in FIG. 5D. Retracting the collar to the position in FIG. 5D allows tooth 239 of the buckle to disengage groove 238 with continued retraction of rod 206B, which is shown in FIG. 5E. Both rod 206B and finger 206A are uncoupled from the heart valve, and the delivery system is now retracted from the patient with the medical device implanted in place.

In some embodiments the axially directed force vectors applied by the fingers 206A to the buckles and the rods 206B to the posts can be in substantially opposite directions to enhance the efficiency of the foreshortening and locking process. An advantage of coupling the fingers directly to the buckles is that the buckles are better aligned with the posts during the foreshortening and locking process. This can help ensure that the post, when pulled proximally, will better align with the buckle such that the post can be efficiently locked with the buckle. When using an anchor that may become twisted or distorted under high foreshortening and locking forces (such as an anchor comprising a braided material), it can be beneficial to ensure that a buckle which is coupled to the anchor (and thus may fall out of alignment with the post) remains properly aligned with the post. Directly coupling the fingers to the buckle can provide these benefits. This can also increase the general efficiency of proximally directed pulling forces because less force may be required to pull and lock the posts with the buckles. When incorporating actuators on a handle to control delivery and deployment of a medical device, reducing the amount of force that is needed to be applied to the handle actuator can simplify the delivery system design.

FIGS. 6A and 6B illustrate an alternative embodiment of post 250 which is reversible coupled to actuation element 252. FIG. 6B is a partially exploded view identifying the components shown in FIG. 6A. Actuation element 252 includes rod 254, tab deflector 256, and retaining clip 258. Rod 254 can be actuated in a proximal direction P by actuating an actuator on a handle disposed external to the patient as described herein.

Rod 254 is attached to tab deflector 256 and to retaining clip 258. Rod 254 includes, at its distal end, catch 260, which engages with clip element 262 of retaining clip 258. Post 250 has an internal channel therein adapted to slidingly receive retaining clip 258 and tab deflector 256, each of which are adapted to receive rod 254 therein. Tab deflector 256 includes rib element 264. Retaining clip 258 includes clip feet 266. To lock the anchoring element (not shown), rod 254 is pulled in the proximal direction and clip feet 266 engage the distal end of post 250 and pull it in the proximal direction towards the buckle (not shown).

FIGS. 7A-7D show side-views of an exemplary locking sequence of post 250 shown in FIGS. 6A and 6B to buckle 268 (anchor not shown). FIG. 7A shows rod 254 being actuated in the proximal directed by an actuation force generated from an actuator on the handle of the delivery system external to the patient. In FIG. 7A, post 250 is still distal to buckle 268. As rod 254 continues to be pulled in the proximal direction, catch 260 (shown in FIG. 6B) applies a proximally directed force to clip element 262 (shown in FIG. 6B). This causes clip feet 266 to apply a proximally directed force to the distal end of post 250. This causes the post to move in the proximal direction.

Post 250, tab deflector 256, and retaining clip 258 thus move towards buckle 268, as is shown in FIG. 7A.

Continued actuation of the actuator external to the patient causes the post, the deflector, and the clip to be pulled further in the proximal direction into a position within a channel within buckle 268, as is shown in FIG. 7B. Because rib element 264 of tab deflector 256 is disposed adjacent groove 272 of post 250, rib element 264 prevents buckle tooth 270 from engaging groove 272 of post 250 (shown in FIG. 7B). This prevents the post from locking with the buckle until the physician determines that it is appropriate to do so. Rib element 264 thereby acts as a lock prevention mechanism. The post (and thus the anchor) can be moved distally to lengthen the anchoring element at this point by applying a distally directed force on post 250 using the actuator on the handle.

Once the desired position of the anchor has been obtained, rod 254 continues to be actuated in the proximal direction. This can be done using the same actuator on the handle or a different actuator as described in more detail below. The continued proximal force to rod 254 causes feet 266 to be pinched inwards towards one another to thereby disengage and uncoupled them from the distal end of post 250. This pulls feet 266 within the distal opening of post 250. This releases clip 258 from post 250 and uncouples the rod, deflector, and clip from the post. Continued actuation of the actuator will move the cable, deflector and clip in the proximal direction to the position shown in FIG. 7C. Rib element 264 is disposed proximal to tooth 270 and groove 272 and thus no longer prevents them from locking together. The tooth therefore engages the groove, locking the post to the buckle (shown in FIG. 7C). The anchor (not shown) is now locked in the fully deployed and locked configuration. Continued actuation of rod 254 pulls the rod, clip, and deflector from the patient, as is shown in FIG. 7D.

FIGS. 8A-8G illustrate a side view of a locking and release sequence of an alternative embodiment of a post, buckle, and actuation elements. The system includes actuation element 280 in the form of a rod, buckle 282, post 286, and clip 290. The clip 290 includes feet 294 and rib element 292. Actuation of an actuator on the handle causes rod 280 to be pulled in the proximal "P" direction, as shown in FIG. 8A. Continued actuation pulls rod 280, post 286, and clip 290 through a channel within buckle 282, as shown in FIG. 8B. As rod 280 continues to be pulled, a surface of buckle tooth 284 slides over surface 295 of clip 290, as shown in FIG. 8B. Feet 294 engage the distal end of buckle 282, as shown in FIG. 8C. The top view of this position is shown in FIG. 8G. Between the positions shown in FIGS. 8B and 8C, rib element 292 has prevented the post from locking with the buckle. In the position shown in FIG. 8C, tooth 284 is engaging surface 287 of post 286. The location of feet 294 ensures post groove 288 has been pulled far enough proximally before the clip 290 is removed from the post. From the position shown in FIG. 8C, continued proximal movement of rod 280 will cause feet 294 to pinch together and retract into the channel in buckle 282. This releases clip 290 from post 286 and pulls the rod and clip in the proximal direction. Once the clip is released from the post, the post will begin to naturally move in the distal direction because the anchoring element (not shown, but in this embodiment comprises a braided material) begins to revert naturally to a self-expanded, partially deployed memory configuration (which is more fully described in the applications incorporated by reference herein). As the post begins to move distally, tooth 284 engages post groove 288 as is shown in FIG. 8E. This locks the post and buckle and locks the anchoring element in a fully deployed and locked configuration. The rod and clip can now be removed from the patient, as is shown in FIG. 6F.

FIGS. 9 and 10 show two alternative embodiments incorporating features of the lock and release embodiments above. The embodiment in FIG. 9 is similar to that shown in FIGS. 5A-5E, although rod 304 includes feet 306 which are similar to the feet shown in the embodiments in FIGS. 6A-8G. In this embodiment pin 234 from FIGS. 5A-5E is not needed, as the release of rod 304 from post 300 occurs when rod 304 is pulled proximally, causing feet 306 to pinch inwards and disengage from the post.

FIG. 10 shows an alternative embodiment which incorporates compressible feet 316 at the distal end of rod 314 and release pin 318 (actuated in the same way as shown in the embodiment in FIGS. 5A-5E). The embodiment in FIG. 10 can be thought of as a hybrid design between that shown in FIGS. 5A-5E and 9. One difference between the embodiment in FIGS. 5A-5E and 10 is that in FIGS. 5A-5E there is a slot 230 in the rod that pins the rod to the post. When pin 234 is under tension in FIGS. 5A-5E, the pin is in shear, which increases the likelihood of damaging the pin. In the design in FIG. 10, the slot 230 is not present, but rather the two feet 306 simply extend distally from a distal portion of the rod. Pin 318 maintains feet 316 in the spread-apart position shown in FIG. 10, essentially holding them open and maintaining the coupling between the feet and the post. In this design, the pin is in compression between the feet, rather than being in shear. Once the pin removed, a lower release force can then be applied to the rod to cause the feet to uncouple from the post. Having the pin in compression rather than shear is less likely to cause damage to the pin.

Each of FIGS. 11A-11D shows a side view and perspective view, respectively, of an alternative embodiment including post 320 and actuation element 322 in a sequence wherein post 320 changes configuration from a position in which it is not locked to a corresponding buckle 321 to a locked position, and in which the actuation element 322 is released from the post. Buckle 321 is not shown in the sequence for clarity, although buckle 321 is shown in FIG. 11A to display the relative positions of the post, actuation element, and buckle. FIGS. 12A-12C show the locking and release sequence including buckle 321.

In FIG. 11A actuation element 322 is reversibly coupled to post 320. Actuation element 322 includes rod 324, post lock prevention element 326, and post lock actuator 328. Post 320 includes post lock element 330. FIG. 11A illustrates an initial configuration of the respective components before the post is pulled towards the buckle. To actively foreshorten the anchoring element (not shown), the rod 324 is retracted in the proximal direction. Post lock prevention element 326 is initially engaged with post lock element 330, and thus proximal retraction of rod 324 causes proximal movement of post 320. Rod 324 continues to be pulled proximally until post 320 is pulled within buckle, as can be seen in FIG. 12A. In FIG. 12A the post is not yet locked to the buckle, and post lock element 330 is proximal to buckle lock element 332. To lock post 320 to buckle 321, a separate actuator (not shown) is actuated to retract the post lock prevention element 326 in the proximal direction to disengage post-lock prevention element 326 from post lock element 330, as shown in FIGS. 11B and 12B. Alternatively, rod 324 and post lock prevention element 326 may be engaged in a manner such that a continued proximal force applied to rod 324 will disengage post lock prevention element 326 from post lock element 330. Because the anchoring element has a memory configuration that is longer than the fully expanded and deployed configuration, once post-lock prevention element 326 is disengaged from post lock element 330, the anchor will attempt to return to its elongated memory configuration. Thus, post 320 begins to move in the distal direction. Distal movement of post 320 causes post-lock actuator 328 to apply a radially outward force to post lock element 330, moving it to a locked configuration shown in FIGS. 11C and 12C. Alternatively, or in addition to, once lock prevention element 326 is disengaged from post lock element 330, continued proximal retraction of rod 324 causes post-lock actuator 328 to apply a radially outward force on post lock element 330. Continued distal movement of post 320 causes post lock element 330 to engage with buckle lock element 332, locking post 320 to buckle 321. The lock prevents further distal movement of the post relative to the buckle, locking the anchor in an axially compressed and fully deployed configuration. Actuation element 322 can now be withdrawn proximally and removed from the patient.

Figure 13:
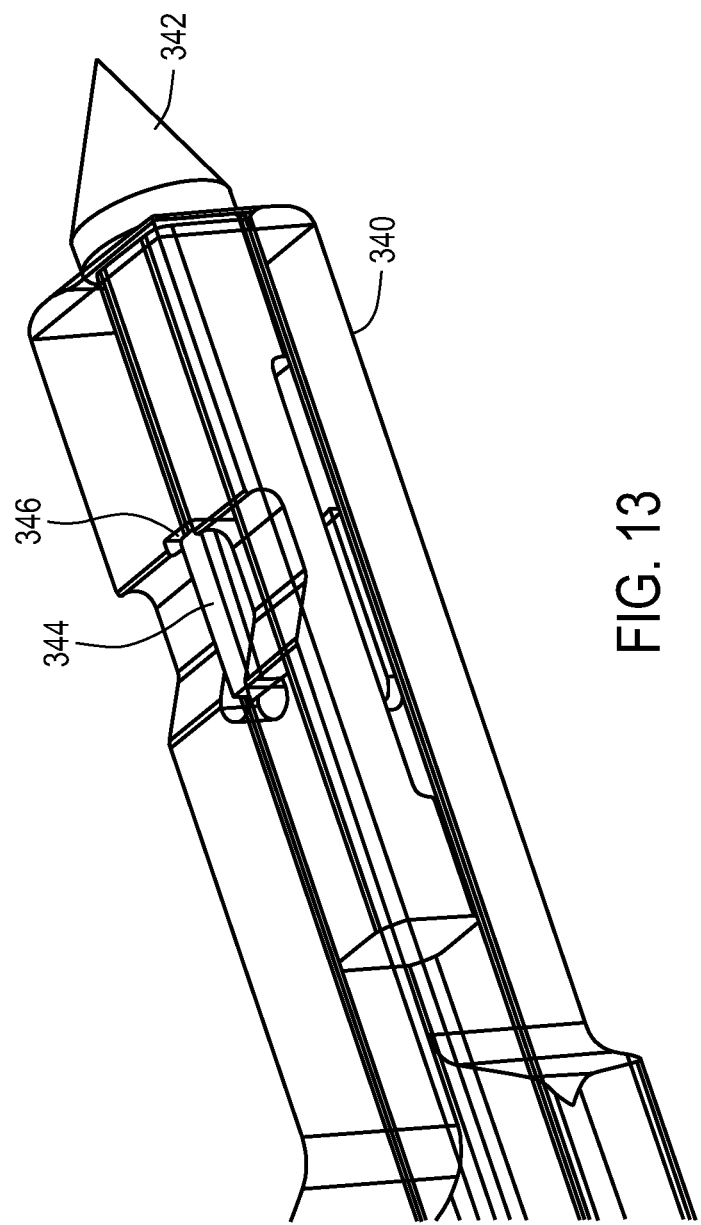

FIG. 13 shows an alternative embodiment of post 340 and clip 342, which includes deformable element 344. FIGS. 14A-14E show a sequence of locking post 340 to buckle 348 and releasing clip 342 from post 340. A rod (not shown) is attached to clip 342, similar to the embodiments described above. In the position shown in FIG. 14A, the proximal end of deformable element 344 engages surface element 346 of post 340. This engagement maintains the clip within the post as the clip is pulled proximally. This engagement also pulls the post proximally as the clip is pulled proximally. As the actuator is actuated the cable pulls the post and clip within the buckle 348 as shown in FIG. 14B. Continued actuation from the position shown in FIG. 14C causes tooth 350 of buckle 348 to engage and deform deformable element 344. Deforming element 344 allows tooth 350 to engage groove 352 to lock the buckle and post. This step also releases deformable element 344 from engagement with surface 346, thus releasing the clip from the post, as is shown in FIG. 14D. This step therefore also releases the rod and clip from the post. FIG. 14E shows the clip completely withdrawn proximally from the post.

Figure 15A:
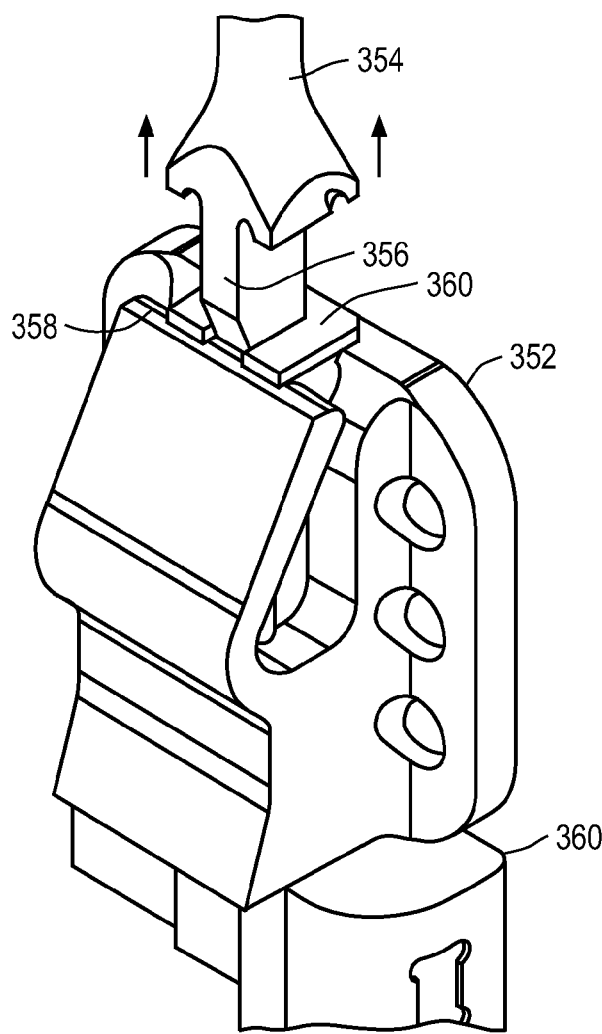
FIGS. 15A-16B show an exemplary lock and release mechanism of a medical device.
Figure 15B:
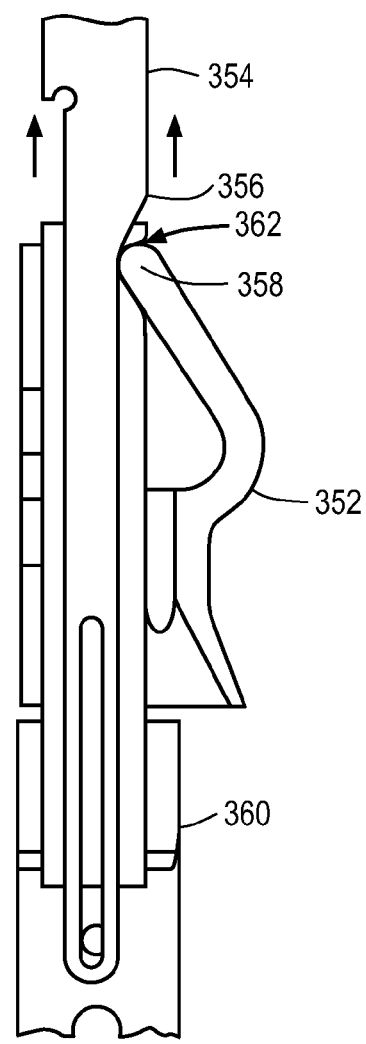

FIGS. 15A, 15B, 16A, and 16B illustrate an alternative embodiment of the post lock and release mechanism. The embodiment in FIGS. 15A-16B works similarly to those described above in that an actuator is actuated to pull the actuation element, or rod, which pulls the post towards the buckle to lock the anchoring elements. Rod 354 includes a clip similar to the clip in the embodiment in FIGS. 6A and 6B. FIG. 15A is a perspective view and FIG. 15B is a side view after rod 354 has been actuated and pulled proximally such that tooth 358 of buckle 352 is locked with groove 362 of post 360. Prior to the position shown in FIGS. 15A and 15B, surface 356 of rod 354 prevented tooth 358 from locking with the groove in the post. The clip at the distal end of the rod is engaged with a deformable element of the post such that continued actuation of the rod causes the deformable element to deform and release the post from the rod. This rod can then be removed from the patient by continued actuation of the actuator. Alternatively, a pin similar to pin 234 in FIGS. 5A-5E can be incorporated into the embodiment, such that the pin is removed when it is desirable to release the rod from the post, as is described above.

Figure 16A:
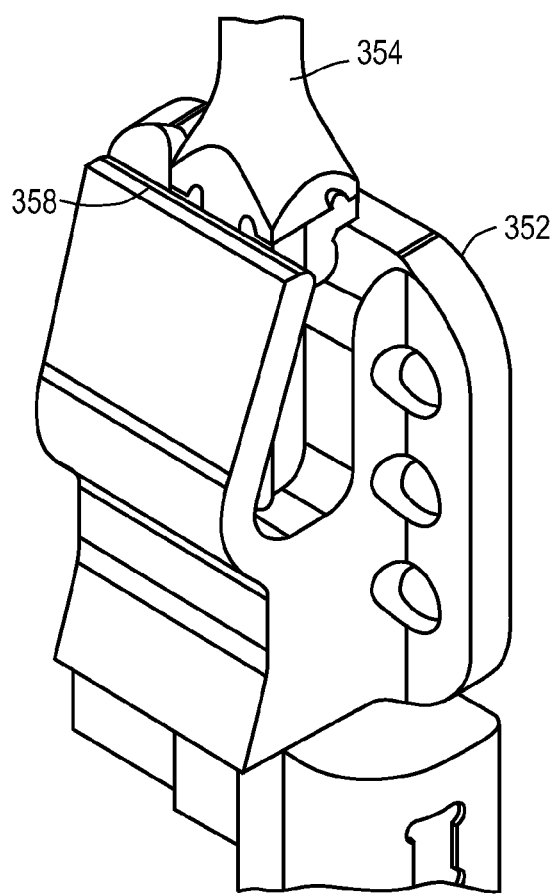
Figure 16B:
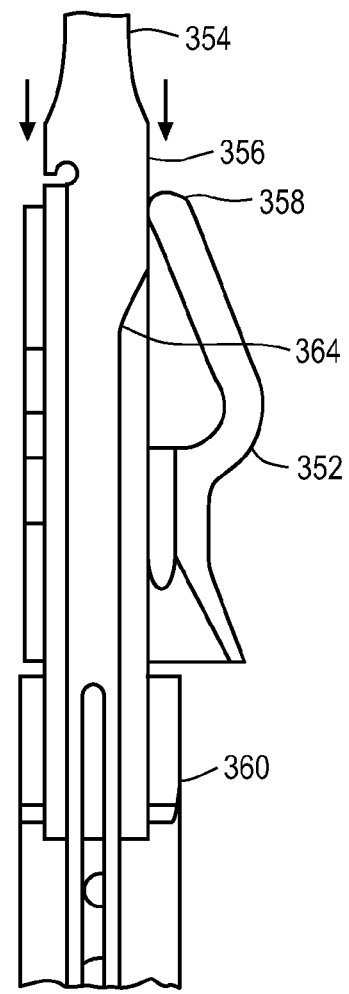
Figure 18A:
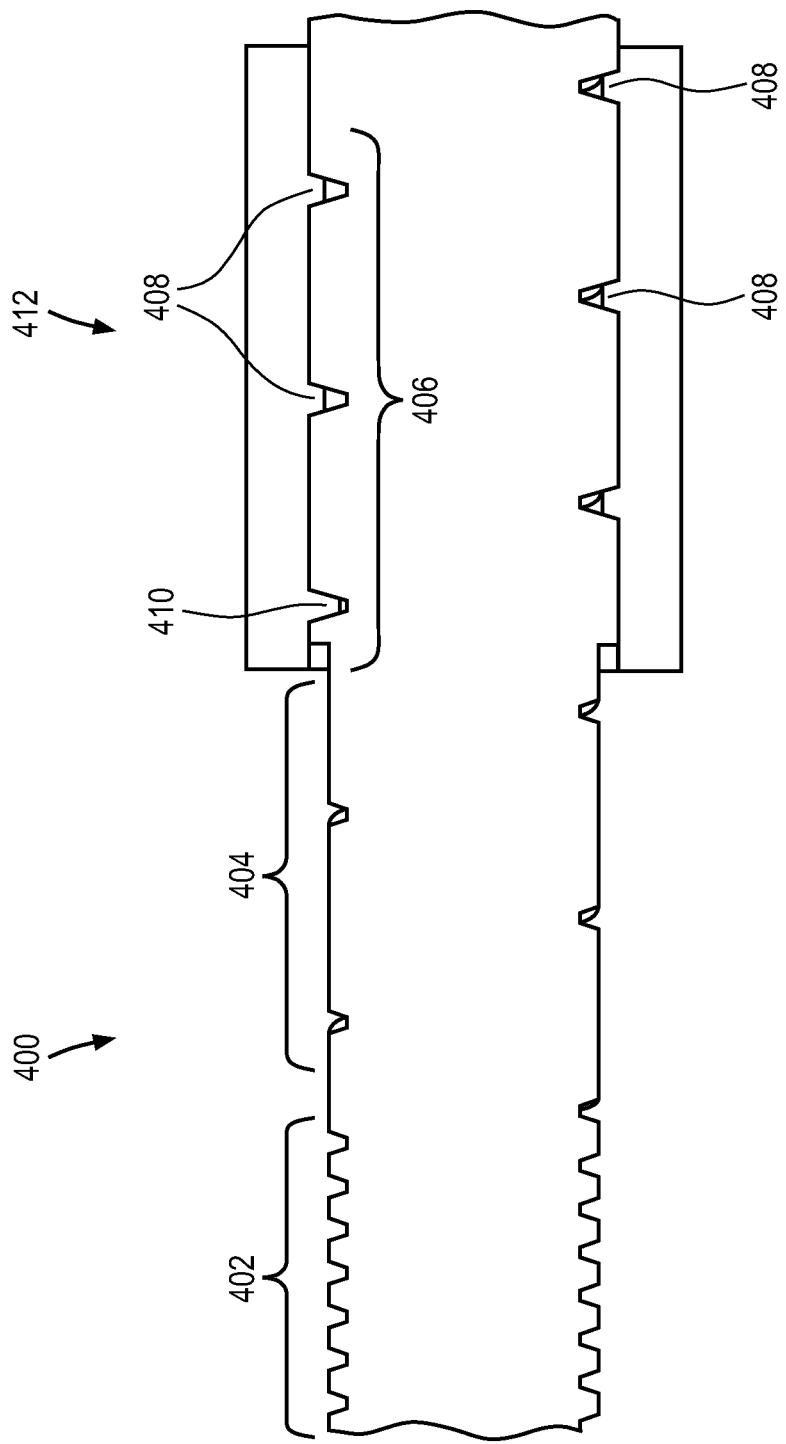
FIG. 18A-18D illustrate an varying pitch design to vary the rate of travel of an actuation element.
Figure 18B:
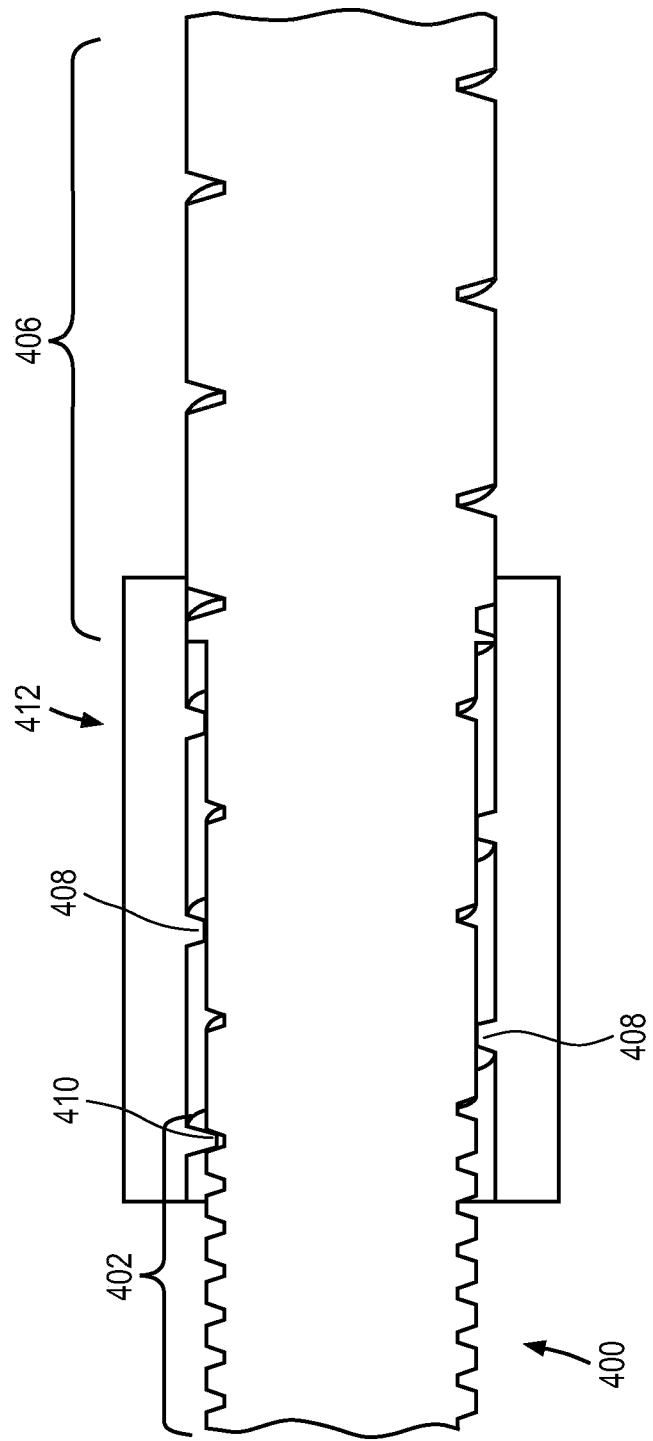
Figure 18C:
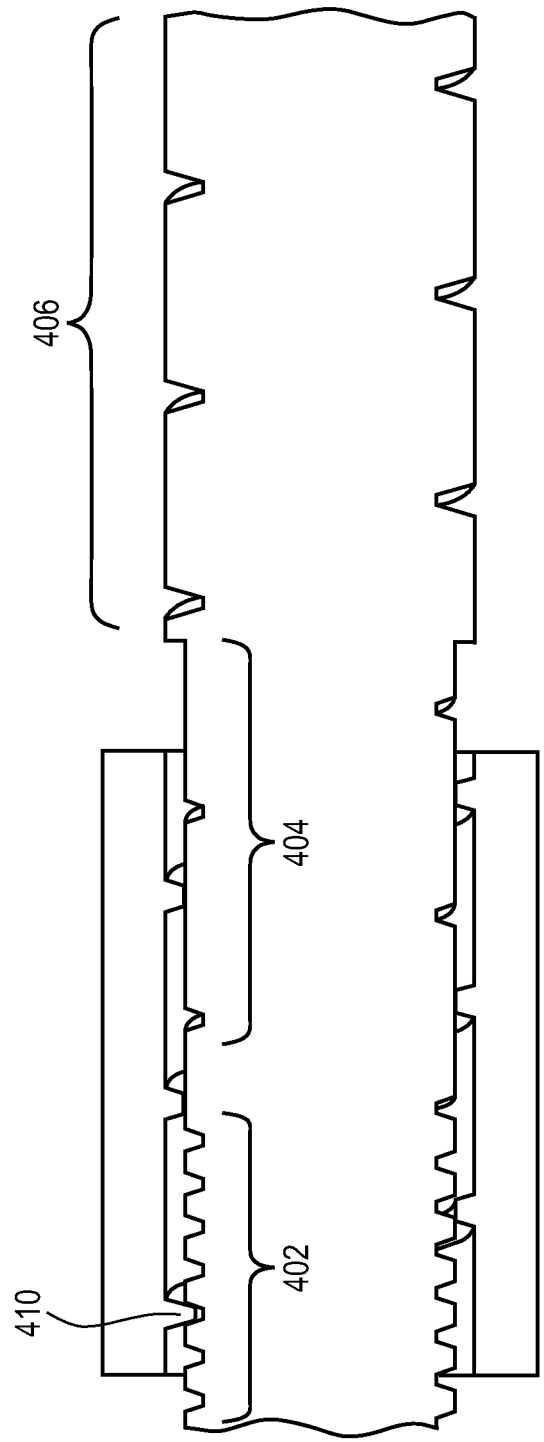
Figure 18D:
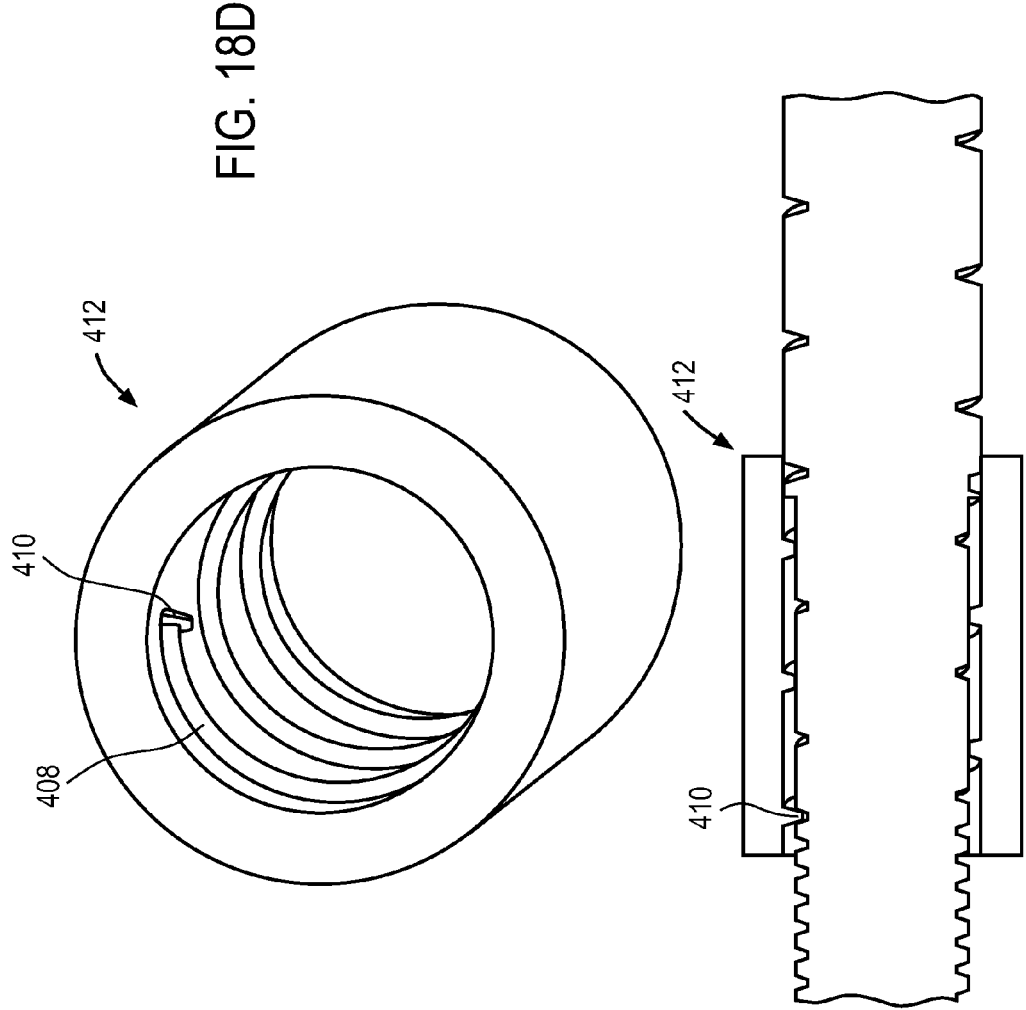

FIGS. 16A and 16B illustrate an unlocking of the post and buckle which are locked in FIGS. 15A and 15B. This unlocking step must be performed before the heart valve is released from the delivery system. Rod 354 is pushed distally, causing surface 364 (unlocking element) of the rod to engage and disengage tooth 358 from the groove in the post. Continued distal movement of the rod pushes the post in a distal direction, which lengthens the anchoring element.

In some embodiments, the fingers can be made of an alloy that is heat set to a memory expanded configuration. The rods can comprise, for example, stainless steel. The outer tube can be made of, for example, a heat-shrink polymer, but can be any suitable material. The outer tube provides enhanced column strength to the fingers, which can be advantageous when under the forces applied during the active foreshortening of the anchoring element.

In the embodiments above reference was made to a delivery system handle disposed external to the subject, which is used to control the actuation of the actuation elements and the sheath. The deployment of the medical implant as described herein can be controlled by actuators (e.g., knobs, levers, etc) on the handle, which are actuated by the physician to control the deployment of the device. It may be desirable to be able to perform multiple deployment steps with as few actuators as possible to simplify the delivery and expansion process. It may further be desirable to perform certain deployment steps with a single actuator, perhaps even actuating a single actuator with a singular type of movement (e.g., rotating a knob in a single direction) to perform multiple parts of the deployment process. This can make the procedure easier for the physician because a hand used to actuate the handle actuator does not need to be removed from the actuator to perform multiple steps. In some embodiments of the delivery system described below, the actuation steps of unsheathing the anchoring element and locking the posts with buckles are performed with a single actuator on a handle of the delivery system. Having a single actuator on the handle which can perform multiple deployment steps can simply the overall procedure. Using a single actuator to control multiple deployment steps can also insure that the steps are performed in a specified sequence, and making sure that a second step does not occur before the occurrence of a first step.

In embodiments described herein in which actuation of a single actuator in a singular type of motion moves a plurality of delivery system components, the singular type of motion can be performed to move more than one delivery system component without any other intervening actuation step being performed. In some embodiments, the user can stop the actuation of the actuator in the singular type of motion, and then continued the actuation. A singular type of motion includes embodiments in which a period of time passes without any actuation. That is, the user may start to actuate the actuator, wait a period of time (for example, to determine if the position of the medical device is sufficient based on an imaging technique), then continue to actuate the actuator. This falls under the "singular" type of motion as described here.

A potential challenge in using a single actuator to actuate multiple components of a delivery system arises when the actuatable components are to be actuated independently of one another, or when they are to be actuated independently of one another during portions of the procedure but actuated at the same time during other portions of the procedure, or when they must be actuated at the same time but at different rates of movement. Provided below are delivery systems in which actuation of a single actuator actuates a plurality of delivery system components wherein a first of the plurality of components and a second of the plurality of components are each actuated independent of the other. In some embodiments the first and second components are also adapted to be actuated at the same time as one another, and in some embodiments at different rates while they are both being actuated.

In some embodiments of the delivery system, a single actuator is used to both proximally retract the sheath during the unsheathing process (for example, as shown in the exemplary method in FIGS. 3B-3F) and to proximally retract the actuation elements which are coupled to the posts. That is, a single actuator is actuated in a single manner to both unsheath the implant as well as to lock the implant in a fully deployed and locked configuration. Incorporating a single actuator into the delivery system which can be actuated in one direction or manner to both deploy the implant from the sheath as well as reconfigure it to its final deployed configuration can greatly simplify the deployment procedure for the physician.

During a first portion of the deployment of the implant only the sheath is pulled in the proximal direction, which unsheathes the implant. During a second portion of the deployment only the posts are pulled proximally, which moves the posts towards the buckles to lock the anchoring element in the locked configuration. During a third portion of the procedure both the sheath and the actuation elements reversibly coupled to posts are pulled in the proximal direction, which may result in variable rates of movement of the sheath and the actuation elements. The single actuator must therefore account for both the dependent and independent motions of a plurality of delivery system components.

FIGS. 17A-17D illustrate an exemplary delivery system in which a single actuator on a handle selectively actuates a plurality of delivery system components. While this delivery system design can be used to selectively actuate a plurality of delivery system components in almost type of medical device delivery system, it will be described in relation to deployment of a replacement heart valve. In addition, while the single actuator can be adapted to actuate different types of components than those which are described herein, it will be described as controlling the movement of a sheath and an actuation element which actuates a portion of a replacement heart valve.

FIGS. 17A-17D show components of delivery system 370 which are housed inside a handle housing (not shown), including outer tube 380, rotary actuator 372 (which is adapted to be actuated by a user), lead screw 374, rod carriage 376, rod carriage screw 378, sheath carriage 384, sheath carriage screw 386. Proximal movement of rod carriage 376 moves the rods in the proximal direction, which causes a proximally directed force to be applied to the posts described herein (and distal movement of post puller carriage 206 causes a distally directed force to be applied to the posts). Proximal movement of sheath carriage 384 causes the sheath to be retracted proximally to unsheathe the implant (and distal movement of sheath carriage 384 causes the sheath to be moved distally to re-sheath the implant). In one embodiment, the sheath has an adapter bonded to its proximal end which is screwed to the sheath carriage. Movement of the sheath carriage, through rotation of the lead screw, therefore directly moves the sheath. In one embodiment the rods are bonded inside a hypotube and the hypotube is pinned to a force limiting member, which is directly attached to the rod carriage. Movement of the rod carriage therefore moves the rods. Rotation of rotary actuator 372 translates rotational movement into linear movement of rod carriage screw 378 and sheath carriage screw 386.

Tube 380 includes an internal female thread including a linear female thread 383 along two portions of tube 380 and a partially helically-shaped female thread 382 along a portion of the tube disposed between the linear female thread portions 383. Both the rod carriage screw 378 and sheath carriage screw 386 include an internal male thread which engages the female threads of screw 374 and allows rotation of actuator 372 to translate to movement of the rod carriage screw 378 and sheath carriage screw 386. The sheath carriage screw 386 includes male nub(s) 385 which engage linear female thread 383 in the configuration shown in FIG. 17A. The sheath carriage screw 386 also has an outer male thread 387 (see FIG. 17D) which engages with an internal female thread in sheath carriage 384. FIG. 17A shows the delivery system in a configuration in which the implant is sheathed within the sheath and the posts are not locked to the buckles. Initial rotation of actuator 372 causes sheath carriage screw 386 to move linearly in the proximal direction. Because of the interaction between the male thread 387 and the female thread within sheath carriage 384, proximal movement of sheath carriage screw 386 causes proximal movement of the sheath carriage 384, as is shown in the transition from FIG. 17A to 17B. This movement causes proximal movement of sheath, such as is required to begin unsheathing the implant to allow it to self-expand.

This initial rotation of the actuator 372 does not, however, translate into proximal motion of rod carriage 376. This initial rotation of actuator 372 causes rod carriage screw 378 to move proximally, but because rod carriage screw 378 has a male nub (not shown) similar to the male nub 385 on the sheath carriage screw, the rod carriage screw rotates within outer tube 380. The rod carriage 376 has an internal female thread which mates with male thread 379 on the rod carriage screw 378. These threads allow the rod carriage screw 378 to rotate within rod carriage 376 without causing the rod carriage to move proximally. This initial rotation of actuator 372 thereby results in lost motion of the rod carriage 376, as is shown in the transition from FIG. 17A to 17B. As the sheath begins to be pulled back, the rods therefore do not pull on the posts.

In the configuration in FIG. 17B, both males nubs of the carriage screws are aligned with the respective linear female threads 383. Continued rotation of actuator 372 therefore results in proximal movement of both of the carriage screws 386 and 378. Because of the threaded interaction between the carriages and their respective screws, both carriages move in the proximal direction This is illustrated in the transition from FIG. 17B to 17C. During this portion of the procedure, both the sheath and the rods are being pulled in the proximal direction.

In the configuration in FIG. 17C, the bottom male nub 385 (not shown) engages helical thread 382. Continued rotation of actuator 372 therefore results in rotation of sheath carriage screw 386 relative to outer tube 380. This causes sheath carriage screw 386 to unscrew from sheath carriage 384, as is shown in the transition from FIG. 17C to FIG. 17D. This results in the sheath carriage not moving in the proximal direction (i.e., lost motion). The threaded interaction between rod carriage 376 and rod carriage screw 378, however, translates into proximal movement of the rod carriage 376, as is shown in the transition from FIG. 17C to 17D. During this portion of the procedure, the rods are being pulled proximally but the sheath is not being actuated.

The movements of the carriages can also be reversed by rotating the actuator in the opposite direction.

It should be noted that the female threads on lead screw 374 can have a different pitch along the length of the screw, as is shown in FIGS. 17A-17D (although the pitch of the thread on lead screw 374 may also be constant along the length of lead screw 374). As shown, the pitch is greater on the portion where the sheath carriage screw interacts with the lead screw 374 than the pitch where the rod carriage screw interacts with the lead screw 374. This results in the sheath carriage moving a greater distance that the rod carriage during the transition from FIG. 17B to 17C. Thus, FIGS. 17A-17D illustrate not only lost motion but a different rate of motion of two moving delivery system components based on actuation of a single actuator (e.g., the rotary actuator 202).

FIGS. 18A-18D illustrates a sequence of movements of male threaded element 412 over female threaded element 400 which has a varying pitch and a varying diameter. The lead screw 374 from FIGS. 17A-17D can have the varying pitch and diameter of female element 400, and the carriage screws in FIGS. 17A-17D can incorporate the features of male element 412. Section 402 has a smaller pitch than sections 404 and 406, while the diameter of section 406 is greater than the diameter in sections 402 and 404. The lead portion of male thread 410 has a greater height (see FIG. 18D), which allows it to engage female thread 406,404, as well as 402. The male threads 408 have a smaller height than the lead portion. The male threads 408 are large enough to engage female threads 406, but not 404 or 402. This design allows for varying degrees of movement of male element 412 over the length of female threaded element 400. The male element 412 moves a greater distance when threaded in section 406 than in section 402, due to the difference in pitch. This can allow a delivery system component to move at first rate, followed by movement at a second rate (in this case, the second rate of movement is less than the first). This variable pitch design can be incorporated into any of the delivery systems described herein.

Figure 19:
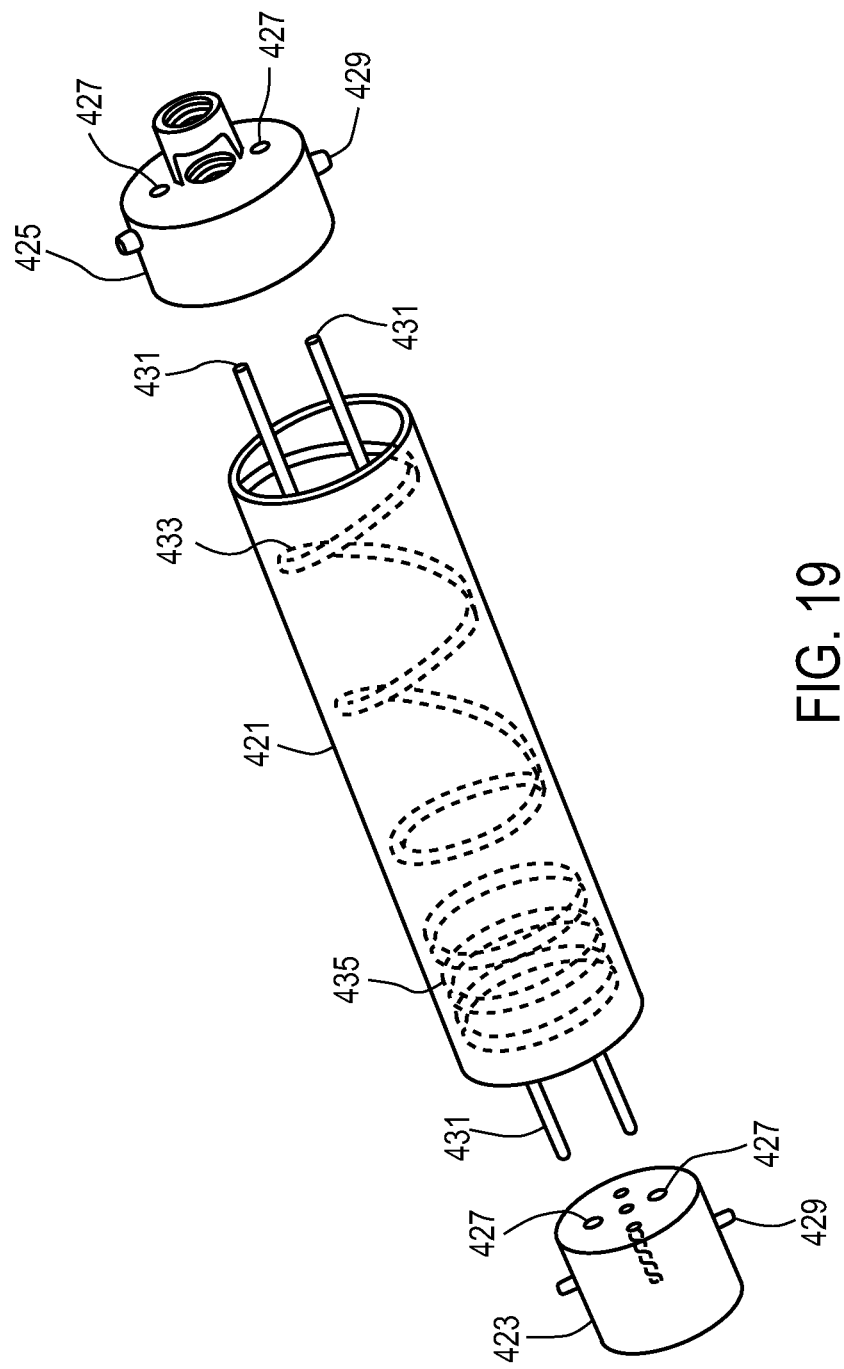
FIG. 19 illustrates an exemplary barrel-cam design to control the rate of movement of delivery system components.

FIG. 19 illustrates a barrel cam design which functions with a variable pitch in a similar manner to the design shown in FIGS. 18A-18D. One difference between the two embodiments is that threads 433 and 435 in the embodiment in FIG. 19 are integrated into barrel housing 421 instead of a central lead screw. As shown in FIG. 19, sheathing carriage 425 rotates on first thread 433 and rod carriage 423 rotates on second thread 435 in barrel housing 421. Lost motion is accounted for by bringing the pitch angle to, or near to, 0 so the carriage rotates but does not translate (or translates a minimal amount) within barrel housing 421. Each of the carriages also includes nubs 429 for tracking in threads 433 and 435. The carriages also include holes 427 for guide tubes 431.

FIGS. 20A-20C illustrate an alternative design to account for lost motion including handle housing 452, a pair of gears 454, rotary actuator 456, rod lead screw 458, rod carriage 460, rod carriage spring 462, rod carriage screw 464, sheathing lead screw 466, sheathing carriage 468, sheath carriage screw 470, sheath carriage spring 472. Rotary actuator 456 turns both gears 454, one geared to the rod lead screw 458 and one geared to the sheathing lead screw 466. Different pitches on each lead screw would allow for different linear motion rates for the rod screw 464 and sheathing screw 470. In an initial configuration shown in FIG. 20A, spring 462 is fully compressed and spring 472 is unloaded. Rotation of actuator 456 turns both lead screws 458 and 466, causing both the rod screw 464 and sheathing screw 470 to move proximally. The resistance to compression of spring 472 between the sheathing carriage 68 and sheathing lead screw 466 causes the sheathing carriage 468 to follow the proximal movement of sheathing screw 470, as is shown in the transition between FIGS. 20A and 20B. The force unloading of spring 462 causes the rod carriage 460 to remain stationary while rod screw 464 moves proximally, as is shown in the transition from FIG. 20A to FIG. 20B.

When the rod screw 464 reaches the proximal end of the rod carriage 460, continued rotation of actuator 456 causes both carriages to move, as is shown in FIG. 20B (both carriages in motion). Upon continued actuation of actuator 456, a stop (not shown in FIG. 20C) causes the sheathing carriage 468 to stop moving proximally. Continued rotation of the actuator 456 causes the continued movement of the sheath carriage screw 470 (but not sheath carriage 468) and the compression of spring 472. This allows for the locking of the anchor through proximal movement of the rod carriage 460 without motion of the sheath.

Actuating the actuator 456 in the reverse direction unlocks the anchor through distal motion of the rod carriage 460. Compression of spring 472 limits motion of the sheathing carriage 468 until the sheathing screw 470 is fully seated in the sheathing carriage 468. The two carriages then move together distally until the rod carriage 460 reaches a stop (not shown) causing the rod screw 464 to move distally while the rod carriage 460 does not move and spring 462 is compressed.

Figure 21:
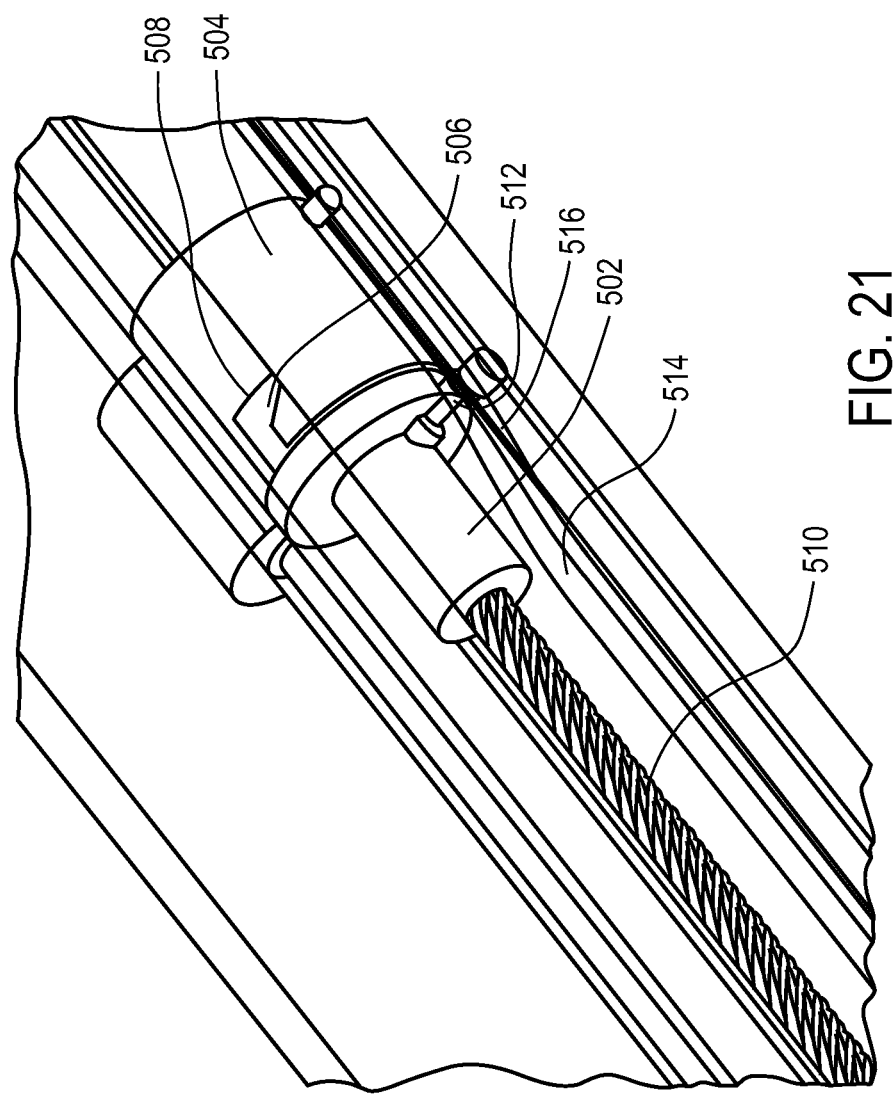
FIGS. 21-22 illustrate exemplary designs for decoupling the motion of the rods and outer sheath.
Figure 22:
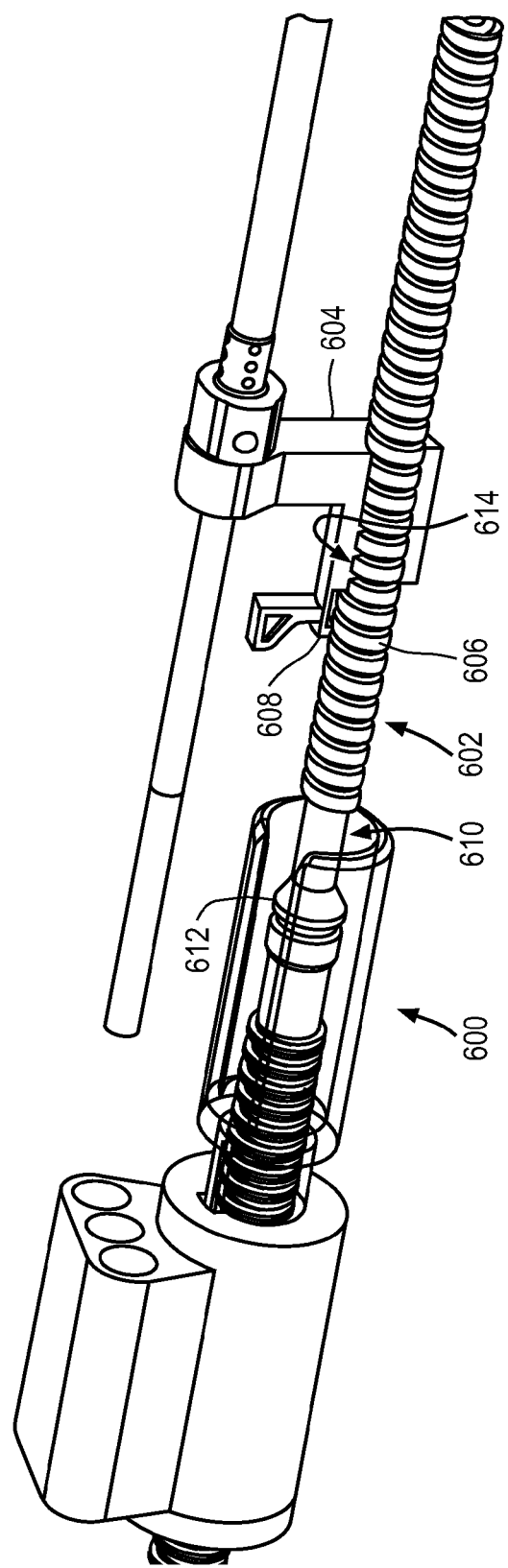

FIGS. 21-22 illustrate exemplary designs for decoupling the motion of the rods and outer sheath. In FIG. 21, a single actuator is geared to a gear with a cam on the proximal surface. The cam causes the engagement/disengagement of a clutch that is attached to a lead screw. When the clutch is engaged, the lead screw turns which causes a carriage (not shown) to move proximally or distally depending on the direction of movement of the actuator. When the clutch is not engaged, the lead screw does not turn and the carriage is stationary.

In FIG. 21 nut 502 (either for the rod or sheath) is connected to the carriage 504 (either for the rod or sheath) via a male tab 506 that engages with a female feature 508 in the carriage 504. The engagement between the nut 502 and the carriage 504 via the tab 506 causes the carriage 504 to move with the nut 502 as the lead screw 510 is turned (by an actuator not shown). The nut 502 has a nub 512 which travels along a path 514 in the housing. A jog 516 in the path 514 causes the nut 502 to rotate counterclockwise relative to the carriage 504. This motion causes the tab 506 to disengage from the female feature 508, releasing the nut 502 from the carriage 504. Since the nut 502 and carriage 504 are no longer joined, continued actuation (e.g., rotation) of the actuator moves only the nut 502. Rotating the actuator in the opposite direction causes the nut 502 to move back into contact with the carriage, reseating the nut tab 506 in the carriage and the carriage 504 then moves with the nut 502.

FIG. 22 shows a portion of delivery system 600 including lead screw 602 with region 606 with female thread and region 610 without threads. Sheath carriage 604 includes male threads 614 which engage with female threads 606 on lead screw 602. Sheath carriage 604 also includes lock element 608 which is adapted to engage with lock lip 612 on lead screw 602 to lock the carriage 604 onto lead screw and prevent the carriage 604 from moving in the distal direction D. Rotation of an actuator on the handle (not shown) causes lead screw 602 to rotate, which causes the carriage 604 to move proximally. This retracts the sheath in the proximal direction without moving the posts. Continued proximal movement causes lock element 608 to engage and lock with lock lip 612. Because the lead screw does not have any threads in region 610, continued rotation of lead screw 602 does not result in movement of the carriage 604.

Figure 23A:
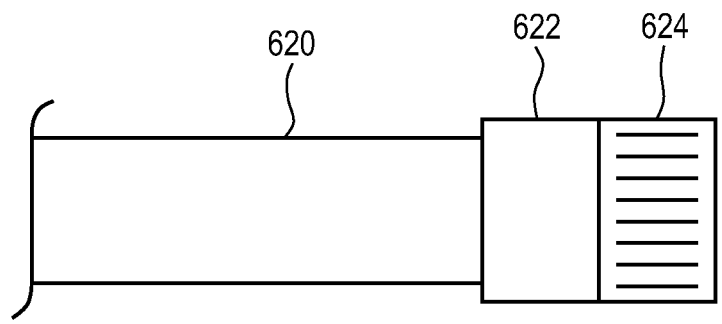
Figure 23B:
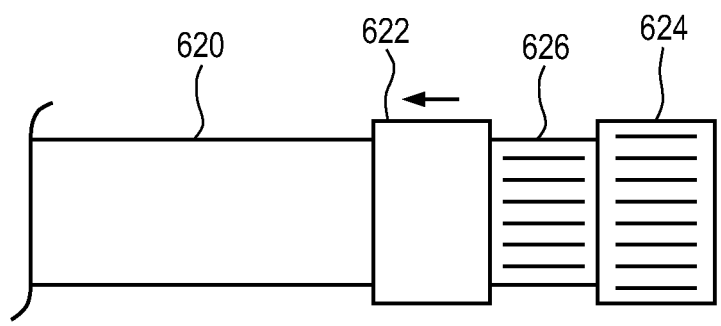
Figure 25:
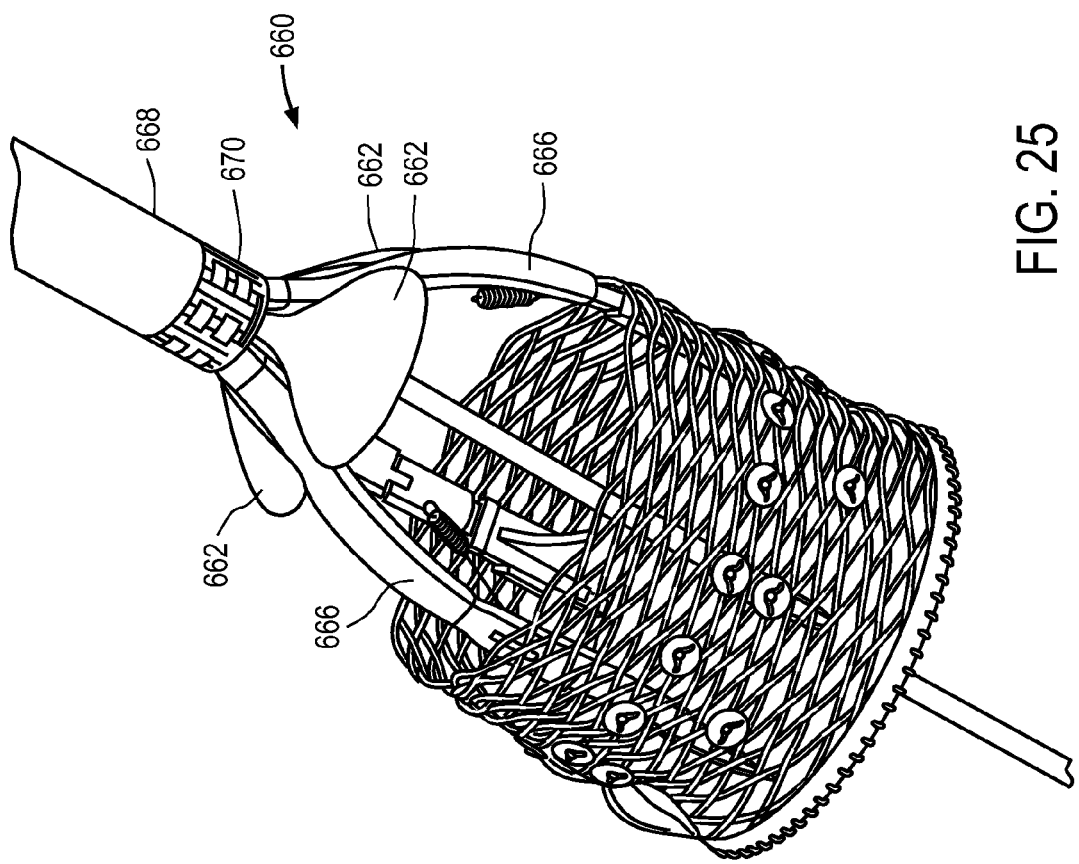

FIGS. 23A and 23B illustrate a proximal portion of an exemplary handle which is used in the deployment of the heart valve shown in FIGS. 4 and 5A-5B. The handle includes housing 620, first actuator 624 in the form of a rotary actuator, slidable door 622, and second actuator 626 which can only be accessed when the door 622 has been slid forward from the first position in FIG. 25A to the second position in 25B. In this embodiment, rotary actuator 624 controls the movement of the sheath (such as is shown in FIGS. 3B-3F) and the movement of actuation elements 206B shown in FIGS. 4 and 5A-5B. In one embodiment, actuator 624 controls the movement of sheath and the actuation elements as shown in FIGS. 17A-17C, such that actuation of actuator 624 independently and dependently moves the sheath and actuation elements. Once the anchoring element is locked by the locking of posts to buckles, the physician slides door 622 to the position shown in FIG. 23B and actuates second actuator 626. Actuation of actuator 626 retracts pin assembly 236 in FIG. 4, which causes the three pins 234 to be removed from the bores through the posts and actuation elements, uncoupling the posts from the actuation elements 206B.

In one embodiment, continued actuation of actuator 626 also further retracts the actuation elements 206B from the position shown in FIG. 5B to the position shown in 5E. FIG. 23C illustrates an enlarged portion of handle 630 of an exemplary delivery system with a design which allows continued actuation of actuator 626 to further retract actuation elements 206B (second actuator 626 from FIGS. 23A and 23B not shown). The locking and sheathing drive ring actuates the locking and sheathing carriages via the lead screw similarly to the method described in reference to FIGS. 17A-17D. Handle 630 includes locking and sheathing drive ring 631, locking and sheathing lead screw 632, locking carriage 633, release pin carriage 635, lost motion barrel 629, release pin mandrels 636 (shown within hypotube), rod actuation mandrels 634 (shown within a hypotube), and force limiter 638. Force limiter 638 includes track 637 in which release pin carriage 635 moves when pulled proximally. The release collar actuates a separate smaller lead screw 639 (normally driven by locking carriage 633) which pulls proximally release pin carriage 635. When the physician is ready to remove the pins, the second actuator on the handle (not shown) is actuated, which engages the release lead screw 639, causing it to rotate. This pulls release collar 636 proximally in track 637, which causes release pin mandrels 636 to be pulled back proximally, releasing the pins from the posts and uncoupling the rods from the posts. Continued actuation of the second actuator continues to pull the release carriage until it reaches the proximal end of force limiter 638. When carriage 635 bottoms out on the proximal end of force limiter 638, it moves the portion of the force limiter in which it sits proximally relative to the other portion of the force limiter. This causes rod mandrels 634 to be pulled proximally, which pulls the rods in the proximal direction. Thus, the second actuator can be used to release the pins as well as continue to pull the rods back in the proximal direction.

The medical implants described herein can be recollapsed and resheathed at least partially back inside the sheath after the entire implant has initially been deployed from the sheath. This is because at least a portion of the implant remains reversibly coupled to a portion of the delivery system after the implant is deployed from the sheath (e.g., see FIG. 3F). Even after the anchoring element is locked in the fully deployed configuration, the post can be unlocked from the buckle in some embodiments and thereafter the anchoring element can be resheathed into the sheath. Being able to resheath an implant after it has been deployed from a delivery sheath or catheter is advantageous because it allows for the implant to be removed from the patient or repositioned inside the patient if needed. For example, the functionality and/or positioning of a replacement heart valve can be assessed once the replacement heart valve is in the configuration shown in FIG. 3F (and continually assessed as the anchor begins to be locked in the expanded and locked configuration), and can then be resheathed and subsequently repositioned or removed from the patient if needed.

While the resheathing processes and delivery systems to perform the resheathing described herein make references to replacement heart valves, a wide variety of medical devices may benefit from the resheathing aids described herein. For example, an expandable stent which remains reversibly coupled to the delivery system after the stent has been deployed from a delivery catheter or sheath may benefit from having any of the resheathing aids described herein incorporated into the delivery systems thereof.

To resheath the heart valve, the sheath is advanced distally relative to the catheter. Alternatively, the catheter can be withdrawn proximally relative to the sheath. Distal movement of the sheath relative to the catheter causes the fingers, which are coupled to the distal end of the catheter, to collapse radially inward. This causes the proximal end of the anchor to collapse. Continued distal movement of the sheath causes the rest of the heart valve to elongate and collapse, allowing the sheath to recapture the anchoring element.

In embodiments in which the anchoring element comprises a braided material, distal advancement of the sheath may result in portions of the proximal end of the anchor to get caught, or stuck, on the distal end of the sheath. This can prevent resheathing or it can reduce the resheathing efficiency.

Figure 24:
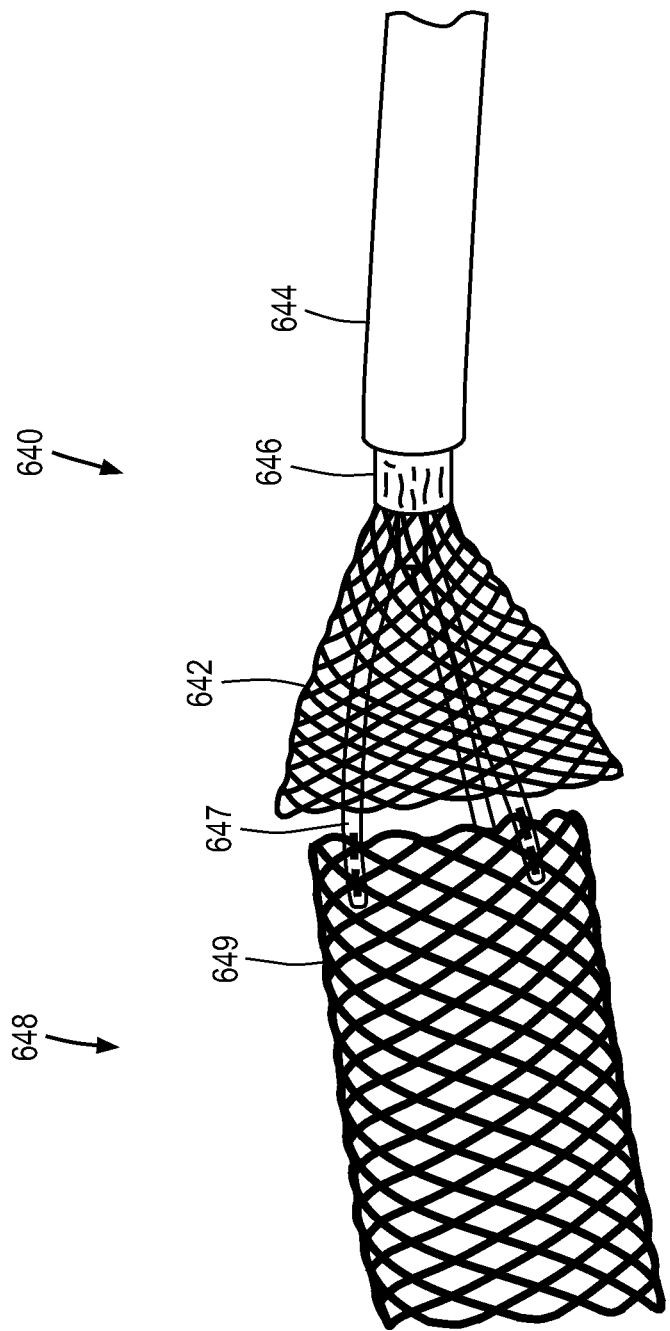
FIGS. 24-41 illustrate a variety of medical device sheathing assist elements.

FIG. 24 illustrates an alternative delivery system 640 including sheath 644, delivery catheter 646, and sheathing assist element 642. Sheathing assist element 642 is a braided structure, and can be similar to the braided anchoring elements described herein. The sheathing assist element 642 generally has a memory configuration in which the distal end of the sheathing assist element 642 has a diameter larger than the diameter of the proximal end of the anchoring element 649. The delivery system includes fingers 647 (only two can be seen) reversibly coupled to a proximal region of replacement heart valve 648 (replacement leaflets not shown for clarity). The proximal end of sheathing assist element 642 is coupled to the distal end of delivery catheter 646. Fingers 647 are also coupled to the distal end of catheter 646, and are generally "within" or radially inward relative to sheathing assist element 642. FIG. 24 shows a replacement heart valve after the sheath has been withdrawn, allowing the anchoring element to expand to a memory configuration, and has not yet been actively foreshortened.

To resheath the implant, the sheath is advanced distally relative to the catheter and implant. This can be done by actuating an actuator of a handle, as described above. Because the proximal end of the sheathing assist element is fixed to the distal end of the delivery catheter, the distal end of the sheath can easily pass over the proximal end of the sheathing assist element without getting caught. Continued distal movement of the sheath causes at least the distal portion of the sheathing assist element to elongate and partially collapse in diameter. As the sheathing assist element elongates, the distal end of the sheathing assist element moves distal relative to the proximal end of the anchor. Continued distal movement of the sheath continues to collapse the distal end of the sheathing assist element and at least a distal region of the sheathing assist element will engage at least the proximal end of the anchor. The sheathing assist element will therefore provide a surface over which the sheath can pass without the risk of getting caught on the proximal end of the anchor. The sheathing assist element may additionally apply a radially inward force to the proximal end of the anchor, assisting in the collapse of the proximal end of the anchor. As the sheath continues to be advanced distally, the anchor is collapsed and is resheathed back within the sheath. In some embodiments the sheathing assist element is a polymer mesh.

In some embodiments the sheathing assist element can also act as an embolic filter. Once unsheathed, the sheathing assist element can trap emboli traveling downstream to the target location, yet allowing blood to pass through the assist element. In such embodiments, the distal end of the sheathing assist element can be configured and arranged to have a memory diameter that is as close as possible to the diameter of the lumen in which it is to be disposed. Exemplary materials for embolic filters are known in the art.

FIGS. 25-28 illustrate alternative delivery systems with alternative sheathing assist element 660. Sheathing assist element 660 includes three (3) collapsible blades 662. The blades are fixed to one another at their proximal ends at hub 664 (see FIG. 28). Hub 664 is axially movable relative to fingers 666 and catheter 668, but the distal region of catheter 668 includes a hub stop 670 which is adapted to engage with the hub and prevent movement of the hub proximally relative to the hub stop. As sheath (not shown) is advanced distally over catheter 668, it begins to collapse fingers 666. As the fingers collapse radially inward, the hub can then move distally over the fingers. As the fingers collapse, the proximal end of the anchor begins to collapse and the hub continues to be advanced distally. Eventually the distal ends of blades 662 cover the proximal end of the anchor, and the sheath can then be advanced over the anchor without getting caught on the proximal end of the anchor. In some embodiments the blades are adapted to collapse inwards on themselves as the sheath applies a force to them.

Figure 26:
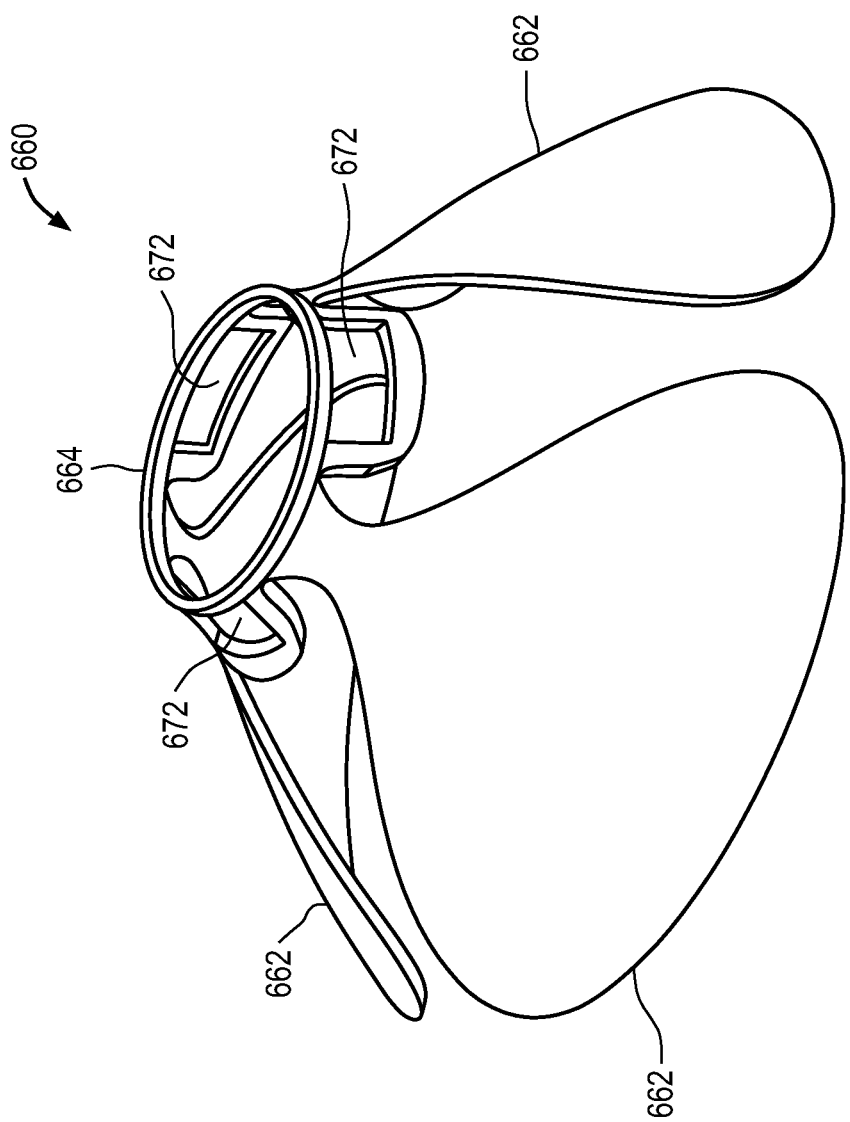
Figure 27:
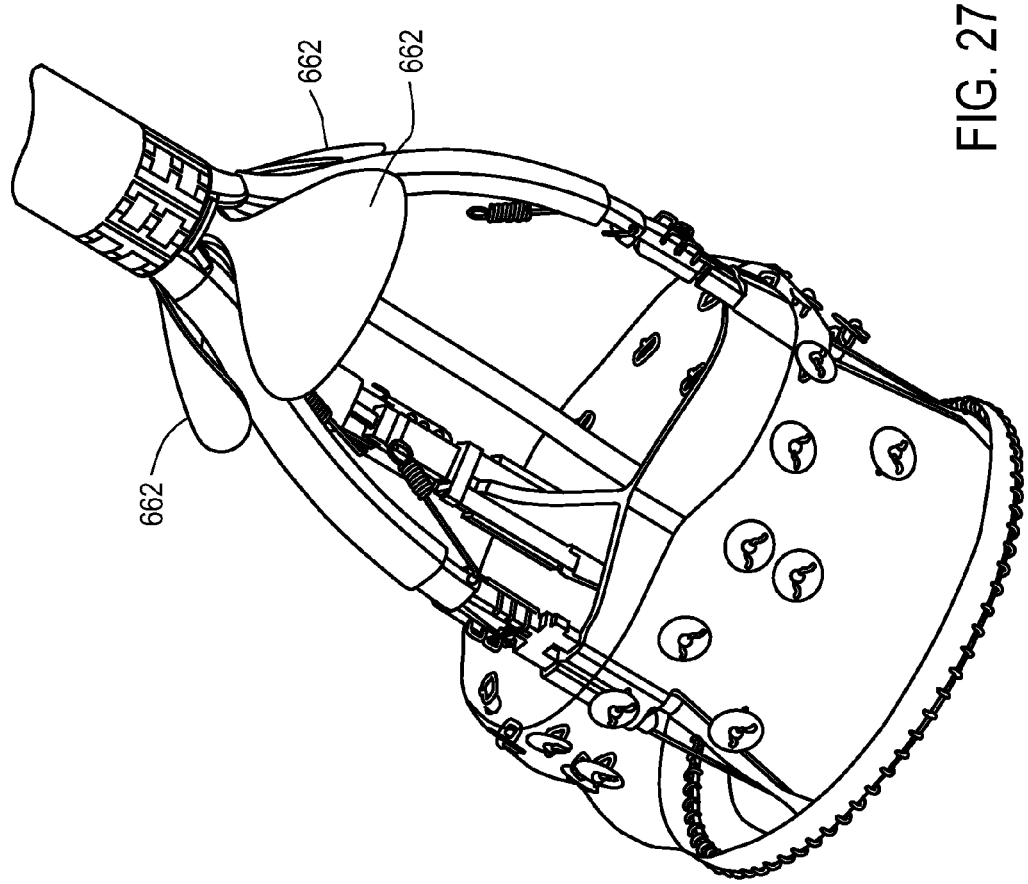
Figure 28:
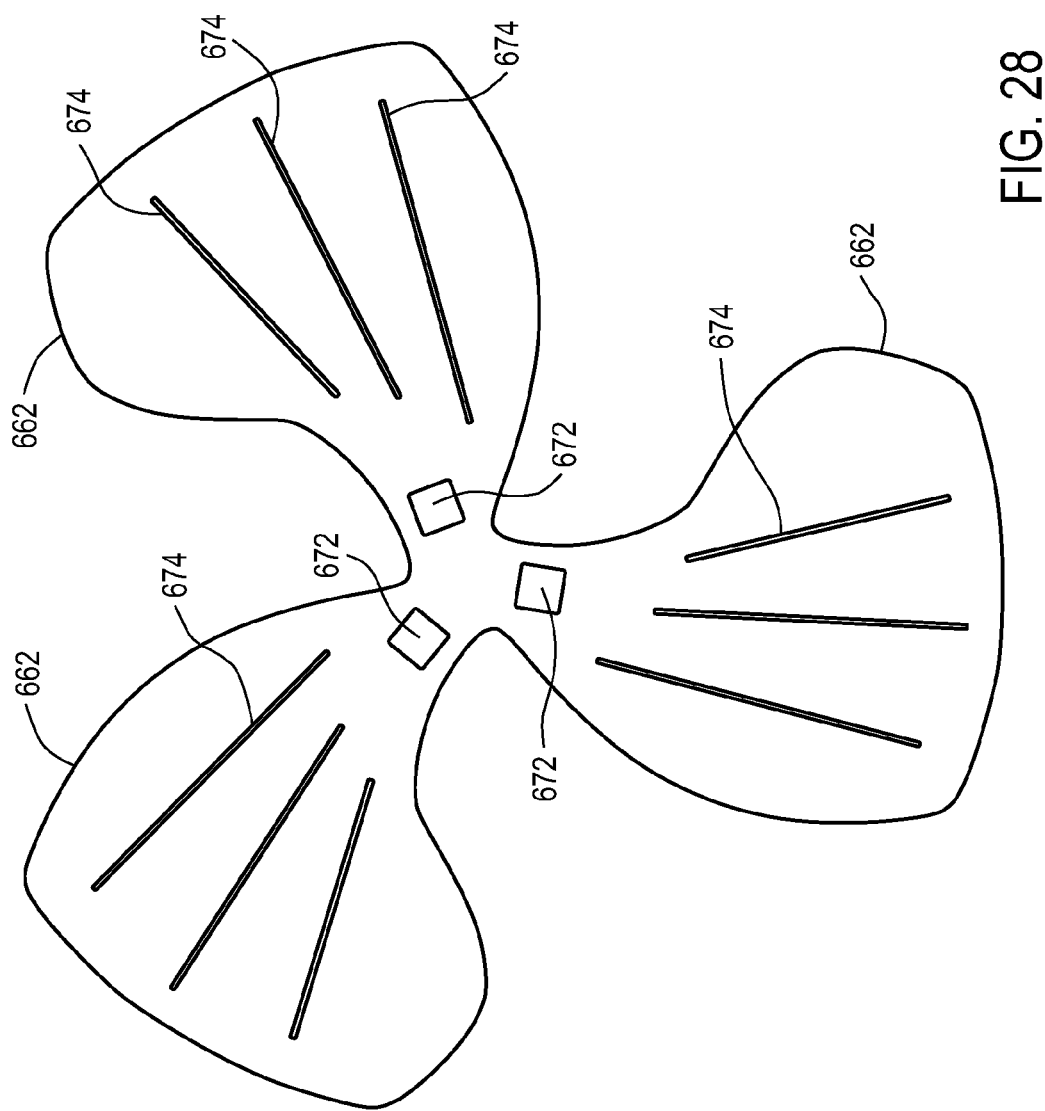

In the embodiment shown in FIG. 26, sheathing assist element 660 includes optional finger openings 672 which are adapted to allow the fingers to be passed therethrough. Openings 672 can be designed to have any shape (e.g., rectangular, circular, etc) to allow the hub to be easily moved distally relative to the fingers. In the embodiment in FIG. 28, the blades have optional slits 674 to assist in their collapse.

Figure 29:
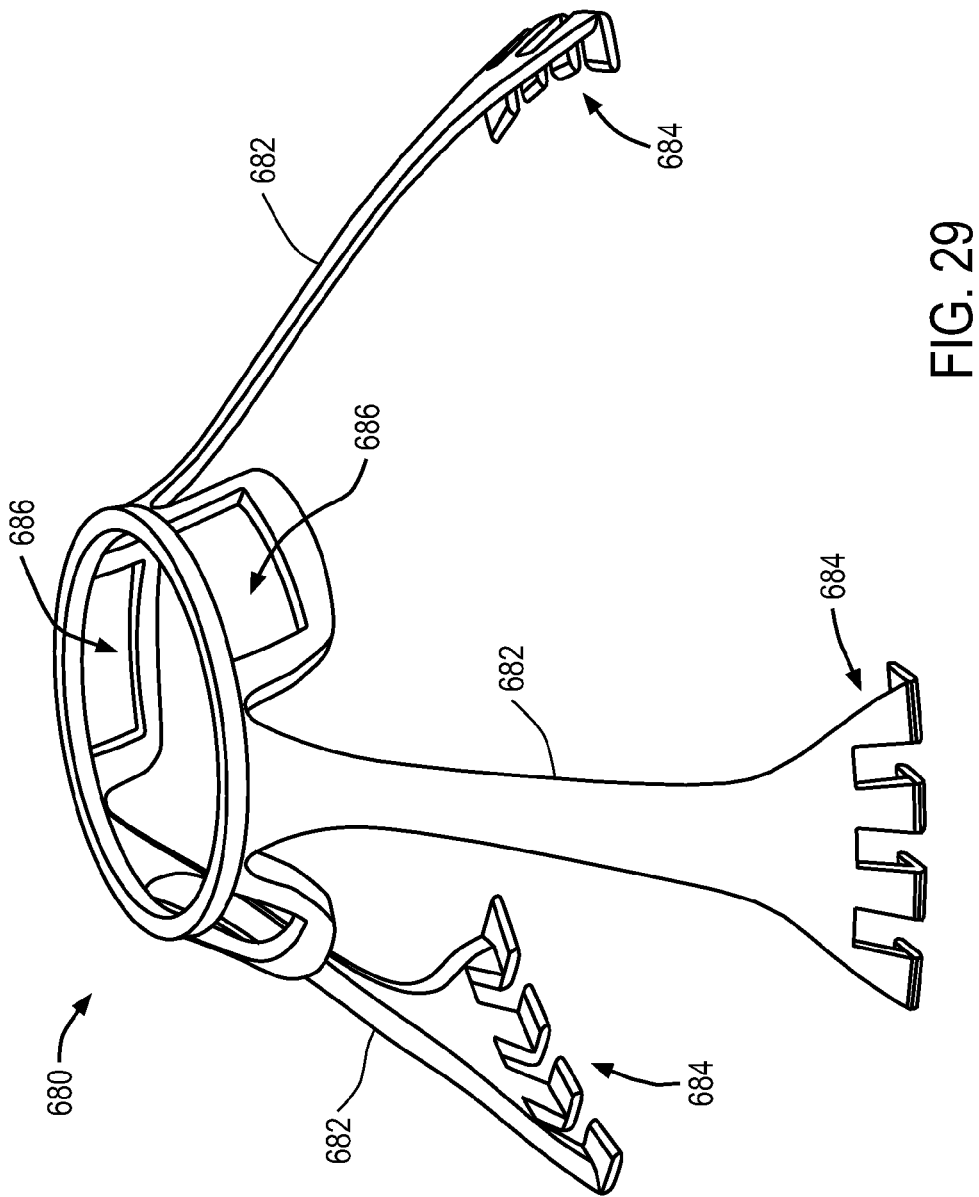

FIG. 29 shows an embodiment of sheathing assist element 680 which include arms 682 and teeth 684 at their distal ends. The teeth are adapted to engage the crowns of the braid, which are formed where a brand strand turns at an end of the braid (or other proximal region of a non-braided anchor) and allow the sheath to be advanced distally over the anchor. Each arm 682 can have any number of teeth 684. The arms can be adapted to respond to an applied force from the sheath such that they change to a second configuration with a bend such that a distal portion of the arms are bent radially inward to engage the proximal end of the anchor.

Figure 30:
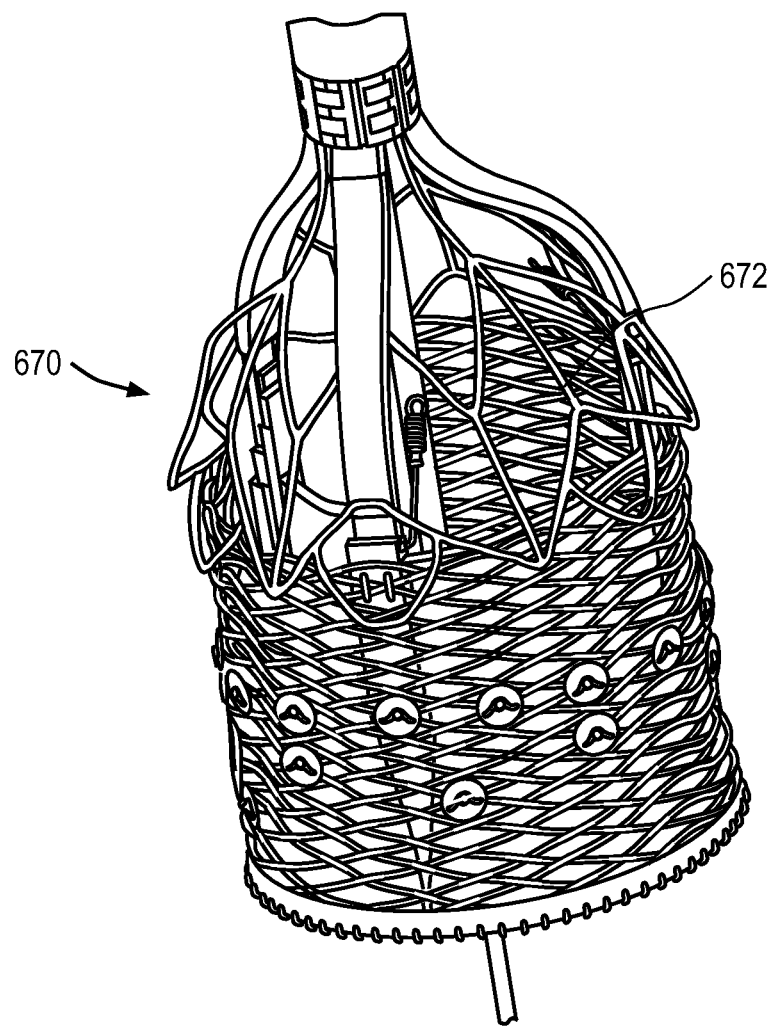

FIG. 30 shows an alternative embodiment of a sheathing assist element 670 which is comprised of stent element 672. Sheathing assist element 670 functions similar to the embodiment shown in FIG. 26, but is not comprised of a braided material. The stent can be made from, for example, an alloy or any other suitable material as is known in the art of stents.

Figure 31:
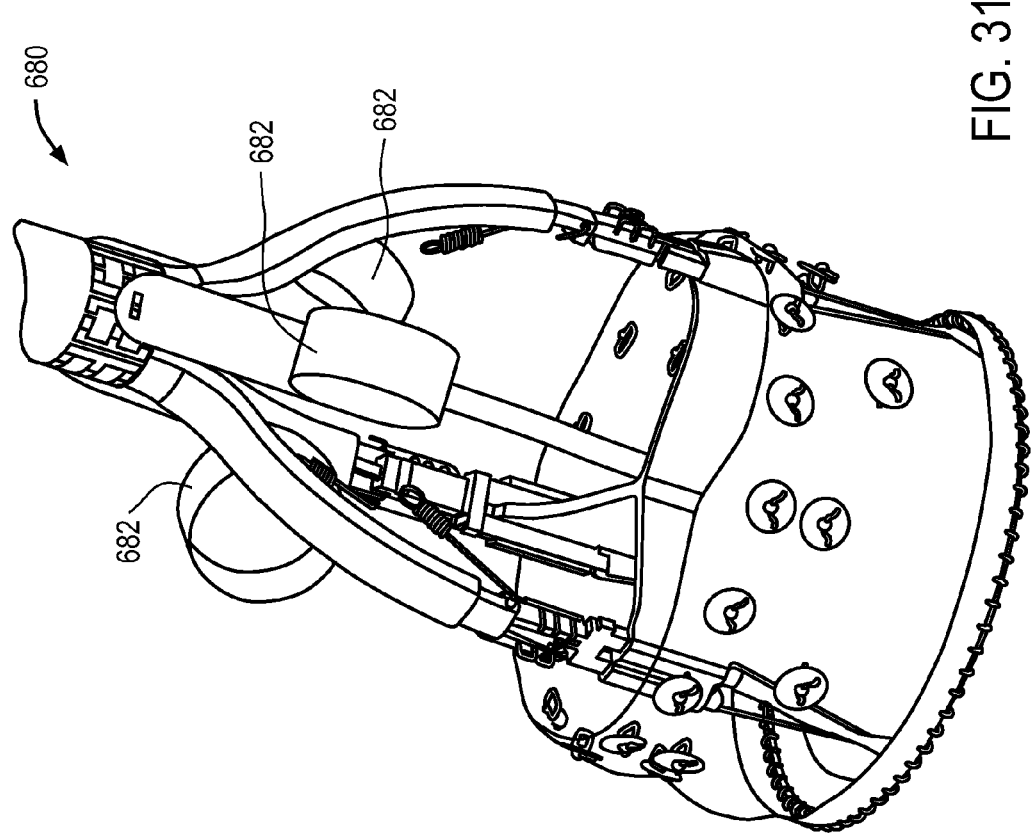

FIG. 31 shows an alternative embodiment of sheathing assist element 680 which includes curled elements 682 (anchor not shown). The proximal end of the curled elements 682 can be coupled to a hub as described above in other embodiments, or each of the curled elements can be individually affixed to the catheter. As the sheath is advanced distally, the force of the sheath causes the distal ends of the curled elements to uncurl and straighten. The distal ends of the straightened element extend over and distal to the proximal end of the anchor, and allow the sheath to be advanced over the proximal end of the anchor without getting caught on the crowns of the anchor. The curled elements can be made of, for example, stainless steel or any other suitable material.

Figure 32:
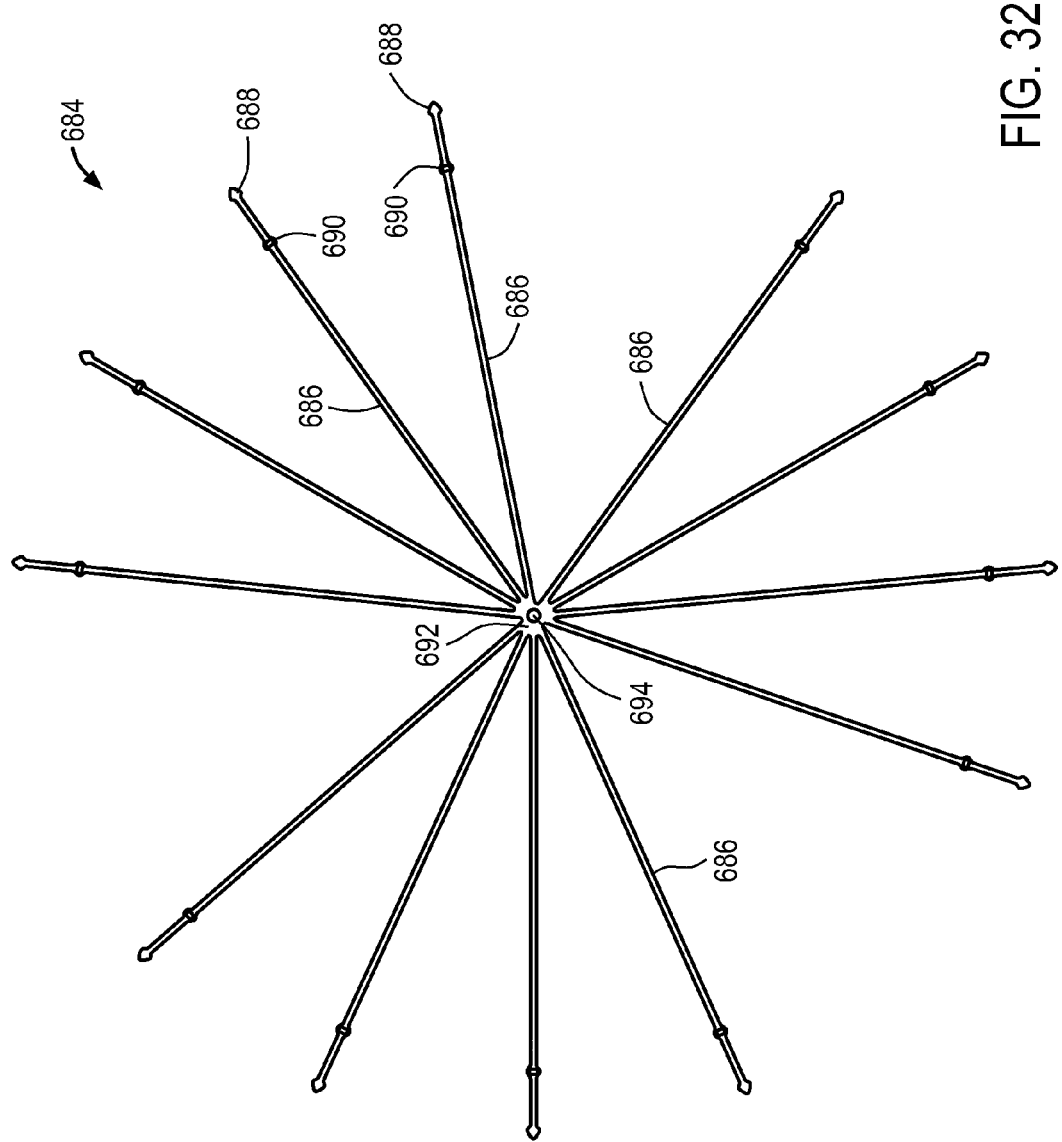
Figure 33:
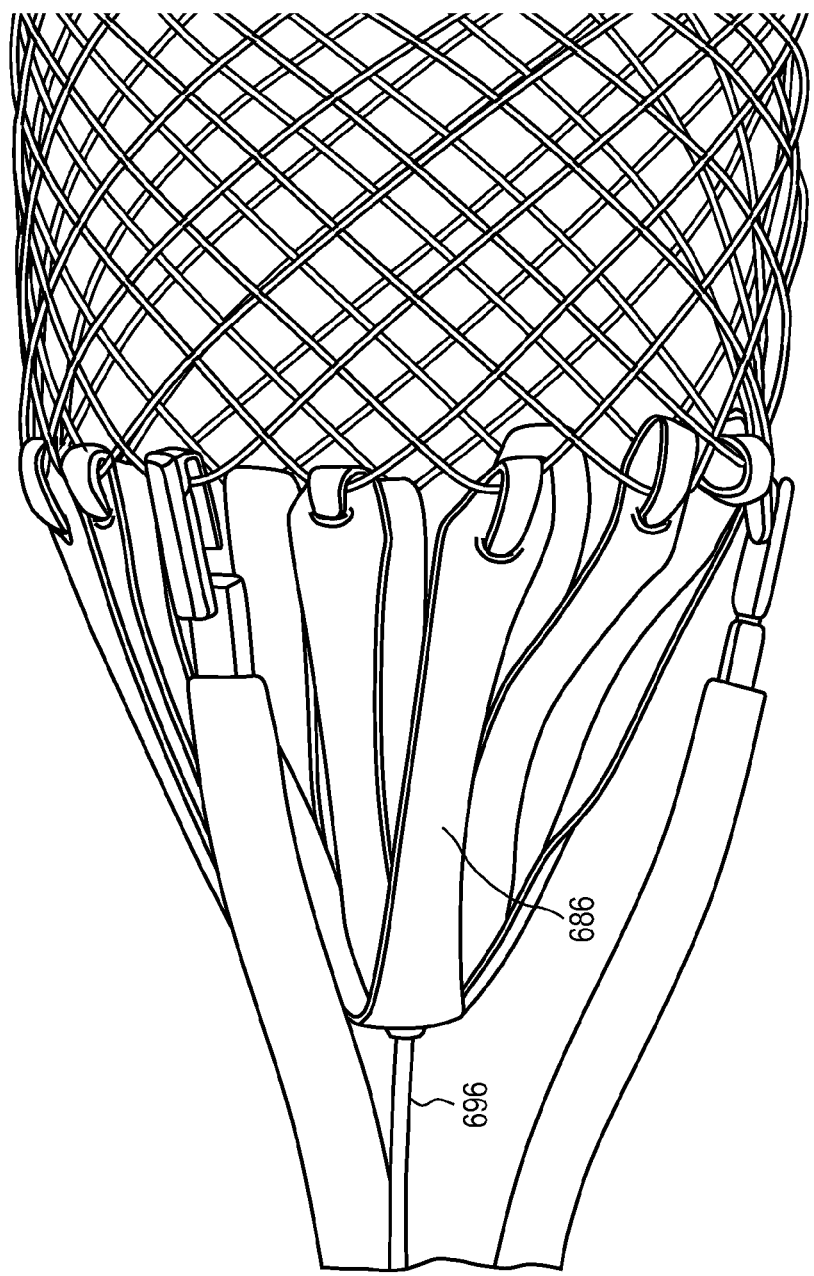
Figure 34:
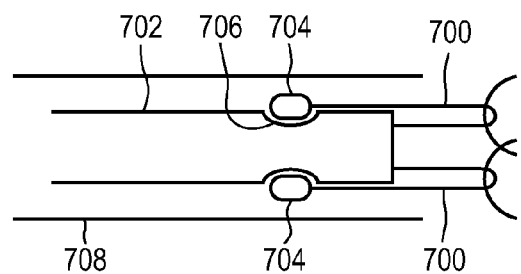
Figure 35:
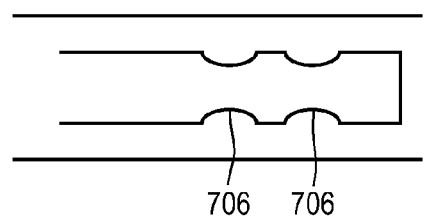
Figure 36:
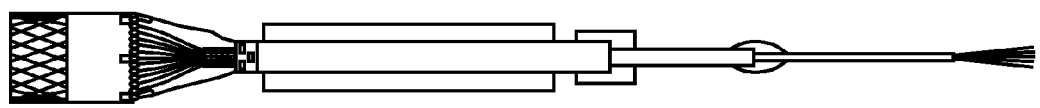
Figure 37:
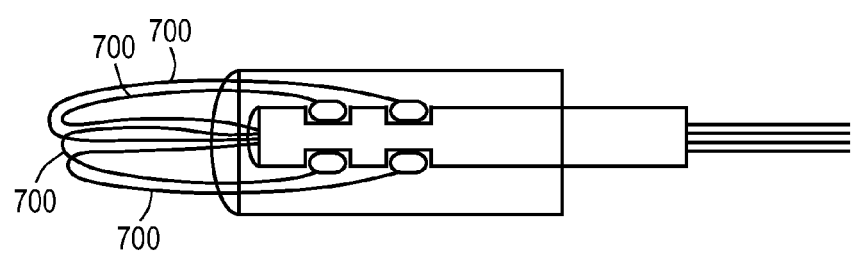

In an alternative embodiment shown in FIGS. 32 and 33, sheathing assist element 684 comprises a plurality of arms 686 (twelve arms are shown in FIGS. 32 and 33), each which have a distal end with male locking element 688. Each arm 686 includes female locking element 690 disposed closer to hub 692 than the male locking element 688. In FIGS. 32 and 33, the male locking elements have an arrowhead shape and the female lock elements are slot-shaped. Hub 692 includes an opening 694 therein to allow control wire 696 to pass therethrough. Control wire 696 has an enlarged element at its distal end (not shown) which prevents the enlarged element from being pulled proximally through opening 694. In the delivery configuration, each arm 686 extends distally from hub 692 and the distal region of each arm distal to the slot is wrapped around a crown of the anchor (see FIG. 33). The male lock elements 688 are engaged with female lock elements 690. When the replacement heart valve is to be resheathed, a proximally directed force is applied to the control wire 696, which prevents the crowns from extending radially outward, thus allowing the sheath to be advanced distally over the crowns of the proximal end without getting stuck. Alternatively, a proximal force is not required, and the engagement of arms 686 and the crowns of the anchor prevent the crowns from getting stuck on the sheath. A proximally directed force on the hub will release the arrowheads from the slots, releasing the arms from the anchors. This releases the implant from the arms.

In alternative embodiments shown in FIGS. 34-37, the delivery systems include wires or sutures 700 which are coupled at their proximal ends to a delivery system component (e.g., the distal end of catheter 702, an actuator in a handle, etc.), and are each wrapped around a crown of the anchor. The distal ends of wires or sutures 700 have an enlarged element 704 such as a spherical element which is adapted to engage with annular detent 706 in the outer surface of catheter 702. Sheath 708 maintains the engagement of the enlarged element 704 and detent 706. The distal end of the wire or suture 700 can simply comprise one locking element while the catheter outer surface can include a second locking element. The sutures 700 provide a radially inward force to the crowns, helping the sheath extend over them during resheathing. Once the outer sheath is pulled proximally relative to the catheter, the enlarged element is released from the indent, and the wire/suture 700 can be released from the crowns of the anchor. In the alternative exemplary embodiment shown in FIG. 35 the catheter includes multiple detents 706.

Figure 40:
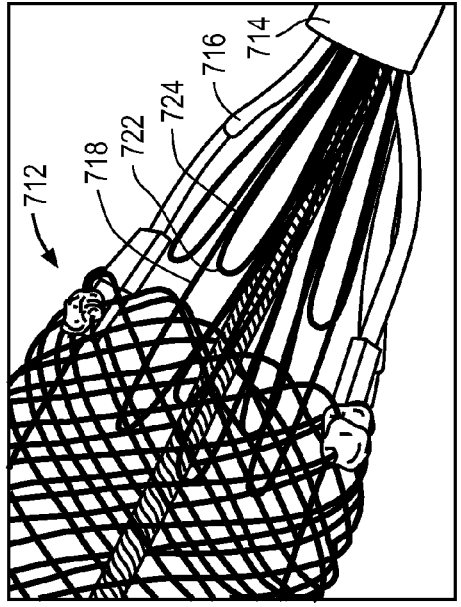
Figure 38:
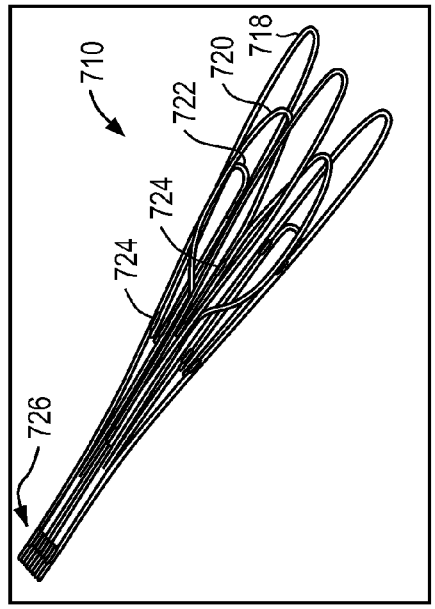
Figure 39:
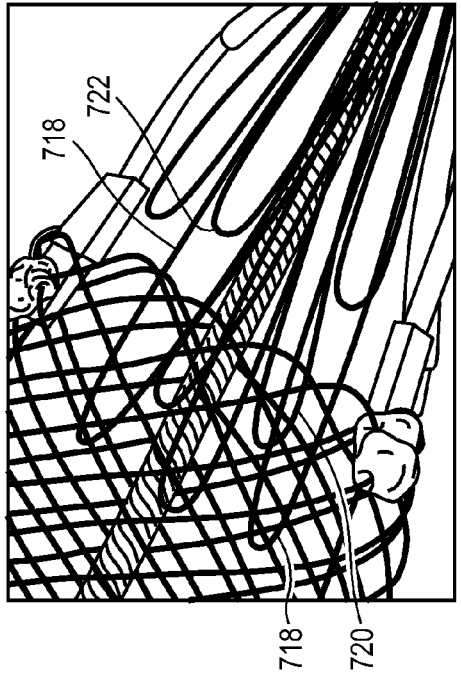
Figure 41:
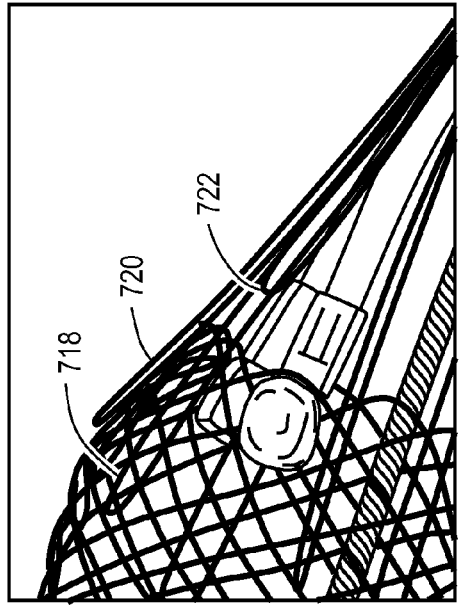

FIGS. 38-41 illustrate an alternative embodiment of sheathing assist 710, which includes a plurality of arms attached to the distal end of catheter 714. The arms include two types of arms 718 and 720, wherein arms 718 are slightly longer than arms 720. The arms are formed from a wire segment with a bend at their distal ends, wherein the two ends of the arms are coupled together at the proximal end 726 of the sheathing assist 710. Arms 718 extend from the catheter to the anchor and the distal ends are weaved into the braid of the anchor. That is, the distal ends of arms 718 are disposed radially within the braided anchor, as can be seen in FIGS. 39-41. Arms 718 are attached to stiffening elements 722, which are shorter than both arms 718 and arms 720. Stiffening element 722 is attached to arm 718 at attachment point 724, which can be, for example, a weld. As can be seen, stiffening elements 722 are disposed within the wire segments of arms 718, which increases the strength of arms 718. Sheathing assist also includes arms 720 which are shown shorter than arms 718, although they could both be substantially the same length. As can be seen in FIG. 38, two arms 720 are attached together at attachment points 724. Arms 720 are positioned radially outwards of braid, unlike arms 720 which are weaved into the braid and disposed radially inside the braid. Arms 720 help apply a radially inward force on the braid as the sheath is advanced distally. Arms 718 also help apply a radially inward force on the braid as well, and the two sets of arms ensure that the distal end of the sheath doesn't get caught on the anchor.

In an alternative embodiment, the proximal crowns of the braided anchor are heat-set in a configuration in which the crowns are bent radially inward (relative to longitudinal axis of the braid and relative to the rest of the anchor), to assist the sheath in the re-sheathing process. The crowns are bent inward to prevent the sheath from getting caught on the crowns.

Although the present disclosure has been described in connection with the exemplary embodiments described above, those of ordinary skill in the art will understand that many modifications can be made thereto. Accordingly, it is not intended that the scope of the present disclosure in any way be limited by the above exemplary embodiments.

What is claimed is:

1. A method of deploying a medical device in a patient with a delivery system, comprising:
    providing a delivery system comprising a housing disposed external to the patient, wherein the housing comprises an actuator;
    actuating the actuator to move a first delivery system component independently of a second delivery system component;
    actuating the actuator to move the first delivery system component and the second delivery system component at the same time; and
    rotating the actuator to translate rotational movement into linear movement.

2. The method of claim 1, wherein actuating the first and second delivery system components comprises actuating the actuator with a singular type of motion.

3. The method of claim 1, wherein the acts of actuating the actuator actuate the first and second delivery system components in a particular sequence.

4. The method of claim 1, wherein the actuator is a first actuator, and wherein the housing further comprises a second actuator, the method further comprising:
    actuating the second actuator to uncouple the second delivery system component from the medical device.

5. The method of claim 4, wherein actuating the second actuator to uncouple the second delivery system component from the medical device further comprises:
    retracting a pin assembly of the delivery system.

6. The method of claim 4, wherein the housing further comprises an access door, the method further comprising:
    moving the access door to access the second actuator.

7. The method of claim 1 wherein the delivery system further comprises a first gear and a second gear, wherein the actuator turns both the first gear and the second gear;
    wherein the first delivery system component is coupled to the first gear and engaged to the actuation element; and
    wherein the second delivery system component is coupled to the second gear and engaged to the sheath.

8. The method of claim 7, wherein the delivery system further comprises:
    a first lead screw that couples the first delivery system component to the first gear; and
    a second lead screw that couples the second delivery system component to the second gear;
    wherein the first gear is geared to the first lead screw, and wherein the second gear is geared to the second lead screw.

9. The method of claim 8, wherein the first lead screw has a first pitch and the second lead screw has a second pitch, the first pitch being different from the second pitch.

10. The method of claim 8, wherein the delivery system further comprises:
    a first spring engaged to the first lead screw; and
    a second spring engaged to the second lead screw; and
    the method further comprises:
    turning the first gear to uncompress the first spring and move the first delivery system component, and
    turning the second gear to compress the second spring and move the second delivery system component.

11. A method of deploying a medical device in a patient with a delivery system, comprising:
    providing a delivery system comprising a housing disposed external to the patient, wherein the housing comprises a first actuator and a second actuator;
    actuating the first actuator to move a first delivery system component independently of a second delivery system component;
    actuating the first actuator to move the first delivery system component and the second delivery system component at the same time;
    rotating the first actuator to translate rotational movement into linear movement; and
    actuating the second actuator to uncouple the second delivery system component from the medical device.

* * * * *